US006794544B2

(12) United States Patent
Babiak et al.

(10) Patent No.: US 6,794,544 B2
(45) Date of Patent: Sep. 21, 2004

(54) METHOD FOR THE PREPARATION OF TETRAHYDROBENZOTHIEPINES

(75) Inventors: Kevin A. Babiak, Evanston, IL (US); Andrew Carpenter, Zebulon, NC (US); Shine Chou, St. Louis, MO (US); Pierre-Jean Colson, Skokie, IL (US); Payman Farid, Vernon Hills, IL (US); Robert Hett, Aarau (CH); Christian H. Huber, Sosforth, Newcastle-upon Thyme (GB); Kevin J. Koeller, Richmond Heights, MO (US); Jon P. Lawson, Glencoe, MO (US); James Li, Hopewell Township, NJ (US); Eduardo K. Mar, Northbrook, IL (US); Lawrence M. Miller, Des Plaines, IL (US); Vladislav Orlovski, Wheeling, IL (US); James C. Peterson, Manchester, MO (US); Mark J. Pozzo, Chesterfield, MO (US); Claire A. Przybyla, Des Plaines, IL (US); Samuel J. Tremont, St. Louis, MO (US); Jay S. Trivedi, Skokie, IL (US); Grace M. Wagner, Webster Groves, MO (US); Gerald A. Weisenburger, Evanston, IL (US); Benxin Zhi, Hoffman Estates, IL (US)

(73) Assignee: Pharmacia Corporation, Chicago, IL (US)

( * ) Notice: Subject to any disclaimer, the term of this patent is extended or adjusted under 35 U.S.C. 154(b) by 2 days.

(21) Appl. No.: 10/204,826

(22) PCT Filed: Mar. 8, 2001

(86) PCT No.: PCT/US01/07421

§ 371 (c)(1),
(2), (4) Date: Dec. 23, 2002

(87) PCT Pub. No.: WO01/68637

PCT Pub. Date: Sep. 20, 2001

(65) Prior Publication Data

US 2003/0236406 A1 Dec. 25, 2003

Related U.S. Application Data

(60) Provisional application No. 60/188,361, filed on Mar. 10, 2000.

(51) Int. Cl.[7] .................... C07C 211/00; C07C 315/00; C07C 205/00; C07C 207/00
(52) U.S. Cl. ..................... 564/315; 568/30; 568/424; 568/585
(58) Field of Search ............................ 564/315; 568/30, 568/424, 585

(56) References Cited

U.S. PATENT DOCUMENTS

| 2,783,277 | A | | 2/1957 | Hiltmann et al. | |
|---|---|---|---|---|---|
| 4,680,402 | A | * | 7/1987 | Majoie et al. | 546/235 |
| 5,679,866 | A | * | 10/1997 | Curtze et al. | 568/333 |
| 5,994,391 | A | * | 11/1999 | Lee et al. | 514/431 |
| 6,140,270 | A | * | 10/2000 | Rampulla et al. | 504/239 |
| 6,156,700 | A | * | 12/2000 | Wepplo et al. | 504/242 |
| 6,191,275 | B1 | * | 2/2001 | Kameswaran | 544/310 |
| 6,268,392 | B1 | * | 7/2001 | Keller et al. | 514/431 |
| 6,329,405 | B1 | * | 12/2001 | Kurata et al. | 514/357 |
| 6,355,796 | B1 | * | 3/2002 | Kameswaran | 544/96 |
| 6,387,924 | B2 | * | 5/2002 | Lee et al. | 514/300 |
| 6,420,417 | B1 | * | 7/2002 | Keller et al. | 514/431 |
| 6,586,434 | B2 | * | 7/2003 | Babiak et al. | 514/249 |
| 6,642,268 | B2 | * | 11/2003 | Keller et al. | 514/431 |

FOREIGN PATENT DOCUMENTS

| EP | 1 070 703 A | 1/2001 |
|---|---|---|
| WO | WO 99/32478 | 7/1999 |
| WO | WO 00/01687 | 1/2000 |

OTHER PUBLICATIONS

International Search Report for PCT/US01/07421, 2001.

Braun et al., "Synthesen in der Fettaromatischen Reibe: XVI: Gechlorte Amine and Aminosäuren," Justus Liebigs Ann. Chem., vol. 455, pp. 225–246 (1925).

Ullmann et al., "Ueber eine neue Synthese von Phenylacridinderivaten," Chem. Ber., vol. 39, pp. 298–310 (1906).

Kuwahara et al., Synthetic Studies on Condensed–Azole Derivatives. IV. Synthesis and Anti–asthmatic Activities of ω–Sulfamoylalkyloxyimidazol(1–2.b)pyridazines, Chem. Pharm. Bull. vol. 44, No. 1, pp. 122–131 (1996).

Pennings et al. "Chemistry of Four–Membered Cyclic Nitrones. 5. Synthesis and Oxidation of 1–Hydroxyazetidines," J. Org. Chem. vol. 48, No. 22, pp. 4043–4048 (1981).

Hua et al. "Asymmetric Synthesis of (+)–Hirsutene," J. Org. Chem., vol. 53, No. 2, pp. 507–515 (1988).

Kent C. Brannock, "Preparation of Substituted 4–Pentenals," J. Am. Chem. Soc., vol. 81, pp. 3379–3383 (1959).

Wada et al., "The Wittig–Type and the Claisen Rearrangement of Allylic 3–Phenylthio–2–Propen–1–yl–Ethers." Chem. Lett. No. 5, pp. 557–560 (1977).

Kraynack et al., "Intermolecular Pinacol Coupling of Sulfur–Substituted Aldehydes by $(V_2Cl_2(THF)_e]2(Zn_2Cl_8)$. The Effects of the Substitution at sulfur on the Stereochemical Outcome of the Coupling Reaction", J. Org. Chem. vol. 58, No. 22 pp. 6114–6117 (1993).

* cited by examiner

Primary Examiner—Deborah C. Lambkin
(74) Attorney, Agent, or Firm—Banner &Witcoff, Ltd.

(57) ABSTRACT

Among its several embodiments, the present invention provides an improved process for the preparation of tetrahydrobenzothiepine-1,1-dioxide compounds; the provision of a process for preparing a diastereomeric mixture of tetrahydrobenzothiepine-1,1-dioxide compounds from a single diastereomer of such compounds; the provision of a process for the preparation of 3-bromo-2-substituted propionaldehyde compounds; and the provision of a process for the preparation of 3-thio-2-substituted propionaldehyde compounds.

-continued
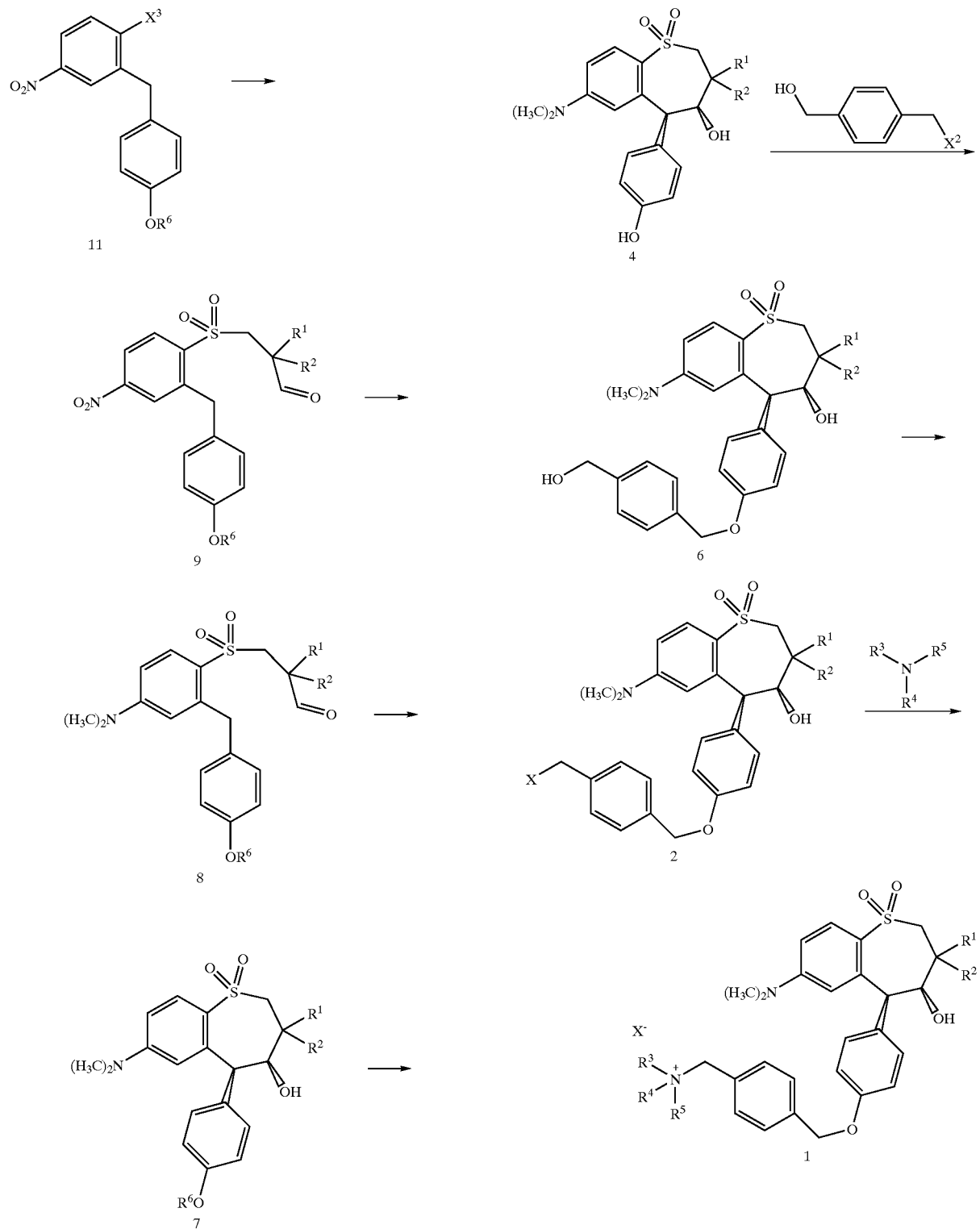
45 Claims, 11 Drawing Sheets

(a) Form I of Compound 41.

(b) Form II of Compound 41.

(a) Form I of Compound 41.

(b) Form II of Compound 41.

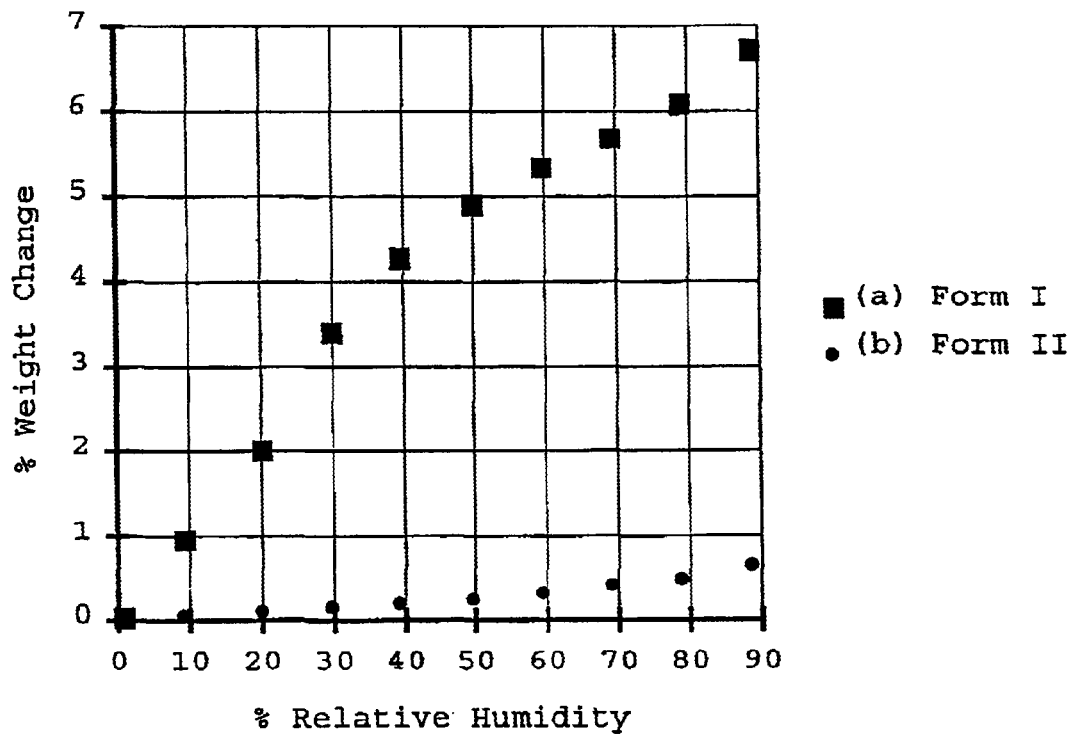
Figure 10. Water Sorption Isotherms for Form I and Form II at 25°C

METHOD FOR THE PREPARATION OF TETRAHYDROBENZOTHIEPINES

This is a U.S. National Phase Application Under 35 USC 371 and applicants herewith claim the benefit of priority of PCT/US01/07421 filed Mar. 8, 2001, which was published under PCT Article 21(2) in English, and of U.S. Provisional Application Serial No. 60/188,361 filed Mar. 10, 2000.

BACKGROUND OF THE INVENTION

1. Field of the Invention

This invention relates to the preparation of apical sodium co-dependent bile acid transporter (ASBT) inhibitors and more particularly to the preparation of benzothiepine ASBT inhibitors. This invention especially relates to methods of preparing tetrahydrobenzothiepine oxide ASBT inhibitors.

2. Description of Related Art

It is well established that agents which inhibit the transport of bile acids across the tissue of the ileum can also cause a decrease in the levels of cholesterol in blood serum. Stedronski, in "Interaction of bile acids and cholesterol with nonsystemic agents having hypocholesterolemic properties," Biochimica et Biophysica Acta, 1210 (1994) 255–287 discusses biochemistry, physiology, and known active agents surrounding bile acids and cholesterol. Bile acids are actively transported across the tissue of the ileum by an apical sodium co-dependent bile acid transporter (ASBT), alternatively known as an ileal bile acid transporter (IBAT).

A class of ASBT-inhibiting compounds that was recently discovered to be useful for influencing the level of blood serum cholesterol comprises tetrahydrobenzothiepine oxides (THBO compounds, PCT Patent Application No. WO 96/08484). Further THBO compounds useful as ASBT inhibitors are described in PCT Patent Application No. WO 97/33882. Additional THBO compounds useful as ASBT inhibitors are described in U.S. Pat. No. 5,994,391. Still further THBO compounds useful as ASBT inhibitors are described in PCT Patent Application No. WO 99/64409. Included in the THBO class are tetrahydrobenzothiepine-1-oxides and tetrahydrobenzothiepine-1,1-dioxides. THBO compounds possess chemical structures in which a phenyl ring is fused to a seven-member ring.

Published methods for the preparation of THBO compounds include the synthesis through an aromatic sulfone aldehyde intermediate. For example 1-(2,2-dibutyl-3-oxopropylsulfonyl)-2-((4-methoxyphenyl)methyl)benzene (9) was cyclized with potassium t-butoxide to form tetrahydrobenzothiepine-1,1-dioxide (syn-24) as shown in Eq. 1.

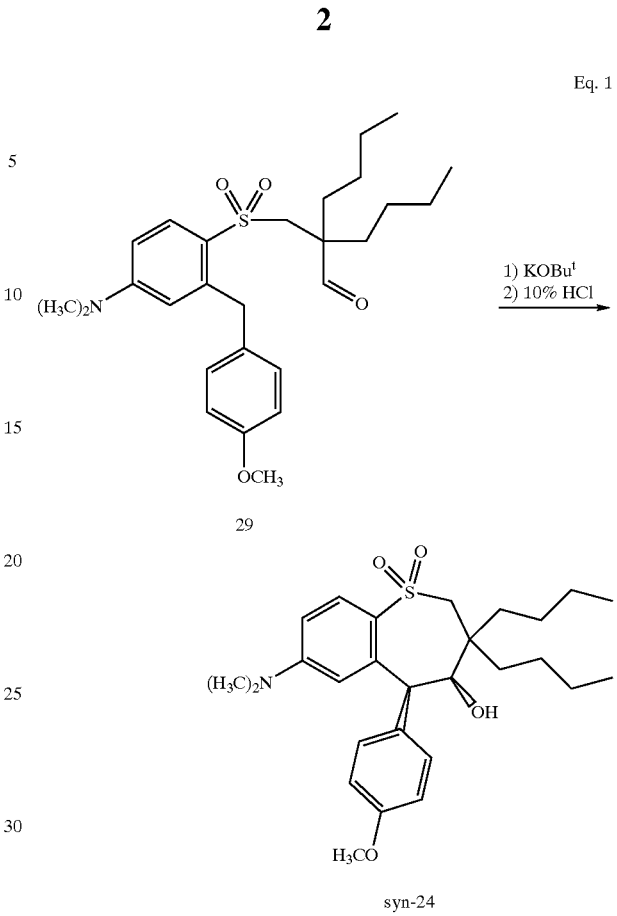

Compound 29 was prepared by reacting 2-chloro-5-nitrobenzoic acid chloride with anisole in the presence of aluminum trichloride to produce a chlorobenzophenone compound; the chlorobenzophenone compound was reduced in the presence of trifluoromethanesulfonic acid and triethylsilane to produce a chlorodiphenylmethane compound; the chlorodiphenylmethane compound was treated with lithium sulfide and 2,2-dibutyl-3-(methanesulfonato)propanal to produce 1-(2,2-dibutyl-3-oxopropylthio)-2-((4-methoxyphenyl)methyl)-4-dimethylaminobenzene (40); and 40 was oxidized with m-chloroperbenzoic acid to produce 29. The first step of that method of preparing compound 29 requires the use of a corrosive and reactive carboxylic acid chloride that was prepared by the reaction of the corresponding carboxylic acid with phosphorus pentachloride.

Phosphorus pentachloride readily hydrolyzes to produce volatile and hazardous hydrogen chloride. The reaction of 2,2-dibutyl-3-(methanesulfonato)propanal with the lithium sulfide and the chlorodiphenylmethane compound required the intermediacy of a cyclic tin compound to make the of 2,2-dibutyl-3-(methanesulfonato)propanal. The tin compound is expensive and creates a toxic waste stream.

In WO 97/33882 compound syn-24 was dealkylated using boron tribromide to produce the phenol compound 28. Boron tribromide is a corrosive and hazardous material that generates hydrogen bromide gas and requires special handling. Upon hydrolysis, boron tribromide also produces borate salts that are costly and time-consuming to separate and dispose of.

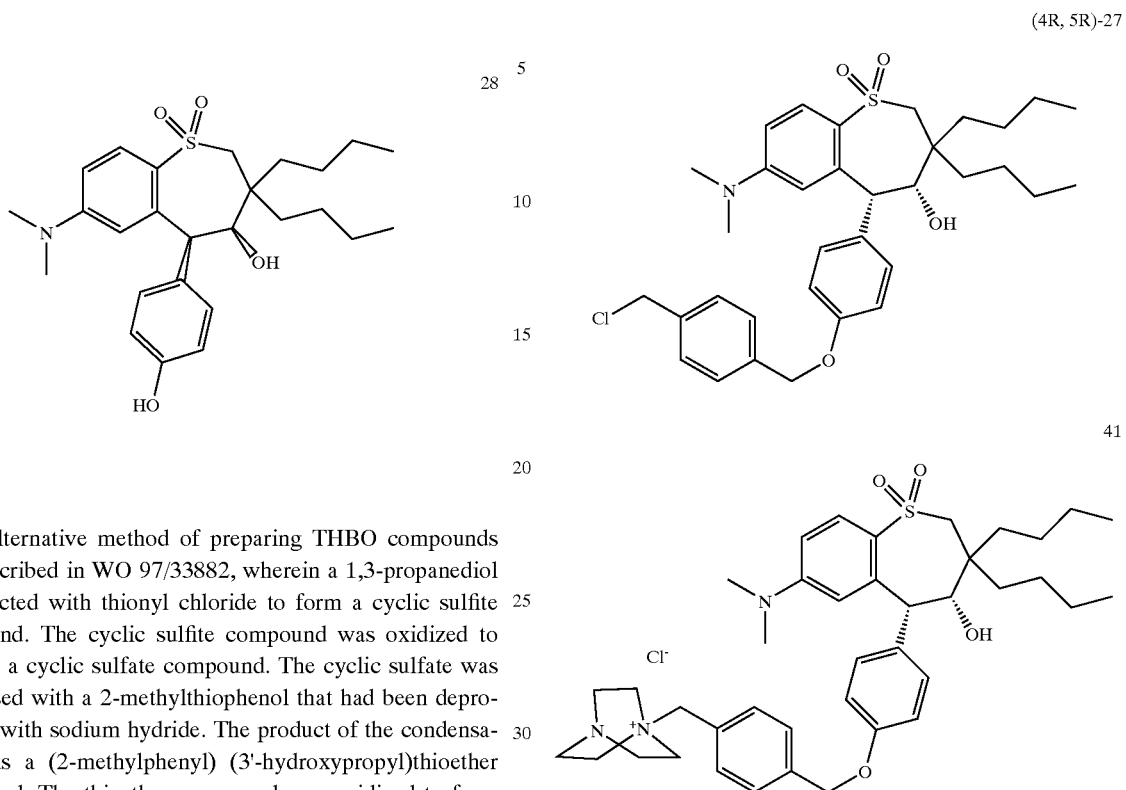

An alternative method of preparing THBO compounds was described in WO 97/33882, wherein a 1,3-propanediol was reacted with thionyl chloride to form a cyclic sulfite compound. The cyclic sulfite compound was oxidized to produce a cyclic sulfate compound. The cyclic sulfate was condensed with a 2-methylthiophenol that had been deprotonated with sodium hydride. The product of the condensation was a (2-methylphenyl) (3'-hydroxypropyl)thioether compound. The thioether compound was oxidized to form an thioether aldehyde compound. The thioether aldehyde compound was further oxidized to form an aldehyde sulfone compound which in turn was cyclized in the presence of potassium t-butoxide to form a 4-hydroxytetrahydrobenzothiepine 1,1-dioxide compound. This cyclic sulfate route to THBO compounds requires an expensive catalyst. Additionally it requires the use of $SOCl_2$, which in turn requires special equipment to handle.

PCT Patent Application No. WO 97/33882 describes a method by which the phenol compound 28 was reacted at its phenol hydroxyl group to attach a variety of functional groups to the molecule, such as a quaternary ammonium group. For example, (4R,5R)-28 was reacted with 1,4-bis (chloromethyl)benzene (?,??'-dichloro-p-xylene) to produce the chloromethyl benzyl ether (4R,5R)-27. Compound (4R, 5R)-27 was treated with diazabicyclo[2.2.2]octane (DABCO) to produce (4R,5R)-1-((4-(4-(3,3-dibutyl-7-(dimethylamino)-2,3,4,5-tetrahydro-4-hydroxy-1,1-dioxido-1-benzothiepin-5-yl)phenoxy)methyl)phenyl) methyl-4-aza-1-azoniabicyclo[2.2.2]octane chloride (41). This method suffers from low yields because of a propensity for two molecules of compound (4R,5R)-28 to react with one molecule of 1,4-bis(chloromethyl)benzene to form a bis(benzothiepine) adduct. Once the bis-adduct forms, the reactive chloromethyl group of compound (4R,5R)-27 is not available to react with an amine to form the quaternary ammonium product.

A method of preparing enantiomerically enriched tetrahydrobenzothiepine oxides is described in PCT Patent Application No. WO 99/32478. In that method, an aryl-3-hydroxypropylsulfide compound was oxidized with an asymmetric oxidizing agent, for example (1R)-(−)-(8,9-dichloro-10-camphorsulfonyl)oxaziridine, to yield a chiral aryl-3-hydroxypropylsulfoxide. Reaction of the aryl-3-hydroxypropylsulfoxide with an oxidizing agent such as sulfur trioxide pyridine complex yielded an aryl-3-propanalsulfoxide. The aryl-3-propanalsulfoxide was cyclized with a base such as potassium t-butoxide to enantioselectively produce a tetrahydrobenzothiepine-1-oxide. The tetrahydrobenzothiepine-1-oxide was further oxidized to produce a tetrahydrobenzothiepine-1,1-dioxide. Although this method could produce tetrahydrobenzothiepine-1,1-dioxide compounds of high enantiomeric purity, it requires the use of an expensive asymmetric oxidizing agent.

Some 5-amidobenzothiepine compounds and methods to make them are described in PCT Patent Application Number WO 92/18462.

In *Synlett,* 9, 943–944(1995) 2-bromophenyl 3-benzoyloxy-1-buten-4-yl sulfone was treated with tributyl tin hydride and AIBN to produce 3-benzoyloxytetrahydrobenzothiepine-1,1-dioxide.

SUMMARY OF THE INVENTION

The ongoing work in the area of tetrahydrobenzothiepine synthesis and the utility of 4-hydroxy-5-phenyltetrahydrobenzothiepine-1,1-dioxide compounds as cholesterol-lowering therapeutics point to the continuing need for economical and practical methods to prepare these compounds.

We now report a novel method for preparing tetrahydrobenzothiepine compounds. Among the several embodiments of the present invention may be noted the provision of an improved process for the preparation of tetrahydrobenzothiepine-1,1-dioxide compounds; the provision of a process for preparing a diastereomeric mixture of tetrahydrobenzothiepine-1,1-dioxide compounds from a single diastereomer of such compounds; the provision of a process for the preparation of 3-bromo-2-substituted propionaldehyde compounds; and the provision of a process for the preparation of 3-thio-2-substituted propionaldehyde compounds.

Briefly, therefore, the present invention is directed to a method for the preparation of a benzylammonium compound having the structure of Formula 60

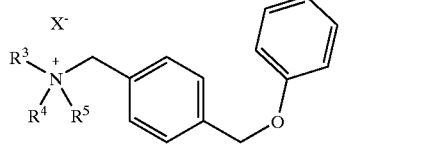

wherein the method comprises treating a benzyl alcohol ether compound having the structure of Formula 61

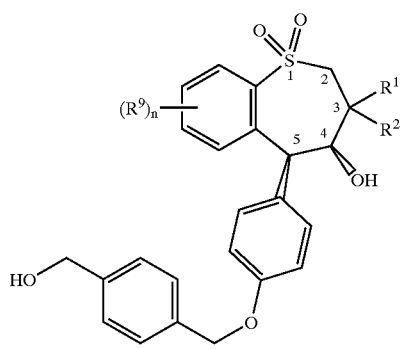

under derivatization conditions to form a derivatized benzyl ether compound having the structure of Formula 62

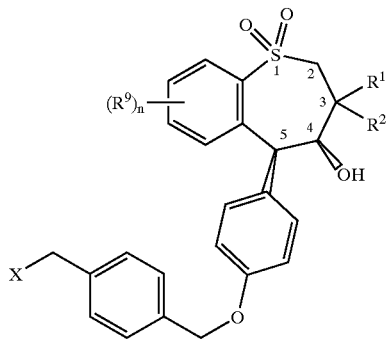

and contacting the derivatized benzyl ether compound with an amine having the structure of Formula 42

under amination conditions thereby producing the benzylammonium compound or a derivative thereof, wherein:

$R^1$ and $R^2$ independently are $C_1$ to about $C_{20}$ hydrocarbyl;

$R^3$, $R^4$, and $R^5$ independently are selected from the group consisting of H and $C_1$ to about $C_{20}$ hydrocarbyl, wherein optionally one or more carbon atom of the hydrocarbyl is replaced by O, N, or S, and wherein optionally two or more of $R^3$, $R^4$, and $R^5$ taken together with the atom to which they are attached form a cyclic structure;

$R^9$ is selected from the group consisting of H, hydrocarbyl, hydroxyalkyl, alkoxyalkyl, aminoalkyl, alkylaminoalkyl, ammoniumalkyl, polyalkoxyalkyl, heterocyclyl, heteroaryl, quaternary heterocycle, quaternary heteroaryl, $OR^3$, $NR^3R^4$, $N^+R^3R^4R^5A^-$, $SR^3$, $S(O)R^3$, $SO_2R^3$, $SO_3R^3$, oxo, $CO_2R^3$, CN, halogen, NCO, $CONR^3R^4$, $SO_2OM$, $SO_2NR^3R^4$, $PO(OR^{23})OR^{24}$, $P^+R^3R^4R^5A^-$, $S^+R^3R^4A^-$, and C(O)OM;

$R^{23}$ and $R^{24}$ are independently selected from the substituents constituting $R^3$ and M;

n is a number from 0 to 4;

$A^-$ is a pharmaceutically acceptable anion and M is a pharmaceutically acceptable cation; and X is a nucleophilic substitution leaving group.

The present invention is also directed to a method for the preparation of a benzylammonium compound having the structure of Formula 1

1

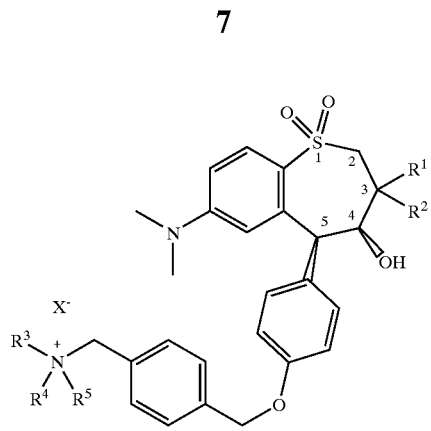

wherein the method comprises treating a benzyl alcohol ether compound having the structure of Formula 6

6

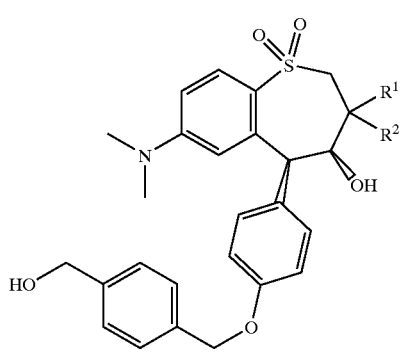

under derivatization conditions to form a derivatized benzyl ether compound having the structure of Formula 2

2

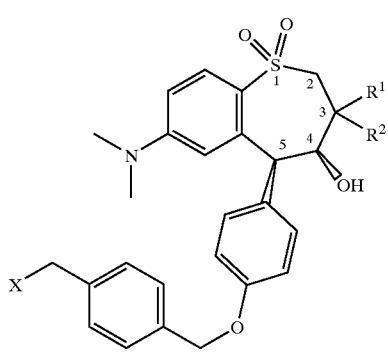

and contacting the derivatized benzyl ether compound with an amine having the structure of Formula 42:

42

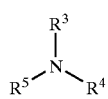

under amination conditions thereby producing the benzylammonium compound or a derivative thereof, wherein $R^1$, $R^2$, $R^3$, $R^4$, $R^5$, and X are defined above.

The invention is further directed to a method for the preparation of a benzylammonium compound having the structure of Formula 1 wherein the method comprises the steps of: treating a protected phenol compound having the structure of Formula 14

14

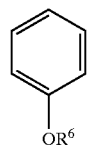

with a substituted benzoyl compound having the structure of Formula 15

15

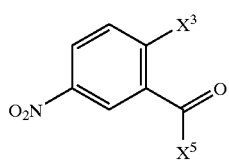

under acylation conditions to produce a substituted benzophenone compound having the structure of Formula 13

13

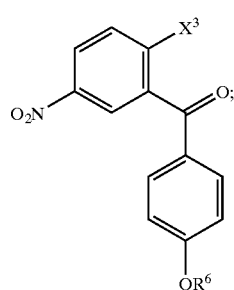

reducing the substituted benzophenone compound to produce a substituted diphenyl methane compound having the structure of Formula 11

11

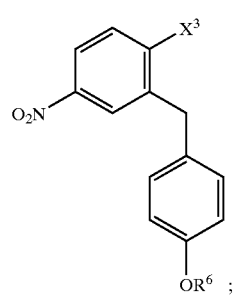

coupling the substituted diphenyl methane compound with a substituted propionaldehyde compound having the structure of Formula 12

12

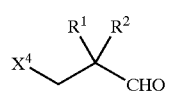

in the presence of a source of sulfur to form a nitro sulfide aldehyde compound having the structure of Formula 10

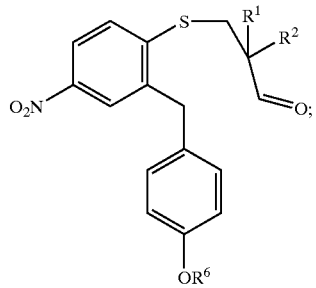

10 oxidizing the nitro sulfide aldehyde compound to form a nitro sulfone aldehyde compound having the structure of Formula 9

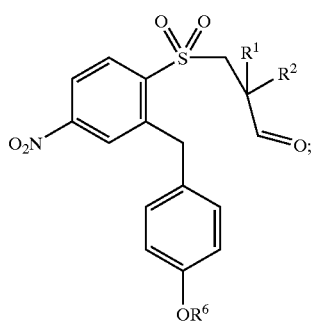

9 reductively alkylating the nitro sulfone aldehyde compound to form an amino sulfone aldehyde compound having the structure of Formula 8

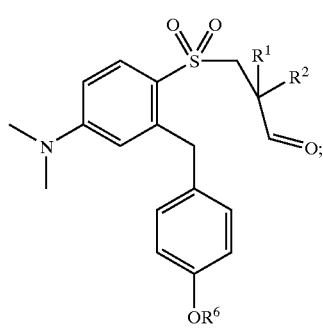

8 treating the amino sulfone aldehyde compound under cyclization conditions to form protected phenol compound having the structure of Formula 7

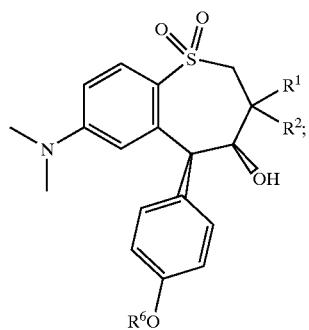

7 deprotecting the protected phenol compound to form a phenol compound having the structure of Formula 4

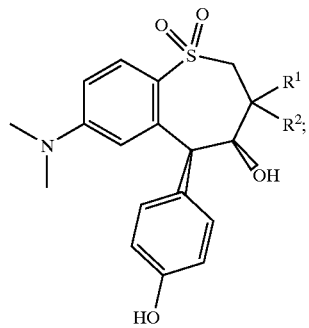

4 coupling the phenol compound with a substituted xylene having the structure of Formula 5

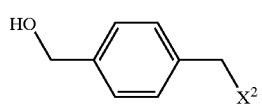

5 under substitution conditions to produce a benzyl alcohol ether compound having the structure of Formula 6 treating the benzyl alcohol ether compound under derivatization conditions to produce a derivatized benzyl ether compound having the structure of Formula 2; and treating the derivatized benzyl ether compound with an amine having the structure of Formula 42 under amination conditions to produce the benzylammonium compound 1; wherein: $R^1$, $R^2$, $R^3$, $R^4$, and $R^5$ are as defined above; R6 is a protecting group, X and $X^4$ independently are nucleophilic substitution leaving groups, $X^2$ is selected from the group consisting of chloro, bromo, iodo, methanesulfonato, toluenesulfonato, benzenesulfonato, and trifluoromethanesulfonato; $X^3$ is an aromatic substitution leaving group; and $X^5$ is selected from the group consisting of hydroxy and halo.

The present invention is also directed to a method for the preparation of a benzylammonium compound having the structure of Formula 1 wherein the method comprises a step in which an acetal compound having the structure of Formula 18

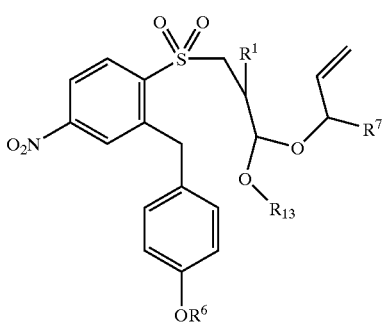

18 is thermolyzed to form an alkenyl sulfone aldehyde compound having the structure of Formula 16

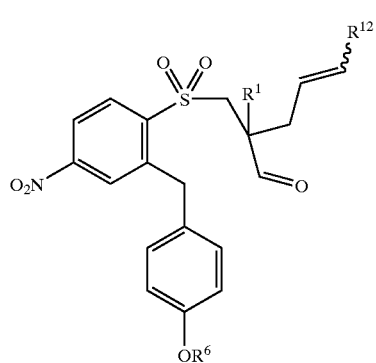

16 wherein $R^1$ and $R^6$ are as defined above; $R^7$ is selected from the group consisting of H and $C_1$ to about $C_{17}$ hydrocarbyl; and $R^{13}$ is selected from the group consisting of H and $C_1$ to about $C_{20}$ hydrocarbyl.

In another embodiment, the present invention is directed to a method of treating a diastereomer of a tetrahydrobenzothiepine compound having the structure of Formula 22

(22)

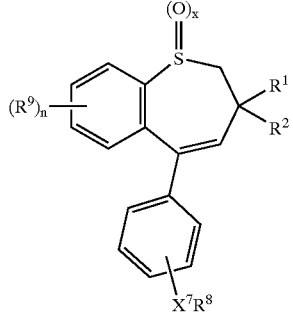

wherein Formula 22 comprises a (4,5)-diastereomer selected from the group consisting of a (4S,5S) diastereomer, a (4R,5R) diastereomer, a (4R,5S) diastereomer, and a (4S,5R) diastereomer, to produce a mixture comprising the (4S,5S) diastereomer and the (4R,5R) diastereomer, wherein the method comprises contacting a base with a feedstock composition comprising the diastereomer of the tetrahydrobenzothiepine compound, thereby producing a mixture of diastereomers of the tetrahydrobenzothiepine compound; and wherein:

$R^8$ is selected from the group consisting of H, hydrocarbyl, heterocycle, ((hydroxyalkyl)aryl)alkyl, ((cycloalkyl)alkylaryl)alkyl, ((heterocycloalkyl)alkylaryl)alkyl, ((quaternary heterocycloalkyl)alkylaryl)alkyl, heteroaryl, quaternary heterocycle, quaternary heteroaryl, and quaternary heteroarylalkyl, wherein hydrocarbyl, heterocycle, heteroaryl, quaternary heterocycle, quaternary heteroaryl, and quaternary heteroarylalkyl optionally have one or more carbons replaced by a moiety selected from the group consisting of O, $NR^3$, $N^+R^3R^4A^-$, S, SO, $SO_2$, $S^+R^3A^-$, $PR^3$, $P^+R^3R^4A^-$, $P(O)R^3$, phenylene, carbohydrate, amino acid, peptide, and polypeptide, and $R^8$ is optionally substituted with one or more moieties selected from the group consisting of sulfoalkyl, quaternary heterocycle, quaternary heteroaryl, $OR^3$, $NR^3R^4$, $N^+R^3R^4R^5A^-$, $SR^3$, $S(O)R^3$, $SO_2R^3$, $SO_3R^3$, oxo, $CO_2R^3$, CN, halogen, $CONR^3R^4$, $SO_2OM$, $SO_2NR^3R^4$, $PO(OR^{23})OR^{24}$, $P^+R^3R^4R^5A^-$, $S^+R^3R^4A^-$, and C(O)OM;

$R^1$, $R^2$, $R^3$, $R^4$, $R^5$, $R^9$, $R^{23}$ and $R^{24}$, n, $A^-$, and M are as defined above;

$X^7$ is S, NH, or O; and x is 1 or 2.

In yet another embodiment, the present invention is directed to a method of treating a diastereomer of a tetrahydrobenzothiepine compound having the structure of Formula (22), wherein the method comprises treating the diastereomer of the tetrahydrobenzothiepine compound under elimination conditions to produce a dihydrobenzothiepine compound having the structure of Formula 23

23

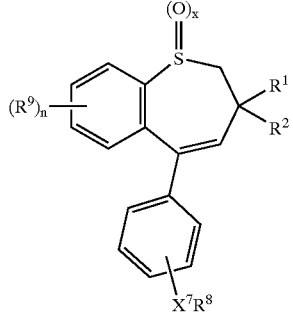

and oxidizing the dihydrobenzothiepine compound to produce the mixture of diastereomers, wherein:

$R^1$, $R^2$, $R^8$, $R^9$, $X^7$, and n are as defined above; and x is 0, 1, or 2.

Another embodiment of the present invention is directed to a method for the preparation of a substituted propionaldehyde compound having the structure of Formula 12 wherein the method comprises oxidizing a substituted propanol compound having the structure of Formula 35

35

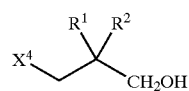

wherein $R^1$ and $R^2$ are as defined above, and $X^4$ is a nucleophilic substitution leaving group.

In another embodiment, the present invention is directed toward a compound having the structure of Formula (2) wherein $R^1$ and $R^2$ independently are $C_1$ to about $C_{20}$ hydrocarbyl and X is selected from the group consisting of Br, I, and a nucleophilic substitution leaving group covalently bonded to the compound via an oxygen atom.

In another embodiment, the present invention provides a crystalline form of a tetrahydrobenzothiepine compound having the structure of Formula 71

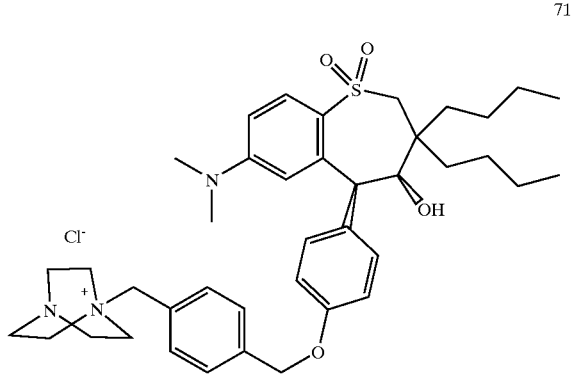

or an enantiomer thereof wherein the crystalline form has a melting point or a decomposition point of about 278° C. to about 285° C.

Another embodiment of the present invention provides a crystalline form of a tetrahydrobenzothiepine compound wherein the tetrahydrobenzothiepine compound has the structure of Formula 71 and which after a sample of the crystalline form is dried at essentially 0% relative humidity at about 25° C. under a purge of essentially dry nitrogen until the sample exhibits essentially no weight change as a function of time, the sample gains less than 1% of its own weight when equilibrated under about 80% relative humidity air at about 25° C. Preferably the crystal form of the present invention comprises a (4R,5R)-enantiomer of compound 71.

Still another embodiment of the present invention provides a crystalline form of a tetrahydrobenzothiepine compound wherein the tetrahydrobenzothiepine compound has the structure of Formula 71 or an enantiomer thereof and wherein the crystalline form is produced by crystallizing the tetrahydrobenzothiepine compound from a solvent comprising methyl ethyl ketone. Preferably the crystal form of the present invention comprises a (4R,5R)-enantiomer of compound 71.

In another embodiment, the present invention provides a method for the preparation of a crystalline form of a tetrahydrobenzothiepine compound having the structure of Formula 63

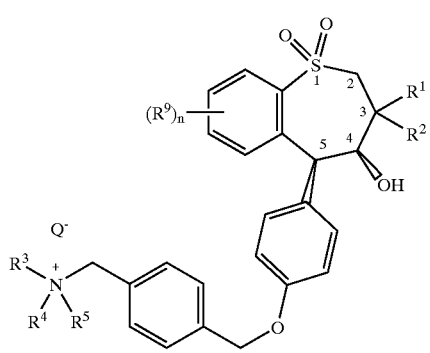

wherein the method comprises crystallizing the tetrahydrobenzothiepine compound from a solvent comprising a ketone (for example methyl ethyl ketone or acetone, preferably methyl ethyl ketone), and wherein $R^1, R^2, R^3, R^4, R^5, R^9$, and n are defined above. In Formula 63 Q$^-$ is a pharmaceutically acceptable anion.

In another embodiment, the present invention provides a method for the preparation of a product crystal form of a tetrahydrobenzothiepine compound having the compound structure of Formula 41 wherein the product crystal form has a melting point or a decomposition point of about 278° C. to about 285° C., wherein the method comprises applying heat to an initial crystal form of the tetrahydrobenzothiepine compound wherein the initial crystal form has a melting point or a decomposition point of about 220° C. to about 235° C., thereby forming the product crystal form.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE FIGURES

FIG. 10 shows water sorption isotherms for Form I (plot (a)) and Form II (plot (b)) of compound 41.

DETAILED DESCRIPTION OF THE PREFERRED EMBODIMENTS

Figure 1:
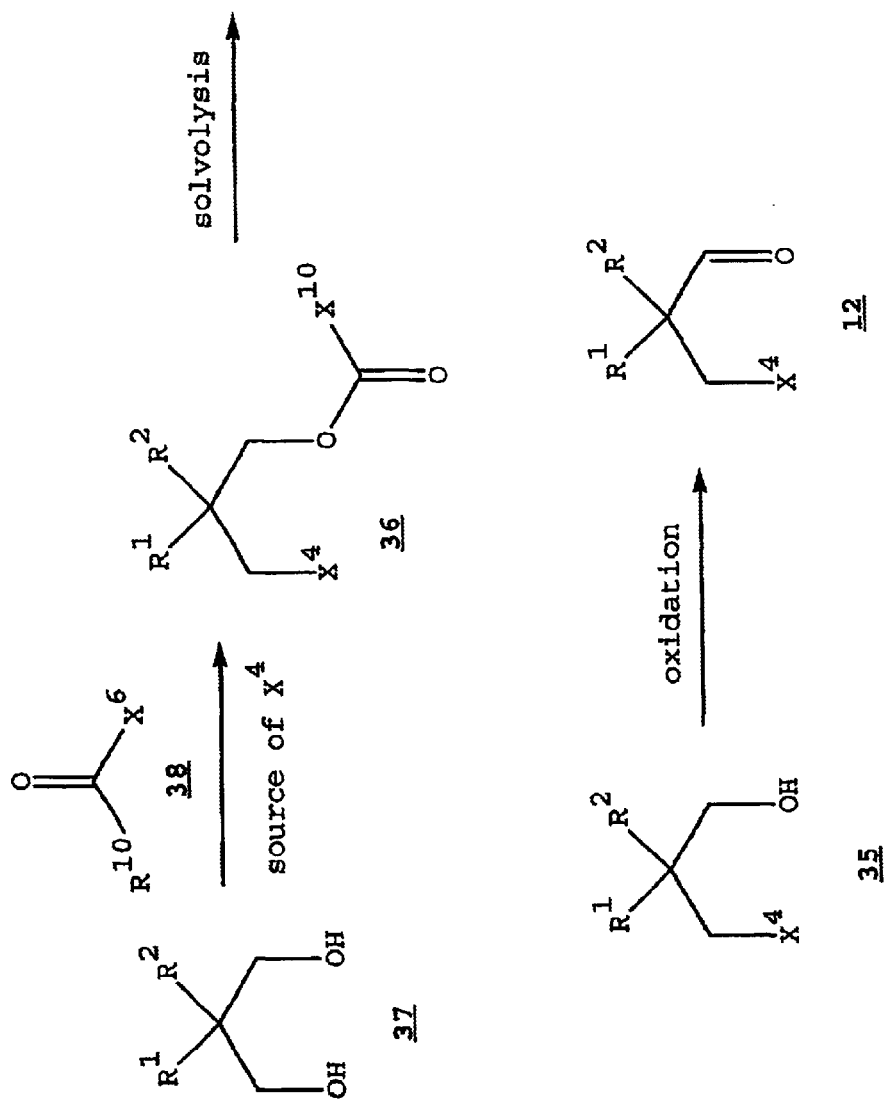
FIG. 1 shows an overall process by which substituted propionaldehyde compound 12 can be prepared.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Hydrocarbyl" means an organic chemical group composed of carbon and hydrogen atoms. Without meaning to limit its definition, the term hydrocarbyl includes alkyl, alkenyl, alkynyl, aryl, cycloalkyl, arylalkyl, alkylarylalkyl, carbocycle, and polyalkyl.

"Alkyl," "alkenyl," and "alkynyl" unless otherwise noted are each straight chain or branched chain hydrocarbon groups of from one to about twenty carbons for alkyl or two to about twenty carbons for alkenyl and alkynyl in the present invention and therefore mean, for example, methyl, ethyl, propyl, butyl, pentyl or hexyl and ethenyl, propenyl, butenyl, pentenyl, or hexenyl and ethynyl, propynyl, butynyl, pentynyl, or hexynyl respectively and isomers thereof.

"Aryl" means a fully unsaturated mono- or multi-ring carbocycle, including, but not limited to, substituted or unsubstituted phenyl, naphthyl, or anthracenyl.

"Heterocycle" means a saturated or unsaturated mono- or multi-ring carbocycle wherein one or more carbon atoms can be replaced by N, S, P, or O. This includes, for example, the following structures:

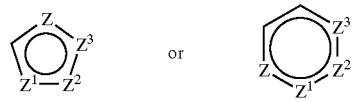

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C.

The term "heteroaryl" means a fully unsaturated heterocycle.

In either "heterocycle" or "heteroaryl," the point of attachment to the molecule of interest can be at the heteroatom or elsewhere within the ring.

The term "quaternary heterocycle" means a heterocycle in which at least one heteroatom, for example, O, N, S, or P, has such a number of bonds that the heteroatom is positively charged. The point of attachment of the quaternary heterocycle to the molecule of interest can be at a heteroatom or elsewhere. The term "quaternary heteroaryl" means a heteroaryl in which at least one heteroatom, for example, O, N, S, or P, has such a number of bonds that the heteroatom is positively charged. The point of attachment of the quaternary heteroaryl to the molecule of interest can be at a heteroatom or elsewhere.

The term "halogen" means a fluoro, chloro, bromo or iodo group.

The term "haloalkyl" means alkyl substituted with one or more halogens.

The term "cycloalkyl" means a mono- or multi-ringed carbocycle wherein each ring contains three to ten carbon atoms, and wherein any ring can contain one or more double or triple bonds. Examples include radicals such as cyclopropyl, cyclobutyl, cyclopentyl, cyclohexyl, cycloalkenyl, and cycloheptyl. The term "cycloalkyl" additionally encompasses spiro systems wherein the cycloalkyl ring has a carbon ring atom in common with the seven-membered heterocyclic ring of the benzothiepine.

The term "oxo" means a doubly bonded oxygen.

The term "polyalkyl" means a branched or straight hydrocarbon chain having a molecular weight up to about 20,000, more preferably up to about 10,000, most preferably up to about 5,000.

The term "arylalkyl" means an aryl-substituted alkyl radical such as benzyl. The term "alkylarylalkyl" means an arylalkyl radical that is substituted on the aryl group with one or more alkyl groups.

The term "heterocyclylalkyl" means an alkyl radical that is substituted with one or more heterocycle groups. Preferable heterocyclylalkyl radicals are "lower heterocyclylalkyl" radicals having one or more heterocycle groups attached to an alkyl radical having one to ten carbon atoms.

The term "heteroarylalkyl" means an alkyl radical that is substituted with one or more heteroaryl groups. Preferable heteroarylalkyl radicals are "lower heteroarylalkyl" radicals having one or more heteroaryl groups attached to an alkyl radical having one to ten carbon atoms.

The term "quaternary heterocyclylalkyl" means an alkyl radical that is substituted with one or more quaternary heterocycle groups. Preferable quaternary heterocyclylalkyl radicals are "lower quaternary heterocyclylalkyl" radicals having one or more quaternary heterocycle groups attached to an alkyl radical having one to ten carbon atoms.

The term "quaternary heteroarylalkyl" means an alkyl radical that is substituted with one or more quaternary heteroaryl groups. Preferable quaternary heteroarylalkyl radicals are "lower quaternary heteroarylalkyl" radicals having one or more quaternary heteroaryl groups attached to an alkyl radical having one to ten carbon atoms.

The term "alkoxy" means a radical comprising an alkyl radical that is bonded to an oxygen atom, such as a methoxy radical. More preferred alkoxy radicals are "lower alkoxy" radicals having one to ten carbon atoms. Examples of such radicals include methoxy, ethoxy, propoxy, isopropoxy, butoxy and tert-butoxy.

The term "carboxy" means the carboxy group, —$CO_2H$, or its salts.

The term "carboalkoxyalkyl" means an alkyl radical that is substituted with one or more alkoxycarbonyl groups. Preferable carboalkoxyalkyl radicals are "lower carboalkoxyalkyl" radicals having one or more alkoxycarbonyl groups attached to an alkyl radical having one to six carbon atoms.

When used in combination, for example "alkylaryl" or "arylalkyl," the individual terms listed above have the meaning indicated above.

As used herein, Me means methyl; Et means ethyl; Pr means propyl; i-Pr or $Pr^i$ each means isopropyl; Bu means butyl; t-Bu or $Bu^t$ each means tert-butyl; Py means pyridine.

The term "derivative" means a compound containing a structural moiety similar to that of another chemical. The term derivative includes, for example, a conjugate acid, a conjugate base, a free base, a free acid, a racemate, a salt, an ester, a compound protected with a protecting group, a tautomer, a stereoisomer, a substituted compound, and a prodrug.

The term "stereoisomer," where a compound has at least one chiral center, includes each enantiomer and each diastereomer. Where a compound has an aliphatic double bond, the term "stereoisomer" includes each cis or Z isomer as well as each trans or E isomer.

In structural drawings, when a chemical bond is represented as an open wedge, such a representation means that the bond can either go into the plane of the page or come out of the plane of the page. When in a structural drawing two or more bonds are represented in the drawing as open wedges (e.g., the structure of Formula 1) the bonds so indicated are in a syn conformation; that is to say all such bonds go into the plane of the page or all such bonds come out of the plane of the page.

In structural drawings, when a chemical bond is represented as a filled-in blackened wedge, such a representation means that the bond is coming out of the plane of the page and represents a specific stereochemistry.

In structural drawings, when a chemical bond is represented as a dashed wedge (e.g., the structure of compound 41), such a representation means that the bond is going into the plane of the page and represents a specific stereochemistry.

In structural drawings, when a chemical bond is represented as a wavy line (e.g., the structure of compound 24), such a representation means that the bond can assume any stereochemistry and can be syn, anti, cis, or trans with any of its neighboring bonds.

b. Process Details

In accordance with the present invention, a process has been discovered for economically preparing a benzylammonium compound having the structure of Formula 1 wherein the method comprises treating a benzyl alcohol ether compound having the structure of Formula 6 under derivatization conditions to form a derivatized benzyl ether compound having the structure of Formula 2 and contacting the derivatized benzyl ether compound with an amine having the structure of Formula 42 under amination conditions thereby producing the benzylammonium compound or a derivative thereof, wherein: $R^1$ and $R^2$ independently are $C_1$ to about $C_{20}$ hydrocarbyl; $R^3$, $R^4$, and $R^5$ independently are selected from the group consisting of H and $C_1$ to about $C_{20}$ hydrocarbyl, wherein optionally one or more carbon atom of the hydrocarbyl is replaced by O, N, or S, and wherein optionally two or more of $R^3$, $R^4$, and $R^5$ taken together with the atom to which they are attached form a cyclic structure; and X is a nucleophilic substitution leaving group. The conversion of compound (6) to compound (1) is shown in Eq. 2.

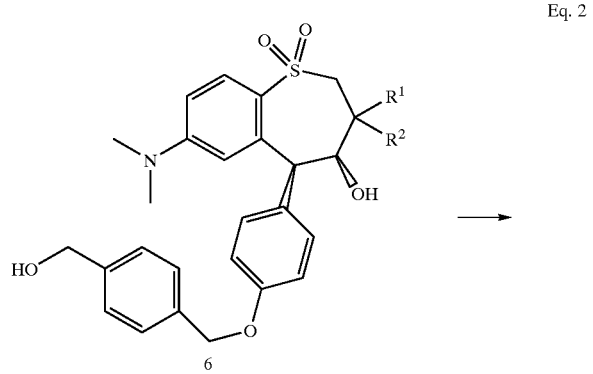

Eq. 2

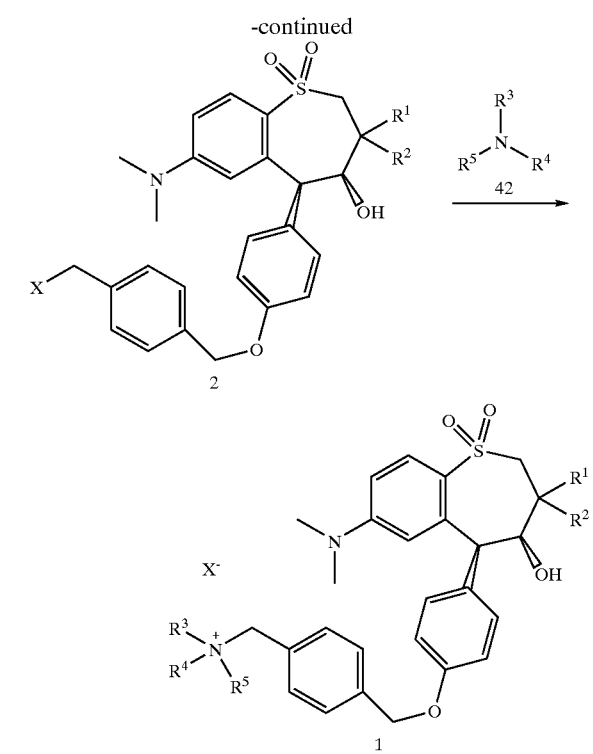

Groups $R^3$, $R^4$, and $R^5$ independently can vary widely in their structures and compositions and remain within the scope of the present invention. In one embodiment, $R^3$, $R^4$, and $R^5$ independently can be H or $C_1$ to about $C_{20}$ hydrocarbyl. Preferably, $R^3$, $R^4$, and $R^5$ independently can be H or $C_1$ to about $C_{10}$ hydrocarbyl; more preferably independently $C_1$ to about $C_{10}$ hydrocarbyl; still more preferably independently $C_1$ to about $C_5$ hydrocarbyl. In a preferred embodiment, $R^3$, $R^4$, and $R^5$ independently can be methyl, ethyl, or propyl. For example, $R^3$, $R^4$, and $R^5$ can each be methyl and the amine of Formula 42 can be trimethylamine. Alternatively, $R^3$, $R^4$, and $R^5$ can each be ethyl and the amine of Formula 42 can be triethylamine.

In another embodiment, the amine of Formula 42 can comprise a heterocycle as its structure or as one of its substructures. The amine can have more than one ring and can comprise, for example, a bicyclic heterocycle. In a preferred embodiment, the amine is 1,4-diazabicyclo[2.2.2]octane (DABCO) and the benzylammonium compound has the structure of Formula 3.

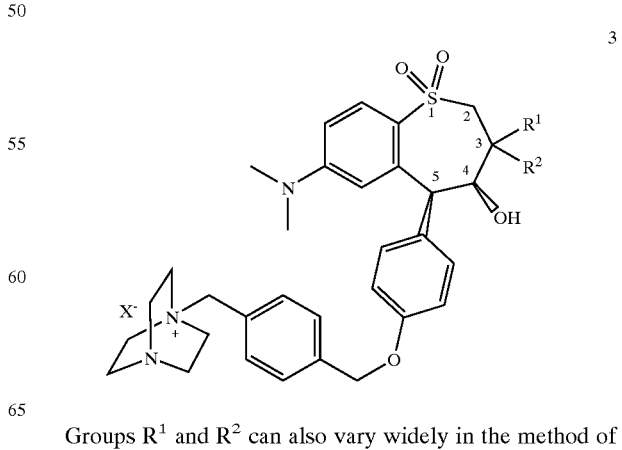

Groups $R^1$ and $R^2$ can also vary widely in the method of the present invention. For example, $R^1$ and $R^2$ independently can be $C_1$ to about $C_{10}$ hydrocarbyl; preferably $R^1$ and $R^2$ are independently $C_1$ to about $C_5$ hydrocarbyl. In one preferred embodiment $R^1$ and $R^2$ are both butyl.

The benzylammonium compound 1 can be an essentially racemic mixture of enantiomers, or one enantiomer can preponderate over another enantiomer. For example, when $R^1$ and $R^2$ are both butyl, compound 1 can be an essentially racemic mixture of enantiomers or compound 1 can comprise a (4R,5R) enantiomer that preponderates over a (4S,5S) enantiomer.

In another preferred embodiment one of $R^1$ and $R^2$ is ethyl and the other of $R^1$ and $R^2$ is butyl. In such a case, compound 1 can be an essentially racemic mixture of enantiomers or compound 1 can comprise a (3R) enantiomer that preponderates over a (3S) enantiomer. Alternatively, compound 1 can comprise a (3S) enantiomer that preponderates over a (3R) enantiomer.

X in the structure of Formula 1 can vary widely and can represent essentially any nucleophilic leaving group that produces either a pharmaceutically acceptable anion or an anion that can be exchanged for a pharmaceutically acceptable anion. In other words, X⁻ is a pharmaceutically acceptable anion or an anion that can be exchanged for a pharmaceutically acceptable anion. For example, X can be chloro, bromo, iodo, methanesulfonato, toluenesulfonato, and trifluoromethanesulfonato. Preferably X is chloro, bromo, or iodo and more preferably X is chloro.

Pharmaceutically acceptable salts are particularly useful as products of the methods of the present invention because of their greater aqueous solubility relative to a corresponding parent or neutral compound. Such salts must have a pharmaceutically acceptable anion or cation. Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic (including carbonate and hydrogen carbonate anions), sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

When compound 1 is formed, it can be used as it is prepared or it can be further processed. For example, anion X⁻ can be exchanged, for example by an ion exchange method such as ion exchange chromatography, for any pharmaceutically acceptable anion.

The amination conditions under which compound 2 and compound 42 react to form benzylammonium compound 1 are robust and can vary widely. For example, the amination can be performed neat without a solvent, or the amination conditions can comprise a solvent. When a solvent is employed, that solvent can have hydrophilic or hydrophobic properties or it can have both hydrophilic and hydrophobic properties. When the solvent comprises a hydrophilic solvent, the hydrophilic solvent can comprise, for example, water; a nitrile such as acetonitrile; an ether such as tetrahydrofuran, diethyl ether, or methyl t-butyl ether; an alcohol such as methanol, ethanol, isopropyl alcohol, or butanol; a ketone such as acetone or methyl ethyl ketone; or an ester such as ethyl acetate. When the solvent comprises a hydrophobic solvent, the hydrophobic solvent can comprise, for example, an aliphatic hydrocarbon solvent such as a $C_1$ to about $C_{20}$ aliphatic hydrocarbon; an aromatic solvent such as benzene, toluene, xylene, or mesitylene; or a halogenated solvent such as methylene chloride, chloroform, carbon tetrachloride, trifluoromethylbenzene, or chlorobenzene. Alternatively, the solvent can comprise a blend of hydrophilic and hydrophobic solvents. In one preferred embodiment the solvent comprises a blend of methyl ethyl ketone and water. In a further preferred embodiment the solvent comprises a blend of methyl ethyl ketone, toluene, and water. Essentially any solvent that is less nucleophilic than compound 42 can be used as a solvent in the amination reaction. Preferably the amination is performed under conditions in which the reagents and product are substantially in homogeneous solution during the majority of the reaction.

The amination can proceed over a wide range of temperatures and preferably is performed within the range of about 0° C. to about 120° C., more preferably about 15° C. to about 110° C., still more preferably about 30° C. to about 100° C., and more preferably still about 45° C. to about 90° C. The amination conveniently can be performed in refluxing solvent such as refluxing methyl ethyl ketone. Preferably, the refluxing in methyl ethyl ketone is performed at ambient pressure.

The derivatization conditions under which benzyl alcohol ether compound 6 is reacted to form a derivatized benzyl ether compound of Formula 2 can comprise essentially any conditions known in the art for converting a benzyl alcohol group into a group that is labile under nucleophilic substitution conditions such as amination conditions. For example, the derivatization conditions can comprise contacting compound 6 with a halogenating agent. Useful halogenating agents include a thionyl halide, a sulfuryl halide, a phosphorus trihalide, a phosphorus pentahalide, an oxalyl halide, and a hydrogen halide. A halogenating agent useful in the present process is preferably a chlorinating agent or a brominating agent, and more preferably a chlorinating agent. For example, the halogenating agent can be thionyl chloride, phosphorus trichloride, phosphorus pentachloride, or hydrogen chloride; preferably the halogenating agent is selected among thionyl chloride, phosphorus trichloride, and phosphorus pentachloride. More preferably the halogenating agent is thionyl chloride. Alternatively, the halogenating agent can comprise a mixture of a phosphine such as triphenylphosphine and a carbon tetrahalide such as carbon tetrachloride. The halogenating agent can be added to the reaction mixture in any form. For example the halogenating agent can be added as a solid or as a liquid (for example as a liquid above the melting point of the halogenating agent or as a solution in a solvent) or the halogenating agent can be contacted with the reaction mixture as a gas under ambient, subambient, or elevated pressure.

When the halogenating agent is thionyl chloride, the halogenation reaction can be performed under a wide variety of conditions. The reaction can be run neat or it can be run in the presence of a solvent. A particularly useful solvent is an aprotic solvent. For example, the solvent can comprise an aromatic solvent, a chlorinated solvent, an ether, an amide, an ester, or a hydrocarbon. Preferred solvents include methylene chloride, chloroform, carbon tetrachloride, chlorobenzene, trifluoromethylbenzene, tetrahydrofuran, diethyl ether, ethyl acetate, and N,N-dimethylacetamide. When the halogenating agent is thionyl chloride, the reaction can be performed at essentially any convenient temperature. Preferably the reaction can run at a temperature of about 0° C. to about 150° C., more preferably about 10° C. to about 125° C., more preferably still about 15° C. to about 100° C., still more preferably about 20° C. to about 75° C., and more preferably yet about 20° C. to about 50° C.

Alternatively, the derivatization conditions under which compound 6 is reacted to form compound 2 can comprise sulfonating the hydroxy group of compound 6 with a sulfonation reagent to form a sulfonated compound, and then treating the sulfonated compound with a source of halide such as a hydrogen halide or a halide salt to form compound 2.

In another embodiment, the derivatization conditions can comprise conditions under which the benzyl hydroxyl group is converted into an oxygen leaving group, for example methanesulfonato, toluenesulfonato, benzenesulfonato, or trifluoromethanesulfonato. Benzyl alcohol ether compound 6 can for example be treated with a sulfonation reagent such as an alkyl sulfonyl halide reagent or an aryl sulfonyl halide reagent. Such alkyl or aryl sulfonyl halide reagents can include a methanesulfonyl halide, a toluenesulfonyl halide, a benzenesulfonyl halide, or a trifluoromethanesulfonyl halide. Preferably the reagent is an alkyl sulfonyl chloride reagent, an aryl sulfonyl chloride reagent, an alkyl sulfonyl bromide reagent, or an aryl sulfonyl bromide reagent. More preferably the sulfonyl halide reagent is a sulfonyl chloride reagent such as methanesulfonyl chloride, toluenesulfonyl chloride, benzenesulfonyl chloride, or trifluoromethanesulfonyl chloride.

In the process of the present invention, the benzyl alcohol ether compound 6 can be used as an essentially racemic mixture of enantiomers or one enantiomer can preponderate over another enantiomer. For example, compound 6 can have a predominantly (4R,5R) absolute configuration or it can have a predominantly (4S,5S) absolute configuration. Alternatively, compound 6 can comprise a blend of (4R,5R) and (4S,5S) absolute configurations.

The preparative method of the present invention can further comprise a step wherein a phenol compound having the structure of Formula 4 is contacted with a substituted xylene compound having the structure of Formula 5 under substitution conditions to produce a benzyl alcohol ether compound having the structure of Formula 6 wherein $X^2$ is a leaving group. Phenol compound 4 can comprise an essentially racemic mixture or it can comprise predominantly an absolute configuration of (4R,5R). Alternatively, compound 4 can comprise predominantly an absolute configuration of (4S,5S). The conversion of compound 4 into compound 6 is shown in Eq. 3.

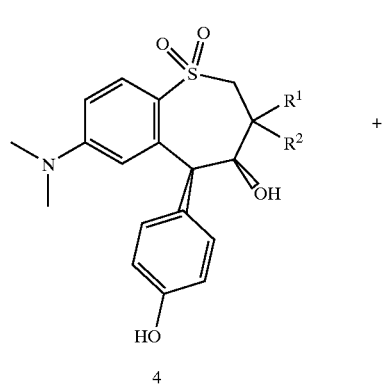

Eq. 3

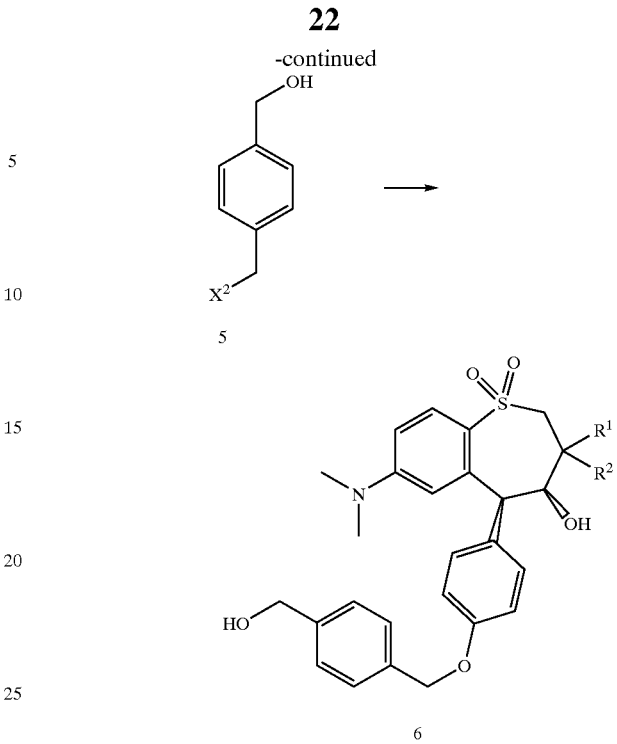

$X^2$ can be essentially any leaving group known in the art for nucleophilic substitution at benzylic carbon. For example, $X^2$ can be halo or a sulfonato group such as methanesulfonato, toluenesulfonato, benzenesulfonato, or trifluoromethanesulfonato. Preferably $X^2$ is halo and more preferably it is chloro, bromo, or iodo. More preferably still $X^2$ is chloro.

The conversion of compound 4 into compound 6 can be performed, if desired, in the presence of a solvent. Essentially any solvent that dissolves to some extent the reactants and that is primarily non-reactive toward the reactants will be useful. For example, the solvent can comprise an aromatic solvent, an amide, an ester, a ketone, an ether or a sulfoxide. Preferably, the solvent is an aprotic solvent such as N-methylpyrrolidone, dimethyl sulfoxide, tetrahydrofuran, or an amide solvent. Preferably the solvent is an amide solvent. More preferably the amide is selected from the group consisting of dimethylformamide and dimethylacetamide; and still more preferably the solvent is N,N-dimethylacetamide (DMAC).

The conversion of compound 4 into compound 6 can further be performed in the presence of a base. Useful bases include a metal hydroxide, a metal alcoholate, a metal hydride, an alkyl metal complex, a metal carbonate, and an amide base. Preferably the base comprises a metal hydroxide such as sodium hydroxide, potassium hydroxide, lithium hydroxide, or calcium hydroxide. More preferably the base is sodium hydroxide. When the base is a metal carbonate, preferably it is an alkali metal carbonate or an alkaline earth metal carbonate. For example the base can be potassium carbonate.

The preparative method of the present invention can further comprise a deprotecting step wherein a protected phenol compound having the structure of Formula 7

Eq. 4

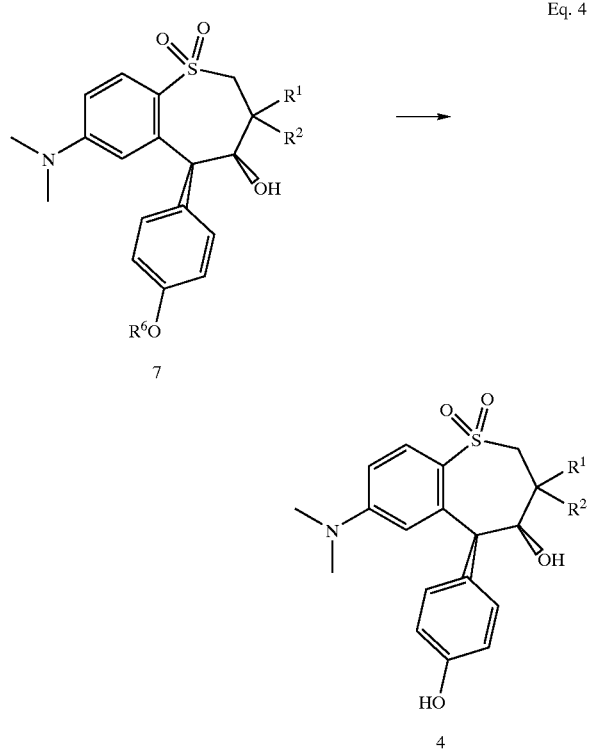

7

4 is deprotected to form the phenol compound 4, wherein $R^6$ is a protecting group. The conversion of compound 7 into compound 4 is shown in Eq. 4. A protecting group is any chemical group that temporarily blocks a reactive site in a molecule while a chemical reaction is selectively performed at another reactive site in the same molecule or at a reactive site in another molecule residing in the same reaction mixture as the protected molecule. Many protecting groups described by Greene and Wuts (*Protective Groups in Organic Synthesis*, 3d ed., John Wiley & Sons, Inc., New York, 1999, pp. 249–287, herein incorporated by reference) are useful for protecting the phenol functional group in the process of the present invention. For example, $R^6$ can be a hydrocarbyl group such as a methyl group, an isopropyl group, a t-butyl group, a cyclohexyl group, or a benzyl group; an alkoxymethyl group such as a methoxymethyl group or a benzyloxymethyl group; an alkylthiomethyl group such as a methylthiomethyl group; a silyl group such as a trimethylsilyl group; an acyl group such as a formyl group, an acetyl group, or a benzoyl group; a carbonate group such as a methyl carbonate group; a phosphinate group; or a sulfonate group. In one embodiment, $R^6$ is a $C_1$ to about $C_{10}$ hydrocarbyl group, preferably a $C_1$ to about $C_{10}$ alkyl group, more preferably a $C_1$ to about $C_5$ alkyl group, and still more preferably methyl.

When $R^6$ is a methyl group, a wide variety of conditions can be used in the deprotecting step. For example the conditions of the deprotecting step can comprise treating compound 7 with a deprotecting reagent. Without limitation, useful deprotecting reagents include a halotrimethylsilane such as iodotrimethylsilane; an alkali metal such as lithium or sodium in combination with 18-crown-6; an alkali metal sulfide such as sodium sulfide or lithium sulfide; an alkali metal halide such as lithium iodide; an aluminum trihalide such as aluminum tribromide; an aluminum trihalide and an alkylthiol such as ethanethiol; a strong acid in combination with a source of nucleophilic sulfur; a boron trihalide such as boron tribromide or boron trichloride; a hydrogen halide such as hydrogen iodide, hydrogen bromide, or hydrogen iodide; or a metal hydrocarbyl thiolate. When the deprotecting reagent comprises a boron trihalide, preferably it comprises boron tribromide. When the deprotecting reagent is a metal hydrocarbyl thiolate, preferably it is a lithium hydrocarbyl thiolate, more preferably a lithium $C_1$ to about $C_{10}$ alkyl thiolate, and more preferably still lithium ethanethiolate. When the deprotecting reagent is a strong acid in combination with a source of nucleophilic sulfur, preferably the strong acid can for example be sulfuric acid, a sulfonic acid, a Lewis acid, or a phosphorus oxy acid. Preferably the strong acid is sulfuric acid or a sulfonic acid, and more preferably a sulfonic acid. When the strong acid is a sulfonic acid, preferably it is methanesulfonic acid, trifluoromethanesulfonic acid, benzenesulfonic acid, or toluenesulfonic acid; more preferably the strong acid is methanesulfonic acid. The source of nucleophilic sulfur can, for example, be methionine.

In the method of the present invention, compound 7 can be a racemic compound or it can be used as a mixture of stereoisomers or it can be used as predominantly one of its stereoisomers. Preferably compound 7 has an absolute configuration of (4R,5R). Alternatively, compound 7 can have an absolute configuration of (4S,5S).

When the deprotecting reagent is a sulfonic acid in combination with methionine, a variety of conditions can be employed in the deprotecting step of the present method. The reaction can be run substantially neat (substantially without added solvent), or a solvent can be added. Essentially any solvent that dissolves the reagents and that is mostly unreactive toward the reagents would be useful in this reaction. Useful solvents include a hydrocarbon solvent such as an alkane, an aromatic solvent such as benzene or toluene; a chlorinated solvent such as methylene chloride, chloroform, carbon tetrachloride, chlorobenzene, or trifluoromethylbenzene; and inorganic solvents such as $SO_2$.

The deprotecting step can be performed over a wide range of temperatures. Preferably the temperature is in the range of about 0° C. to about 150° C., more preferably about 25° C. to about 130° C., still more preferably about 50° C. to about 110° C., and more preferably still about 65° C. to about 100° C.

In another embodiment, the method of the present invention can further comprise a cyclization step wherein an amino sulfur oxide aldehyde compound having the structure of Formula 8a is treated under cyclization conditions to form a protected phenol compound having the structure of Formula 7a wherein $R^1$, $R^2$, and $R^6$ are defined above, and y is 1 or 2. The cyclization of 8a into 7a is shown in Eq. 5.

Eq. 5

8a

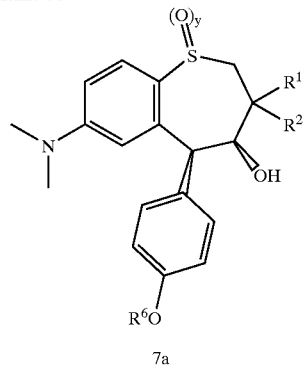

7a

The cyclization can be mediated by conditions that comprise treating the amino sulfur oxide aldehyde with a base. Useful bases in this reaction include $MOR^{11}$, a metal hydroxide, or an alkyl metal complex, wherein $R^{11}$ is a $C_1$ to about $C_{10}$ hydrocarbyl group and M is an alkali metal. Preferably the base is $MOR^{11}$. When the base is $MOR^{11}$, M is preferably lithium or potassium. In a particularly useful embodiment $R^{11}$ is a $C_1$ to about $C_{10}$ alkyl group, preferably a $C_1$ to about $C_5$ alkyl group, more preferably $R^{11}$ is methyl, ethyl, isopropyl, or tert-butyl, and still more preferably $R^{11}$ is tert-butyl.

The conditions of the cyclization step can comprise a solvent. The solvent can be a hydrophilic solvent and preferably it is a hydrophilic aprotic solvent. The solvent can be, for example, a cyclic or acyclic ether such as tetrahydrofuran, diethyl ether, methyl tert-butyl ether, 1,4-dioxane, glyme, or diglyme. Preferably the solvent is tetrahydrofuran. Alternatively, the solvent can be an alcohol such as methanol, ethanol, propanol, isopropyl alcohol, butanol, sec-butyl alcohol, isobutyl alcohol, or t-butyl alcohol.

The cyclization step can be performed at various temperatures. Preferably the step is performed at a temperature of about −20° C. to about 50° C., preferably about −10° C. to about 35° C., and more preferably about 0° C. to about 25° C.

When y is 1, the present method can further comprise an oxidation step to convert the amino sulfoxide aldehyde (8a where y=1) to the amino sulfone aldehyde (8a where y=2). For example, the oxidation step can comprise treating the amino sulfoxide aldehyde with sodium hypochlorite. Alternatively, the amino sulfoxide aldehyde can be treated with hydrogen peroxide, preferably in the presence of imidazole and tetraphenylporphyrin Fe(III) chloride. In another alternative, the amino sulfoxide aldehyde can be treated with hydrogen peroxide in the presence of methyltrioxorhenium. The conversion of the amino sulfoxide aldehyde to the sulfone will also be achieved by treating the sulfoxide with hydrogen peroxide in the presence of acetonitrile and a base such as potassium carbonate. Another useful oxidation will comprise treating the amino sulfoxide aldehyde with cobalt diacetonylacetonate $(Co(acac)_2)$ in the presence of $O_2$ and, for example, isovaleraldehyde. Still another useful oxidation will comprise treating the amino sulfoxide aldehyde with 2-methylpropanal in the presence of $O_2$. Alternatively, the oxidation will be performed by treating the amino sulfoxide aldehyde with silica gel in the presence of t-butyl hydroperoxide. The conversion will also occur when the amino sulfoxide aldehyde is treated with periodic acid in the presence, for example, of ruthenium trichloride hydrate. Alternate conditions for the oxidation can comprise treating the amino sulfoxide aldehyde with urea and phthalic anhydride in the presence of hydrogen peroxide. In another example the oxidation of the amino sulfoxide aldehyde will be carried out by treatment with Oxone monopersulfate compound (2 $KHSO_5$. $KHSO_4$. $K_2SO_4$) in the presence of silica gel or wet montmorillonite clay.

Preferably y is 2 during the cyclization step.

In still another embodiment, the method of the present invention can further comprise an reductive alkylation step in which a nitro sulfur oxide aldehyde compound having the structure of Formula 9a is reductively alkylated to form the amino sulfur oxide aldehyde compound 8b wherein $R^1$, $R^2$, and $R^6$ are defined above, and z is 0, 1, or 2. Preferably z is 2. The conditions under which compound 9a is reductively alkylated can include, for example, contacting 9a with a source of formaldehyde and a source of $H_2$ in the presence of a catalyst. The reductive alkylation is preferably performed at elevated $H_2$ pressure. It is useful to perform the reductive alkylation at $H_2$ pressures ranging from about 100 to about 700,000 kPa, preferably from about 200 to about 300,000 kPa, more preferably from about 300 to about 100,000 kPa, still more preferably from about 350 to about 10,000 kPa, and more preferably still from about 400 to about 1000 kPa. The conversion of compound 9a into compound 8b is shown in Eq. 6.

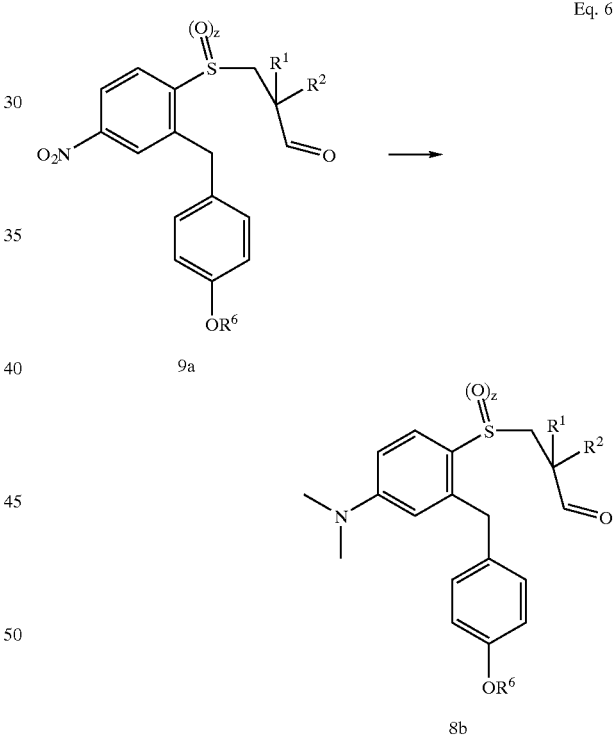

Eq. 6

9a

8b

The reductive alkylation described herein can, if preferred, be performed on an acetal derivative of compound 9a as shown in Eq. 8b.

The source of formaldehyde can be essentially any source that produces the equivalent of $CH_2O$. For example, the source of formaldehyde can be formalin, dimethoxymethane, paraformaldehyde, trioxane, or any polymer of $CH_2O$. Conveniently the source of formaldehyde can be formalin, and preferably about 30% to about 37% formalin.

The catalyst for the reductive alkylation can be either a heterogeneous catalyst or a homogeneous catalyst. Preferably the catalyst is a metal, for example be a noble metal catalyst. Useful noble metal catalysts include Pt, Pd, Ru, and Rh. Preferably the noble metal catalyst is a Pd catalyst. Alternatively, the metal catalyst can be a nickel catalyst, for example a high-surface area nickel catalyst such as Raney nickel. The catalyst can be a homogeneous catalyst or it can be a heterogeneous catalyst, preferably a heterogeneous catalyst. When the catalyst is a noble metal catalyst, it can be used either as the metal per se or the metal can be used in combination with a solid support such as carbon. Alternatively, the metal catalyst can be used in combination with another metal such as an anchor metal or a promoter metal. In a particularly preferred embodiment, the catalyst comprises Pd on carbon.

An acid can be present in the reaction mixture during the reductive alkylation. Preferably the acid is a strong acid and more preferably a strong mineral acid. For example, the acid can be sulfuric acid.

The reaction mixture can conveniently comprise a solvent during the reductive alkylation. Useful solvents include an alcohol, an aromatic solvent, an ether solvent, and a halogenated solvent such as a halogenated aromatic solvent. Preferably the solvent is an alcohol solvent such as ethanol.

The reductive alkylation reaction can be run at any convenient temperature, for example from about 0° C. to about 200° C., preferably from about 10° C. to about 150° C., more preferably from about 15° C. to about 125° C., still more preferably from about 20° C. to about 100° C., more preferably still from about 25° C. to about 80° C., and more preferably yet from about 30° C. to about 75° C.

The reductive alkylation can alternatively be performed in two steps. For example, in a first step the nitro group of compound 9a can be reduced to an amino group and then the amino group can be methylated. For example, nitro sulfur oxide aldehyde compound 9a can be reduced to form an aniline sulfur oxide compound having the structure of Formula 39

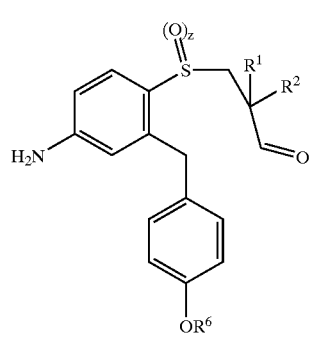

39 wherein $R^1$, $R^2$, $R^6$ and z are as defined above. The method can further comprise a methylation step in which the aniline sulfur oxide compound is treated under methylation conditions to form the amino sulfur oxide aldehyde compound 8a. The reduction of the nitro group to an amino group can be achieved, for example, by catalytic hydrogenation. The catalytic hydrogenation to form compound 39 will be achieved, for example by contacting compound 9a with $H_2$ in the presence of a hydrogenation catalyst. A useful hydrogenation catalyst will be, for example, a palladium catalyst such as palladium on carbon (Pd/C). It will be useful to perform the hydrogenation at $H_2$ pressures ranging from about 100 to about 700,000 kPa, preferably from about 200 to about 300,000 kpa, more preferably from about 300 to about 100,000 kPa, still more preferably from about 350 to about 10,000 kPa, and more preferably still from about 400 to about 1000 kPa. The methylation step can be carried out under a wide variety of methylation conditions. Alternatively, the reduction of 9a to form 39 can be performed under other reduction conditions such as treatment of 9a with iron in the presence of acetic acid or treatment of 9a with tin in the presence of hydrochloric acid.

The methylation conditions can comprise, for example, treating compound 39 with a methylating reagent such as a methyl halide or a methyl sulfonate. Useful methyl halides include methyl chloride, methyl bromide, and methyl iodide. Useful methyl sulfonates include methyl methanesulfonate, methyl toluenesulfonate, methyl benzenesulfonate, and methyl trifluoromethylsulfonate. Alternatively, the methylation conditions can comprise treating compound 39 with a source of formaldehyde in the presence of $H_2$ and a hydrogenation catalyst. Conditions useful for the reductive alkylation of compound 9a to compound 8b are also useful for the methylation of compound 39.

In another embodiment, the method of the present invention can further comprise an oxidation step in which a nitro sulfide aldehyde compound having the structure of Formula 10 is oxidized to form compound 9a wherein $R^6$ is a protecting group and z is 1 or 2. Preferably, compound 10 is treated under oxidation conditions to form a nitro sulfone aldehyde compound of Formula 9. The oxidation reaction can be carried out by treating 10 with an oxidizing agent. Useful oxidizing agents include, for example, a peracid, an alkyl hydroperoxide, or hydrogen peroxide. When the oxidizing agent is a peracid, it can conveniently be, for example, peracetic acid or m-chloroperbenzoic acid. Preferably the oxidizing agent comprises peracetic acid. The conversion of compound 10 to compound 9a is shown in Eq. 7.

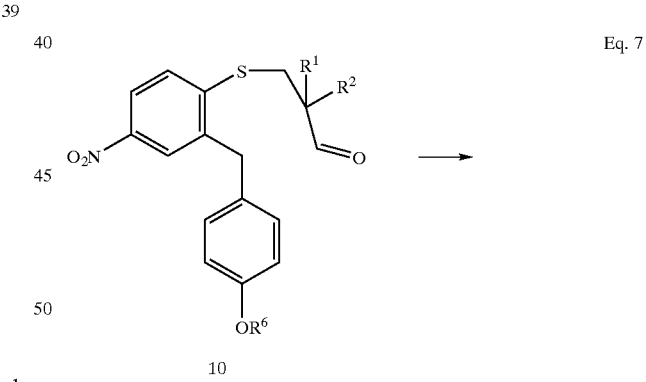

10

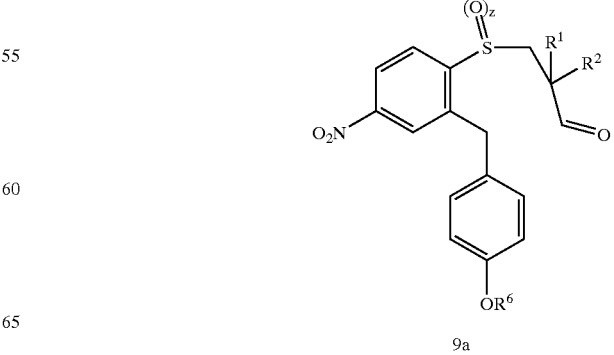

9a

Eq. 7

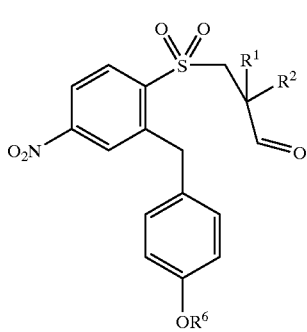

9

The method of the present invention can also further comprise a step in which compound 9a where z is 1 is oxidized to sulfone compound 2. Such an oxidation can be performed by treating 9a where z is 1 with for example, a peracid, an alkyl hydroperoxide, or hydrogen peroxide.

During the oxidation step of Eq. 8 it is convenient to protect the aldehyde functional group of compound 10 from oxidation, for example to prevent the formation of the corresponding carboxylic acid. A variety of protecting groups are known in the art for protecting aldehydes from being oxidized to carboxylic acids and such protecting groups can be employed in the method of the present invention. Numerous methods of protecting aldehydes are described by Greene and Wuts (*Protective Groups in Organic Synthesis*, 3d ed., John Wiley & Sons, Inc., New York, 1999, pp. 297–368, herein incorporated by reference) are useful herein. For example, the aldehyde group of compound 10 can be protected as an acetal such as a dimethyl acetal or a diethyl acetal. Essentially any of the acetal-forming methods described by Greene and Wuts are useful in the present invention. It is convenient to protect the aldehyde group of 10 as a dimethyl acetal by contacting 10 with trimethyl orthoformate, an acid such as p-toluenesulfonic acid, and methanol. Conveniently, 10 can be contacted with trimethyl orthoformate, the acid, and methanol in the presence of a solvent. A useful solvent is benzotrifluoride (BTF). After the oxidation step, the aldehyde group can be deprotected by methods known in the art. For example, the dimethyl acetal can be converted to the aldehyde by treatment with water and an acid such as sulfuric acid or hydrochloric acid.

Alternatively, the method of the present invention can comprise an oxidation step in which the conditions comprise enantioselective oxidation conditions. Such enantioselective oxidation conditions are described in PCT Patent Application No. WO 99/32478, herein incorporated by reference. For example, nitro sulfide aldehyde compound 10 can be enantioselectively oxidized to a chiral nitro sulfoxide aldehyde compound (9a where z is 1). Ring closure of the chiral nitro sulfoxide aldehyde compound by treatment with base (for example a metal alkoxide such as potassium t-butoxide) will form selectively one enantiomer or set of diastereomers of the tetrahydrobenzothiepine-1-oxide compound that can be further oxidized selectively to predominantly one enantiomer or selectively to a set of diastereomers of the tetrahydrobenzothiepine-1,1-dioxide.

The method of the present invention can further comprise a sulfide-forming step in which a substituted diphenyl methane compound having the structure of Formula 11 is coupled with a substituted propionaldehyde equivalent compound having the structure of Formula 12a in the presence of a source of sulfur to form the nitro sulfide aldehyde compound 10 wherein $R^1$, $R^2$, and $R^6$ are defined above; $R^{27}$ is an aldehyde group (—CHO) or a protected aldehyde group such as an acetal; $X^3$ is an aromatic substitution leaving group; and $X^4$ is a nucleophilic substitution leaving group. This overall sulfide-forming step is shown in Eq. 8.

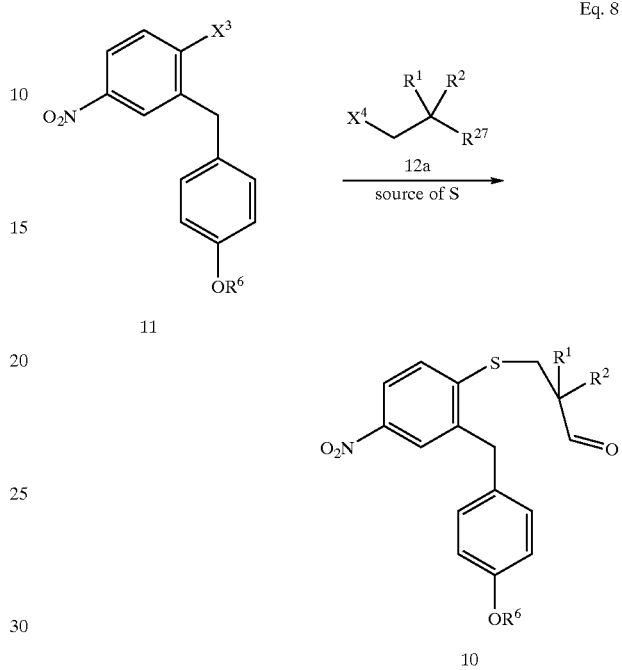

Where $R^{27}$ is an aldehyde group, compound 12a has the structure of Formula 12.

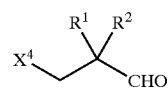

(12)

In the reaction of Eq. 8, it is also possible for $R^{27}$ to be —$CH_2OH$ (or a protected alcohol) or —$CO_2H$ (or a protected carboxylic acid). Where $R^{27}$ is —$CH_2OH$ (or a protected alcohol), the addition of compound 12a can conveniently be followed by an oxidation step in which the alcohol function is oxidized to an aldehyde or carboxylic acid function. Where $R^{27}$ is —$CO_2H$ (or a protected carboxylic acid), the addition of compound 12a can conveniently be followed by a reduction step. Alternatively, where $R^{27}$ is —$CO_2H$ (or a protected carboxylic acid), the addition of compound 12a can be followed by a cyclization step and/or a sulfur oxidation step to form a cyclic ketone that can be reduced to alcohol 7a.

The source of sulfur can be, for example, a metal sulfide such as lithium sulfide ($Li_2S$), sodium sulfide ($Na_2S$), or $Na_2S_2$. Preferably the source of sulfur is $Na_2S$ or $Li_2S$, and more preferably $Na_2S$. $X^3$ can be essentially any convenient aromatic substitution leaving group. For example, $X^3$ can be a halogen, a sulfonato group, or a nitro group. Preferably $X^3$ is a halogen, more preferably Cl or Br, and still more preferably Cl. When $X^3$ is a sulfonato group, it can be, for example, methanesulfonato, trifluoromethanesulfonato, benzenesulfonato, or toluenesulfonato; preferably $X^3$ is trifluoromethane-sulfonato. When $X^3$ is a sulfonato group, the sulfide-forming reaction is preferably carried out in the presence of a noble metal such as Pd(0) and a metal sulfide.

$X^4$ can be essentially any nucleophilic substitution leaving group that, when displaced, produces an anion that is chemically and physically compatible with the reaction conditions. For example, $X^4$ can be chloro, bromo, iodo, methanesulfonato, toluenesulfonato, and trifluoromethanesulfonato. Preferably $X^4$ is chloro, bromo, or iodo and more preferably $X^4$ is bromo.

In the sulfide-forming step of the present reaction, it is preferred that diphenylmethane compound 11 be contacted with the source of sulfur to form the intermediate thiolate anion 44 before being contacted with the substituted propionaldehyde compound 12.

Alternatively, the addition of the source of sulfur and the reaction with the substituted propionaldehyde compound 12 can be performed in one reaction vessel or in one reaction mixture without isolation of intermediate structures.

Alternatively, the sulfide-forming step can be performed following the reaction of Eq. 8a, wherein diphenylmethane compound 11 is contacted under coupling conditions described above with a thiopropyl compound 12b to form sulfide 10a. In Eq. 8a, $R^1$, $R^2$, $R^6$, $R^{27}$, and $X^3$ are as defined above and $R^{28}$ is H or a labile thiol protecting group such as an acyl group, preferably an acetyl group.

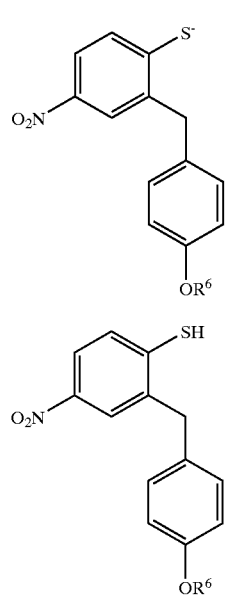

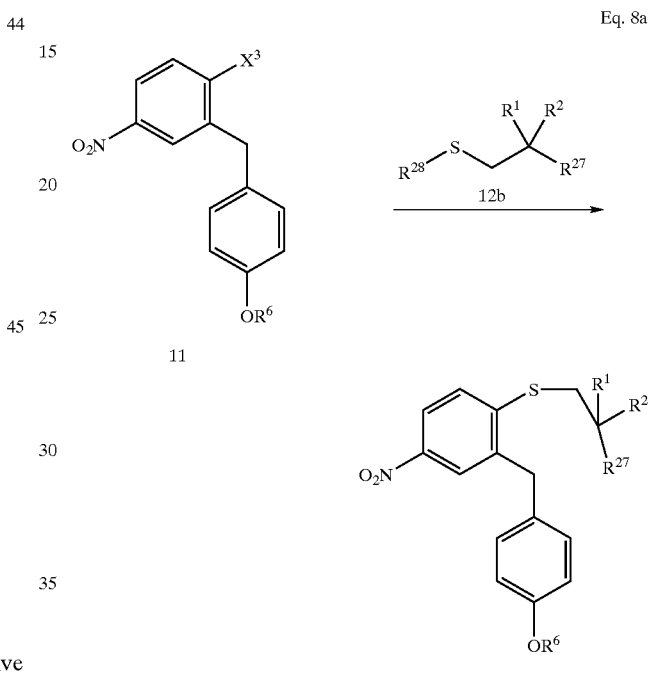

Eq. 8a

In the sulfide-forming step of the present inventive method, the contacting of the source of sulfur with compound 11 can be done at any convenient temperature. Preferably the contacting is performed at a temperature in the range of about 0° C. to about 150° C., more preferably about 0° C. to about 100° C., still more preferably about 10° C. to about 75° C., still more preferably about 20° C. to about 50° C., and more preferably yet around 25° C. to about 45° C. It is helpful to allow the source of sulfur, for example sodium sulfide, to contact compound 11 for a period of reaction time before adding substituted propionaldehyde compound 12 to the mixture. Appropriately, the reaction time can be about 5 minutes to about ten hours, preferably about 10 minutes to about 7 hours, more preferably about 20 minutes to about 5 hours, and more preferably still about 30 minutes to about 3 hours.

Optionally, anion 44 can be quenched, for example with water or with an acid, to form thiol compound 45. Thiol 45 can be isolated, stored, transported, or kept in a solution until used. When ready to use thiol 45 to prepare compound 10 thiol 45 can be treated with a suitable base such as a metal alkoxide, a metal hydride, an alkyl metal complex, or other base to form anion 44. Suitable bases include, for example, an alkali metal alkoxide such as sodium methoxide, lithium methoxide, sodium ethoxide, lithium ethoxide, and potassium t-butoxide. Useful metal hydrides include sodium hydride and calcium hydride.

However, it is preferred not to quench anion 44 or to isolate thiol compound 45. Anion 44 is sufficiently stable to store or transport without quenching.

The reaction of Eq. 8a can conveniently be performed in the presence of a base. Useful bases include an alkali metal base or an alkaline earth metal base. Useful alkali metal bases include alkali metal hydroxides such as sodium hydroxide or potassium hydroxide. Conveniently, the reaction of Eq. 8a can be performed in the presence of a solvent, preferably an aprotic solvent, and more preferably a polar aprotic solvent. A preferred solvent for the reaction of Eq. 8a is DMSO.

Conveniently, the sulfide-forming step of Eq. 8a can be performed in the presence of a solvent. Useful solvents include polar aprotic solvents. Without limitation, useful polar aprotic solvents include N,N-dimethylacetamide (DMAC), dimethylsulfoxide (DMSO), dimethylformamide (DMF), and N-methylpyrrolidone (NMP). Preferably the solvent is DMAC.

Where $R^{27}$ of Eq. 8a is a protected aldehyde group such as an acetal group, compound 10a can be further reacted to deprotect the protected acetal group, if desired. Alternatively, compound 10a can be directly oxidized under sulfide oxidizing conditions described herein to form sulfone compound 10c. If desired, compound 10c can be treated under reductive alkylation conditions described herein to form a dimethylamino aldehyde compound 10b as shown in Eq. 8b.

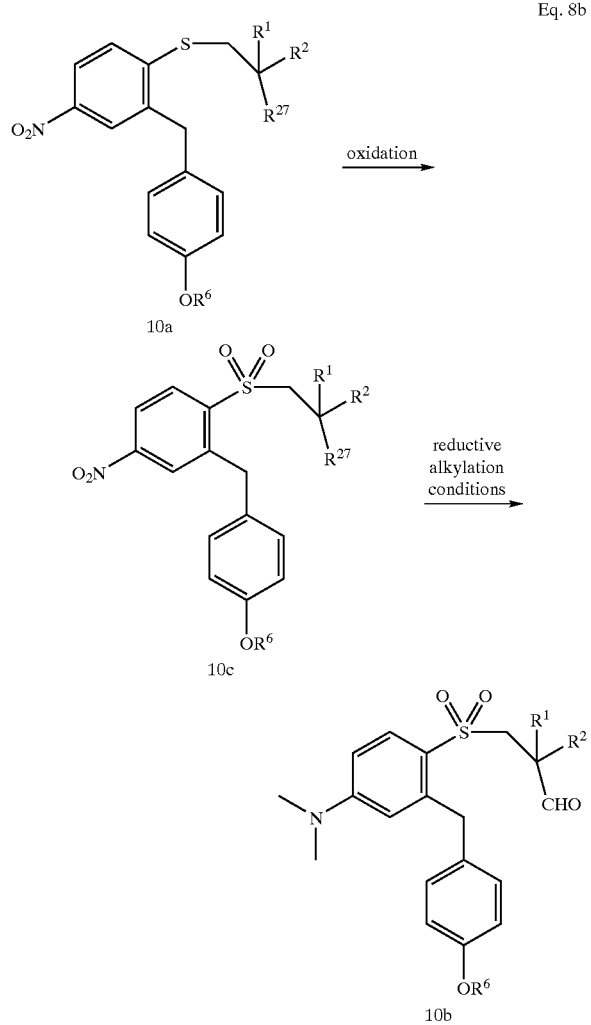

FIG. 1 shows an overall process by which substituted propionaldehyde compound 12 can be prepared. Compound 12 can be made, for example, by reacting a diol compound having the structure of Formula 37 in the presence of a carbonyl compound having the structure of Formula 38 and a source of $X^4$ to form an acid ester having the structure of Formula 36. $X^6$ can be hydroxy, halo, or —OC(O)$R^{18}$; preferably hydroxy or halo. When $X^6$ is halo, preferably it is chloro, bromo, or iodo; more preferably chloro. Alternatively $X^6$ can be hydroxy. When $X^6$ is hydroxy, the reaction of compound 37 with the carbonyl compound 38 is advantageously performed in the presence of a strong acid, preferably a strong mineral acid. Useful strong acids include HCl, HBr, HI, sulfuric acid, or a sulfonic acid. Useful sulfonic acids include methanesulfonic acid, trifluoromethanesulfonic acid, p-toluenesulfonic acid, and benzenesulfonic acid. Preferably the strong acid is HBr. $R^{10}$ and $R^{18}$ independently can be $C_1$ to about $C_{20}$ hydrocarbyl; preferably $C_1$ to about $C_{10}$ alkyl; more preferably $C_1$ to about $C_5$ alkyl; more preferably still methyl, ethyl, or isopropyl; and still more preferably methyl. $R^1$, $R^2$, and $X^4$, are as defined above. The source of $X^4$ can be, for example, a source of halide. The source of halide can be any source in which the halide can nucleophilically displace an acyloxy group such as —OC(O)$R^{10}$. For example, the source of halide can advantageously be the strong acid when the strong acid is HCl, HBr, or HI. Preferably the source of halide is a source of bromide such as NaBr, LiBr, or HBr. When the source of bromide is NaBr or LiBr, it is advantageous to perform the reaction in the presence of an acid catalyst. Preferably the source of halide is HBr or HI, more preferably HBr. Advantageously, the reaction to form compound 36 can be performed over a wide range of temperatures. Preferably the reaction is performed from about 50° C. to about 175° C., more preferably about 65° C. to about 150° C., still more preferably about 70° C. to about 130° C.

Acid ester 36 can be solvolyzed to form a substituted propanol compound having the structure of Formula 35. The solvolysis reaction can be performed under conditions known in the art for the solvolysis of carboxylic acid esters without displacing $X^4$. It is convenient to perform the solvolysis in the presence of an acid catalyst. A useful acid catalyst can be a mineral acid or an organic acid. When the acid catalyst is a mineral acid, it can be for example a hydrogen halide acid, sulfuric acid, or a sulfonic acid. Useful sulfonic acids include methanesulfonic acid, toluenesulfonic acid, benzenesulfonic acid, and trifluoromethanesulfonic acid. Useful hydrogen halide acids include hydrochloric acid, hydrobromic acid, and hydroiodic acid; preferably hydrobromic acid. The solvolysis can be performed in the presence of a solvent. Preferably the solvent is a $C_1$ to about $C_{10}$ alcohol solvent; more preferably a $C_1$ to about $C_5$ alcohol solvent; still more preferably methanol, ethanol, propanol, or 2-propanol; and more preferably still ethanol.

The reactions to form compounds 36 and 35 can be performed separately with individual isolation of the products. Alternatively, the reactions can be performed in a single reaction vessel or in a single reaction medium without isolation of compound 36.

The substituted propanol compound 35 can be oxidized to form the substituted propionaldehyde compound 12. This can be achieved by contacting compound 35 with an oxidizing agent. Oxidation conditions should be appropriate to those in which an alcohol group is oxidized in the presence of $X^4$. For example, the oxidizing conditions can comprise a mild oxidizing agent such as sulfur trioxide-pyridine complex. Other useful oxidizing conditions include, for example, contacting 35 with oxalyl chloride and triethylamine in the presence of a reactant such as DMSO. Another example of useful oxidizing conditions comprise contacting 35 with sodium hypochlorite in the presence of 2,2,6,6-tetramethyl-1-piperidinyloxy free radical (TEMPO). When the oxidizing agent is sulfur trioxide-pyridine complex, the oxidation can advantageously be performed at a temperature from about 10° C. to about 100° C.; preferably about 20° C. to about 75° C.; more preferably about 20° C. to about 50° C. The oxidation can be performed in the presence of a solvent. Useful solvents include for example a sulfoxide such as DMSO; or a chlorinated solvent such as methylene chloride, chloroform, or carbon tetrachloride. When the oxidizing agent is sulfur trioxide-pyridine complex, the complex can be added to the reaction mixture either as a slurry in a solvent or, preferably, as a solid added over a period of time (for example about 1 to about 15 hours).

In one preferred embodiment of the preparation of compound 12, both $R^1$ and $R^2$ are butyl. In an alternative preferred embodiment, one of $R^1$ and $R^2$ is ethyl and the other of $R^1$ and $R^2$ is butyl. When one of $R^1$ and $R^2$ is ethyl and the other of $R^1$ and $R^2$ is butyl, compound 12 can have an R absolute configuration about the quaternary carbon atom. Alternatively, compound 12 can have an S absolute configuration about the quaternary carbon atom.

Figure 2:
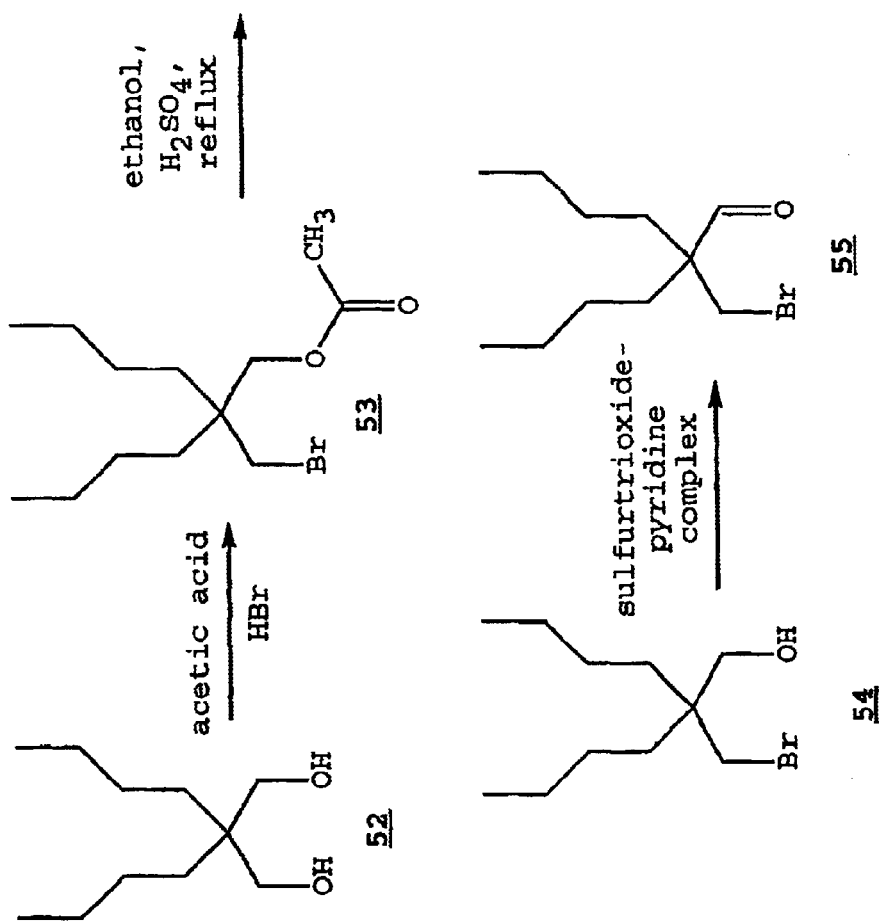
FIG. 2 shows a process by which 2,2-dibutyl-3-bromopropionaldehyde can be prepared using the methods of the present invention.

The reactions described herein that are useful for the preparation of compound 12 can be performed individually or in combination. FIG. 2 shows a preferred process by which 2,2-dibutyl-3-bromopropionaldehyde can be prepared using the methods of the present invention.

One embodiment of the present invention is shown in Eq. 8c wherein compound 12b can have the structure of compound 12d. Eq. 8c is exemplary of a large variety of methods by which thioacyl acetal compounds useful in the present invention can be made in which the acyl group and the acetal group can independently vary widely in structure. In Eq. 8c bromoaldehyde compound 53 is treated with potassium thioacetate to form thioacetyl aldehyde compound 12c. Compound 12c is treated with a trialkyl formate such as triethylformate in the presence of an acid catalyst such as a sulfonic acid catalyst (preferably toluenesulfonic acid) to form compound 12d, wherein Et is ethyl. The acetal-forming step can be performed, if desired, in the presence of a solvent, for example an alcohol solvent. When the acetal formed is an ethyl acetal, the solvent can conveniently be ethanol.

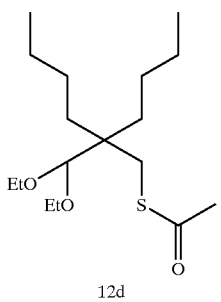

12d

Figure 1A:
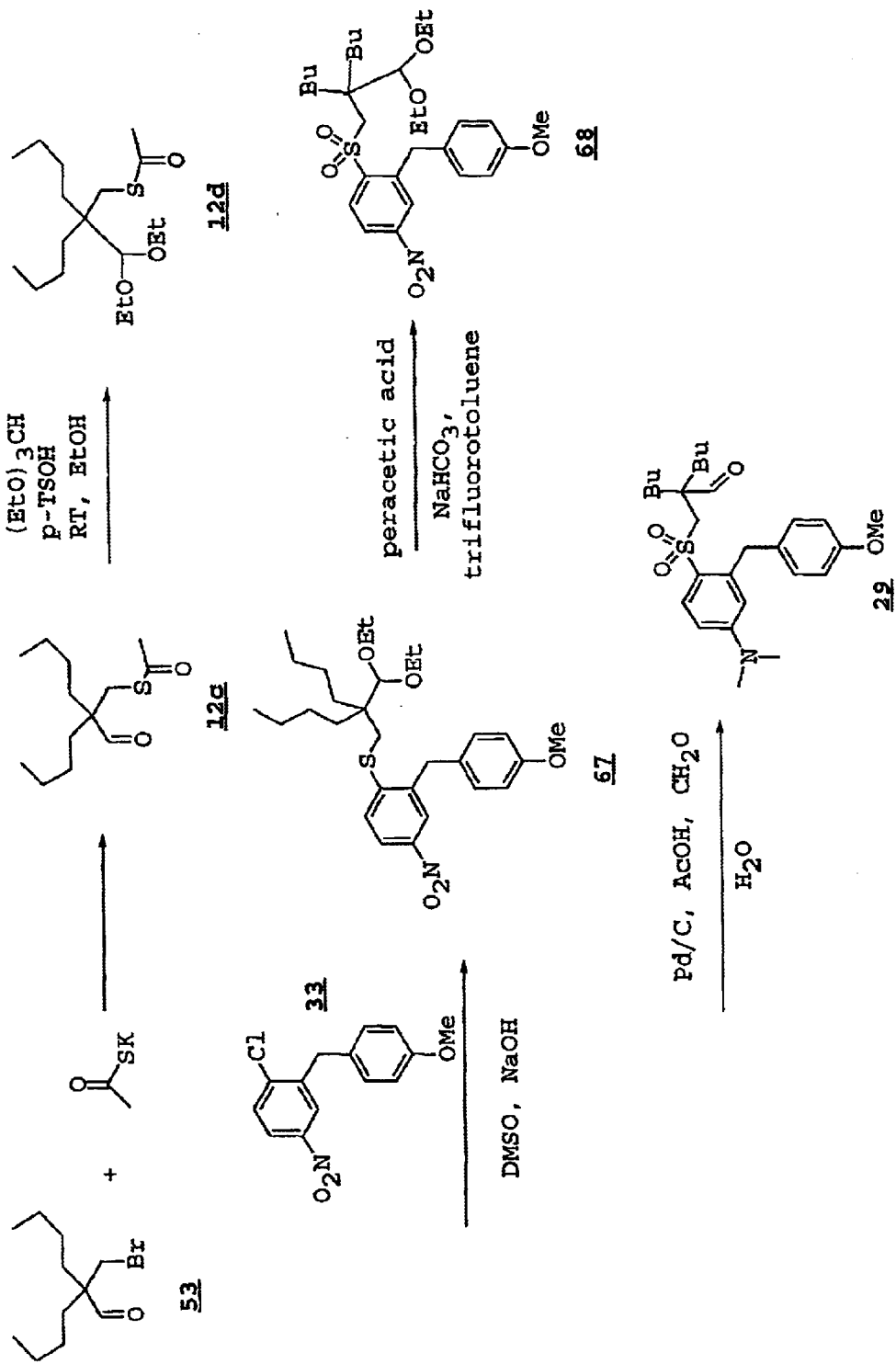
FIG. 1a shows a representative overall process by which nitro sulfide acetal compound 67 can be prepared and by which compound 67 can be used to produce compound 29.

FIG. 1a shows a representative overall process by which nitro sulfide acetal compound 67 (10a wherein $R^1$ and $R^2$ are both butyl and $R^{27}$ is a diethylacetal group) can be prepared and by which compound 67 can be used to produce compound 29.

Compound 12b can, if desired, be prepared by a number of other methods. For example, acrolein compound 77 can be contacted with thioacyl compound 78 to form acylthiomethyl aldehyde compound 79 as shown in Eq. 8d. In Eq. 8d, $R^{29}$ can be $C_1$ to about $C_{20}$ hydrocarbyl, preferably $C_1$ to about $C_{10}$ hydrocarbyl, more preferably $C_1$ to about $C_5$ hydrocarbyl, and still more preferably ethyl or butyl. $R^{30}$ can be $C_1$ to about $C_{20}$ hydrocarbyl, preferably $C_1$ to about $C_{10}$ hydrocarbyl, more preferably $C_1$ to about $C_5$ hydrocarbyl, and still more preferably methyl. Preferably the reaction of Eq. 8d is performed in the presence of a base catalyst such as an amine catalyst. For example the amine catalyst can be an alkylamine such as trialkylamine.

Eq. 8d

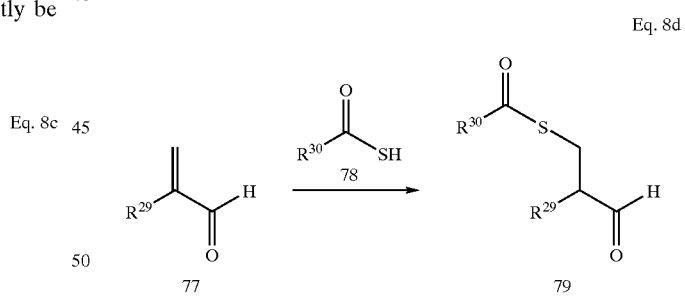

Eq. 8c

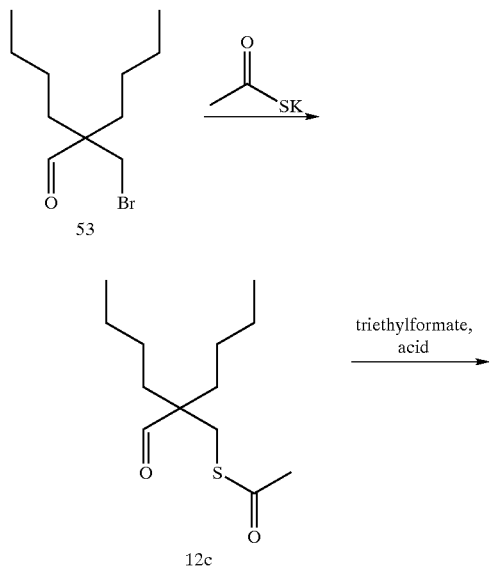

Compound 79 can be contacted with compound 20 to form acylthiomethyl alkene aldehyde compound 80 as shown in Eq. 8e. The reaction in Eq. 8e is preferably performed in the presence of an acid catalyst, preferably a sulfur acid catalyst such as sulfuric acid or a sulfonic acid. For example the acid catalyst can be p-toluenesulfonic acid, benzenesulfonic acid, methanesulfonic acid, or trifluoromethanesulfonic acid. The reaction can conveniently be carried out under heating conditions, for example at a temperature of about 50° C. to about 150° C., preferably about 75° C. to about 125° C., more preferably about 100° C. to about 115° C.

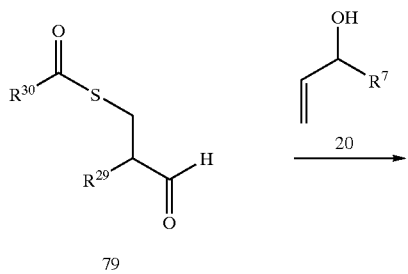

79

Eq. 8e

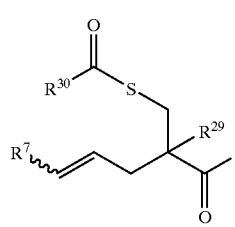

80

Compound 80 can be derivatized under acetal-forming conditions to form unsaturated acetal compound 81. In compound 81, $R^{31}$ and $R^{32}$ independently can be $C_1$ to about $C_{20}$ alkoxy or, together with the carbon atom to which they are attached can form a cyclic acetal. Where $R^{31}$ and $R^{32}$ are alkoxy, preferably they are $C_1$ to about $C_{10}$ alkoxy, more preferably $C_1$ to about $C_5$ alkoxy, more preferably still methyl or ethyl, and still more preferably ethyl. Where $R^{31}$ and $R^{32}$ together form a cyclic acetal, preferably they form an ethylene glycol acetal or a 1,3-propanediol acetal, more preferably an ethylene glycol acetal. For example, compound 80 can be contacted with an alcohol or a mixture of alcohols in the presence of a catalyst such as an acid catalyst. Alternatively, compound 80 can be treated with an orthoformate such as triethyl orthoformate or trimethyl orthoformate to form the acetal.

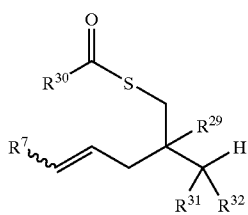

81

Compound 81 can be reduced to produce thiomethyl acetal compound 82. It will be apparent to one of skill in the art given the present disclosure that compound 82 can be used in place of compound 12b in the reaction of Eq. 8a to form sulfide 10a. Reduction conditions to convert compound 81 to compound 82 can vary widely. For example, compound 81 can be treated with a hydrazide such as p-toluenesulfonyl hydrazide in the presence of an amine such as piperidine to form compound 82.

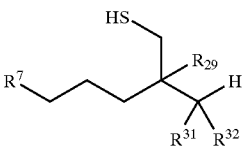

82

Once the nitro sulfide aldehyde compound 10 is formed in the sulfide-forming step, 10 can be isolated by methods known in the art or it can be oxidized to form nitro sulfone aldehyde compound 2 by methods described above. While intermediate compounds can optionally be isolated, stored, or transported, it is convenient to perform the sulfide-forming step and the oxidation step in one reaction vessel without isolation of intermediate structures.

The method of the present invention can further comprise a reduction step in which a substituted benzophenone compound 13

Eq. 9

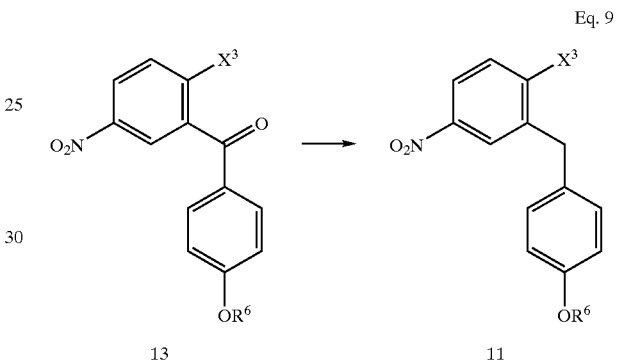

13        11 is reduced to form the substituted diphenyl methane compound 11 wherein $R^6$ and $X^3$ are defined above. The reduction step is shown in Eq. 9. For example, the reduction step can be carried out by contacting compound 13 with trifluoromethanesulfonic acid (triflic acid) and a silane such as triethyl silane. It is useful to perform the reduction step in the presence of a solvent, for example a strong acid solvent such as trifluoroacetic acid. When trifluoroacetic acid is used as a solvent, the triflic acid is preferably used in a catalytic amount. Particularly, it is useful to dissolve 13 in trifluoroacetic acid, add the triflic acid, and then add triethyl silane. Reaction temperature during the addition of the triethyl silane can be controlled, if necessary, by cooling. The reaction temperature can be controlled in the range of about 25° C. to about 100° C., preferably about 30° C. to about 75° C., and more preferably about 45° C. to about 50° C. Other silanes are useful in the present reaction also, for example, polymethyl hydrosiloxane (PMHS) or other trialkylsilanes.

Alternatively, the reduction of 13 to 11 can be carried out in a solvent such as methylene chloride in the presence of triflic acid and a silane such as triethyl silane. When trifluoroacetic acid is absent from the reaction mixture, typically a larger-than-catalytic amount of triflic acid is required. Another method of reducing 13 to 11 will comprise treating 13 with a Lewis acid such as aluminum chloride and a silane such as triethyl silane. In another alternative, the reduction can be carried out by treating 13 with sodium borohydride in the presence of a catalyst. In a further alternative, the reduction can be carried out by treating 13 with sulfuric acid in the presence of a noble metal catalyst such as a palladium catalyst, preferably Pd/C. In a still further alternative, 13 can be reduced to the corresponding alcohol, for example with a borohydride such as sodium borohydride. The resulting alcohol can be treated, for example, with sodium borohydride and a silane such as triethylsilane. The alcohol can be reduced to 11 by other means, for example treating the alcohol with a sulfonating reagent such as methanesulfonyl chloride or toluenesulfonyl chloride and then treating the resulting sulfonic acid ester with sodium borohydride.

The method of the present invention can also further comprise an acylation step in which a protected phenol compound having the structure of Formula 14

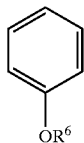

14 is treated with a substituted benzoyl compound having the structure of Formula 15

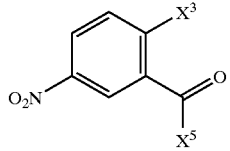

15 under acylation conditions to produce a substituted benzophenone compound having the structure of Formula 13 wherein $R^6$ and $X^3$ are defined above; $X^5$ can be hydroxy, halo, or —$OR^{14}$; and $R^{14}$ can be an acyl group. This overall acylation step is shown in Eq. 10.

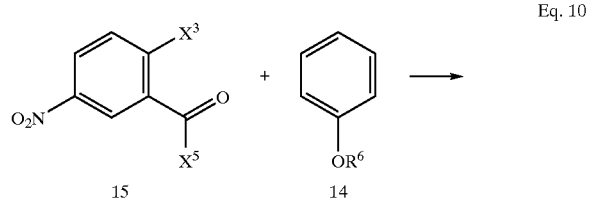

Eq. 10

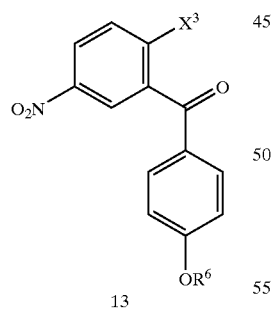

13

The acylation conditions can comprise Friedel-Crafts acylation conditions. For example the acylation conditions can further comprise a Lewis acid. Useful Lewis acids include aluminum-containing Lewis acids such as an aluminum trihalide; boron-containing Lewis acids such as boron trifluoride, boron trifluoride etherate, or boron trichloride; tin-containing Lewis acids such as $SnCl_4$; halogen-containing Lewis acids such as HF; iron-containing Lewis acids such as $FeCl_3$; antimony-containing Lewis acids such as $SbF_5$; and zinc-containing Lewis acids such as $ZnI_2$ or $ZnCl_2$. When the Lewis acid is an aluminum trihalide, preferably it is $AlCl_3$ or $AlBr_3$, more preferably $AlCl_3$. Alternatively, the Lewis acid can be supported on a solid support such as a clay. For example, the Lewis acid can comprise an $FeCl_3$ on clay composition such as Envirocat.

Alternatively, the acylation can be run in the presence of a strong protic acid such as sulfuric acid; a phosphoric acid, for example o-phosphoric acid or polyphosphoric acid (PPA); or a sulfonic acid, for example p-toluenesulfonic acid, methanesulfonic acid, benzenesulfonic acid, or trifluoromethanesulfonic acid.

$X^5$ can be hydroxy, halo, or —$OR^{14}$. For example, $X^5$ can be hydroxy, bromo, iodo, or —$OR^{14}$.

When $X^5$ is halo, preferably it is chloro, bromo, or iodo. In one useful embodiment $X^5$ is chloro. In another useful embodiment $X^5$ is bromo or iodo, preferably bromo. When $X^5$ is halo, it is preferred that the acylation conditions further comprise a Lewis acid as described above, for example an aluminum trihalide. Useful aluminum trihalides include aluminum tribromide and aluminum trichloride, preferably aluminum trichloride.

When $X^5$ is hydroxy, it is preferred that the acylation conditions further comprise a strong protic acid. Some useful strong protic acids include sulfuric acid, a sulfonic acid, or a phosphorus oxy acid. Useful phosphorus oxy acids include orthophosphoric acid (commonly known as phosphoric acid, $H_3PO_4$), pyrophosphoric acid ($H_4P_2O_7$), or polyphosphoric acid (PPA). Preferably the phosphorus oxy acid is phosphoric acid or polyphosphoric acid, preferably polyphosphoric acid. Combinations of phosphorus oxy acids are also useful in the present invention. The phosphorus oxy acid can be added as the acid per se or it can be generated in situ, for example by the hydrolysis of a phosphorus halide compound such as $PCl_5$ or by the hydrolysis of a phosphorus oxide compound such as $P_2O_5$.

When $R^{14}$ is —$OR^{14}$ and $R^{14}$ is an acyl group, compound 15 is a carboxylic acid anhydride. The acid anhydride can have a symmetrical structure; i.e., $X^5$ can have the structure of Formula 46. Alternatively, the acid anhydride can be a mixed anhydride. For example $R^{14}$ can be a formyl group, an acetyl group, a benzoyl group or any other convenient acyl group.

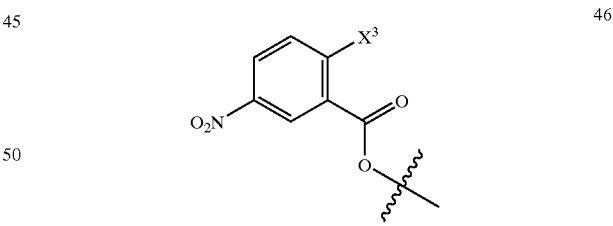

46

When $X^5$ is —$OR^{14}$, it is preferred that the acylation conditions further comprise a Lewis acid as described above, for example an aluminum trihalide. Useful aluminum trihalides include aluminum tribromide and aluminum trichloride, preferably aluminum trichloride.

An alternative method for the preparation of compound 13 is shown in Eq. 11. When $X^5$ of compound 15 is halo or —$OR^{14}$, compound 15 can be treated with compound aryl metal complex 56 wherein L is a metal-containing moiety and $R^6$ is as defined above. The group L can be, for example, $MgX^6$, Na, or Li, wherein $X^6$ is a halogen. When L is $MgX^6$ (in other words, when 56 is a Grignard reagent), X is preferably Br, Cl, or I; more preferably Br or Cl.

Eq. 11

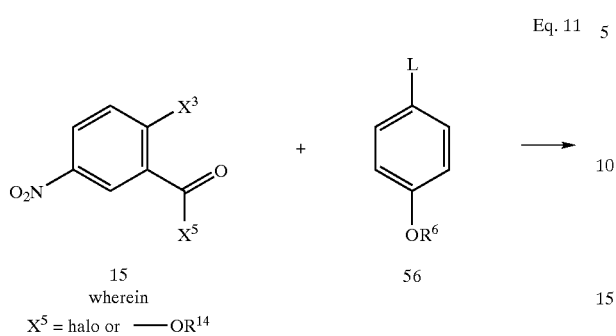

15
wherein
$X^5$ = halo or —$OR^{14}$

56

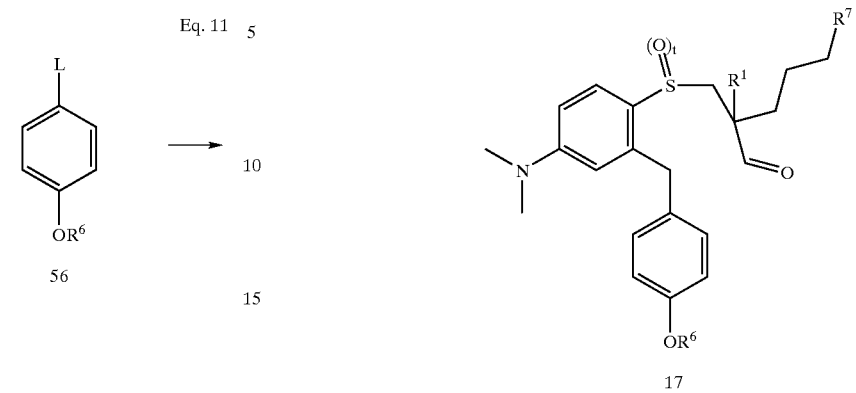

17

The reduction and reductive alkylation of compound 16 to compound 17 can be performed in a single step or it can be performed in discrete steps. For example, the reduction of the double bond can be done at the same time as the reductive alkylation of the nitro group. Alternatively, the aliphatic C—C double bond in compound 16 can be reduced to a single bond in a step that is discrete from the reductive alkylation of the nitro group to the dimethylamino group. As another alternative, in a first step the nitro group and the alkene double bond of compound 16 can be reduced to an amino group and to an alkyl group, respectively, and then the amino group can be methylated. The reduction of the nitro group and the alkene double bond will be readily performed with the use of a hydrogenation catalyst as is known in the art. Such a reduction will run in the presence of $H_2$. The methylation of the reduced amino group can be performed with essentially any methylating agent as is known in the art, for example a methyl halide such as methyl iodide, methyl bromide, or methyl chloride. Another useful methylating agent is dimethyl sulfate.

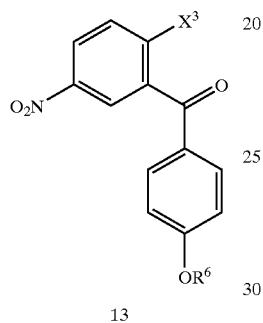

13

The present inventive method can further comprise one or more steps wherein a nitro alkenyl aldehyde compound having the structure of Formula 16 is reduced and reductively alkylated to form an amino alkyl aldehyde compound having the structure of Formula 17 (Eq. 12) wherein $R^1$ and $R^6$ are defined above, $R^7$ is H or $C_1$ to about $C_{17}$ hydrocarbyl, and t is 0, 1, or 2. Preferably $R^7$ is a $C_1$ to about $C_{10}$ alkyl group, more preferably a $C_1$ to about $C_5$ alkyl group, still more preferably $C_1$ to about $C_3$ alkyl group, and more preferably still methyl. Preferably t is 2.

The conditions under which compound 16 is reduced and reductively alkylated can include, for example, contacting 16 with a source of formaldehyde and a source of $H_2$ in the presence of a catalyst. The conversion is preferably performed at elevated $H_2$ pressure. It is useful to perform the conversion at $H_2$ pressures ranging from about 100 to about 700,000 kPa, preferably from about 200 to about 300,000 kPa, more preferably from about 300 to about 100,000 kPa, still more preferably from about 350 to about 10,000 kPa, and more preferably still from about 400 to about 1000 kPa.

Eq. 12

The source of formaldehyde can be essentially any source that produces the equivalent of $CH_2O$. For example, the source of formaldehyde can be formalin, an acetal of formaldehyde such as dimethoxymethane, paraformaldehyde, trioxane, or any polymer of $CH_2O$. Conveniently the source of formaldehyde can be formalin, and preferably about 35% to about 37% formalin.

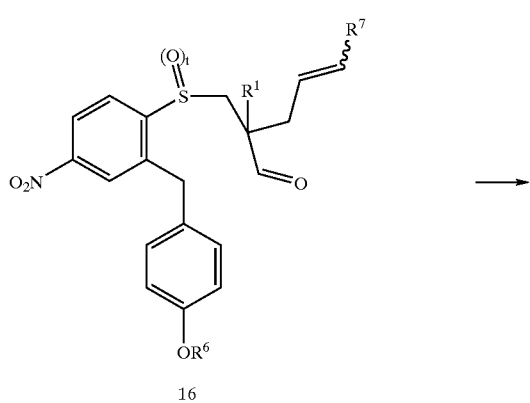

16

The catalyst for the reduction and reductive alkylation can be either a heterogeneous catalyst or a homogeneous catalyst. Preferably the catalyst is a metal, for example the catalyst can be a noble metal catalyst. Useful noble metal catalysts include Pt, Pd, Ru, and Rh. Preferably the noble metal catalyst is a Pd catalyst. The noble metal catalyst can be used either in a homogeneous or in a heterogeneous form. When used in a heterogeneous form, the catalyst can be used, for example, as the metal per se or on a solid support such as carbon or an aluminum oxide. In a particularly preferred embodiment, the catalyst comprises palladium and more preferably Pd on carbon. In another embodiment the catalyst comprises a nickel catalyst such as a high-surface area nickel catalyst. A useful high-surface area nickel catalyst is Raney nickel.

An acid can be present in the reaction mixture during the reduction and reductive alkylation. Preferably the acid is a strong acid and more preferably a strong mineral acid. For example, the acid can be sulfuric acid.

A solvent can conveniently be present in the reaction mixture during the reduction and reductive alkylation. Useful solvents include an alcohol, an ether, a carboxylic acid, an aromatic solvent, an alkane, a cycloalkane, or water. Preferably the solvent is an alcohol solvent such as a $C_1$ to about $C_{10}$ alcohol; more preferably a $C_1$ to about $C_5$ alcohol; and more preferably still methanol, ethanol, propanol, or isopropyl alcohol. In a particularly preferred embodiment, the solvent is ethanol.

The reduction and reductive alkylation reaction can be run at any convenient temperature, for example from about 0° C. to about 200° C., preferably from about 10° C. to about 150° C., more preferably from about 15° C. to about 100° C., still more preferably from about 20° C. to about 75° C., more preferably still from about 25° C. to about 60° C., and more preferably yet from about 30° C. to about 40° C.

Alternatively, the conversion of 16 into 17 can be performed in discrete steps. For example, in a first step the nitro group and the alkene double bond of compound 16 can be reduced to an amino group and to an alkyl group, respectively. In a second step the amino group can be methylated. The reduction of the nitro group and the alkene double bond can be readily performed with the use of a hydrogenation catalyst as is known in the art. Such a reduction will run in the presence of $H_2$. The methylation of the reduced amino group can be performed with essentially any methylating agent as is known in the art, for example a methyl halide such as methyl iodide, methyl bromide, or methyl chloride. Another useful methylating agent is dimethyl sulfate.

An alternative route to compound 17 is shown in Eq. 13, wherein u of compound 16a is 0 or 1 (in other words, when compound 16a is a sulfide or a sulfoxide compound). In the instant route, compound 16a can be reduced by methods described herein (for example by contacting 16a with $H_2$ and a hydrogenation catalyst such as Pd/C) to form compound 57 wherein u is 0 or 1, $R^1$, $R^6$, and $R^7$ are as defined above, and $R^{19}$ can be —$NH_2$, —NHOH, or —$NO_2$. Compound 57 can be oxidized (for example by methods described herein for the conversion of sulfides or sulfoxides to sulfones) to compound 58 wherein $R^1$, $R^6$, and $R^7$ are as defined above, and $R^{20}$ can be —$NH_2$, —NHOH, or —$NO_2$. Compound 58 can be alkylated or reductively alkylated by methods described herein to form compound 17 wherein t is 2.

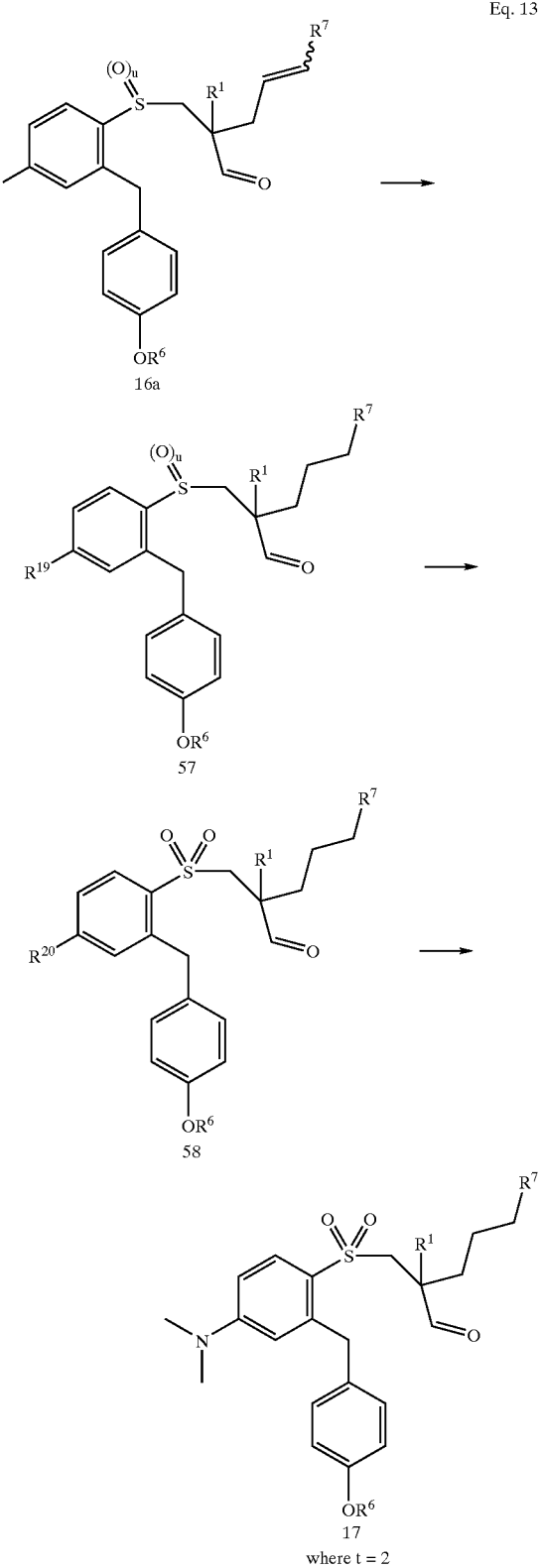

Eq. 13

The method of the present invention can further comprise a thermolysis step wherein an acetal compound having the structure of Formula 18

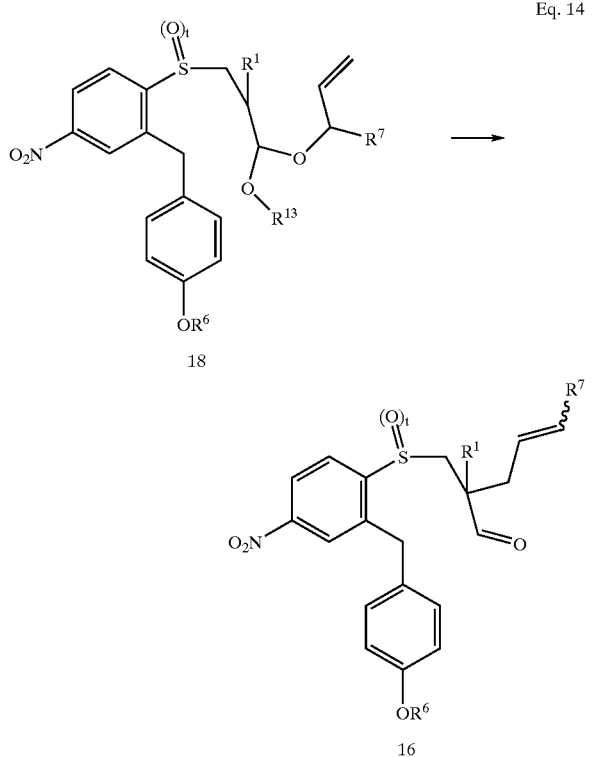

Eq. 14

18

16 is thermolyzed to form the nitro alkenyl aldehyde compound 16, wherein $R^1$, $R^6$, and t are defined above; $R^7$ can be H or $C_1$ to about $C_{17}$ hydrocarbyl; and $R^{13}$ can be H or $C_1$ to about $C_{20}$ hydrocarbyl. The thermolysis step is shown in Eq. 14. Preferably t is 2. Preferably $R^7$ is a $C_1$ to about $C_{10}$ alkyl group, more preferably a $C_1$ to about $C_5$ alkyl group, still more preferably $C_1$ to about $C_3$ alkyl group, and more preferably still methyl. $R^{13}$ is preferably a $C_1$ to about $C_{10}$ hydrocarbyl group, more preferably a $C_1$ to about $C_{10}$ alkenyl group, still more preferably a $C_1$ to about $C_5$ alkenyl group, and more preferably still a $C_1$ to about $C_4$ alkenyl group. In one preferred embodiment, $R^{13}$ is a group having the structure of Formula 43 wherein $R^7$ is as defined above. Preferably $R^{13}$ is 1-buten-3-yl.

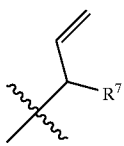

43

The thermolysis reaction can advantageously be performed in the presence of a base. Useful bases include without limitation a metal hydride, a metal hydroxide, a metal carbonate, or a metal bicarbonate. Preferably the base is a metal hydride such as calcium hydride, lithium hydride, sodium hydride, or potassium hydride. More preferably the base is calcium hydride. Other useful bases include sodium hydroxide, potassium hydroxide, potassium carbonate, sodium carbonate, potassium bicarbonate, or sodium bicarbonate. The thermolysis reaction can be run, for example, by contacting compound 18 with the base over a period of time, preferably under essentially anhydrous conditions. Surprisingly, the presence of a soluble base such as triethylamine or pyridine during the conversion of 18a to 47 can be advantageously used to slow the reaction rate relative to reaction conditions in which the soluble base is absent. The thermolysis can be run in the presence of a solvent. Essentially any solvent that is unreactive under the thermolysis reaction conditions is useful. Aprotic solvents are especially useful and aromatic solvents are preferred, such as benzene, toluene, o-xylene, m-xylene, p-xylene, mesitylene, and naphthalene. Especially preferred solvents include toluene, o-xylene, m-xylene, p-xylene, or mesitylene; more preferably toluene, o-xylene, m-xylene, or p-xylene; and more preferably still toluene or o-xylene. Other useful solvents include an ether such as tetrahydrofuran, diethyl ether, or diphenyl ether; an ester such as ethyl acetate; an alcohol such as ethanol or t-butyl alcohol; or a ketone such as acetone or benzophenone.

In another embodiment, the thermolysis can be performed neat, i.e., in the absence of a solvent. For example, compound 18 can be heated neat to produce compound 16a. When compound 18 is heated neat, the thermolysis can be run, if desired, at subambient pressure. For example, the thermolysis can be run at a pressure at which elimination products produced by the thermolysis boil away. Operating the reaction under such conditions will aid in driving the thermolysis reaction to completion. Advantageously, the reaction pressure during the thermolysis can be less than about 760 mmHg (101 kPa), preferably less than about 500 mmHg (66.6 kPa), more preferably less than about 250 mmHg (33.3 kPa), more preferably still less than about 100 mmHg (13.3 kPa), still more preferably less than about 50 mmHg (6.7 kPa), and more preferably yet less than about 10 mmHg (1.3 kPa).

The thermolysis can be run over a wide range of temperatures. For example the thermolysis can be run at a temperature in the range of about 10° C. to about 250° C., preferably about 50° C. to about 200° C., more preferably about 75° C. to about 175° C. and more preferably still about 100° C. to about 150° C. Conveniently the thermolysis can be run in a refluxing solvent, for example refluxing o-xylene. Alternatively, the thermolysis can be performed at pressures above ambient pressure, thereby allowing the reaction to proceed at temperatures above the ambient-pressure boiling point of the solvent.

The thermolysis reaction is preferably performed under dry or essentially anhydrous conditions and in the absence of acid to prevent reverse reaction and byproduct formation.

Without intending to limit the scope of the present invention, the thermolysis reaction to form compound 16 is believed to proceed by the intermediacy of an enol ether compound. For example, bis-butenyl acetal compound 18a is thought to eliminate a molecule of 3-buten-2-ol to form enol ether 47 (a pre-Claisen intermediate) as shown in Eq. 15. Compound 47 is then believed to undergo a [3,3]-sigmatropic shift (also known as a Claisen rearrangement) to form butenyl sulfone aldehyde compound 31 as shown in Eq. 16. Although compound 47 is shown herein as having a E-configuration across the double bond between the methanesulfonyl moiety and the alkoxy moiety, it is also possible that this compound can form in the Z-configuration.

Eq. 15

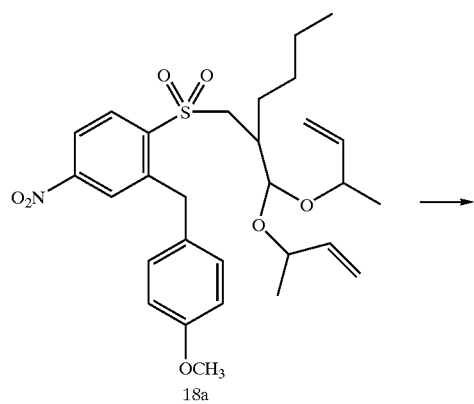

18a

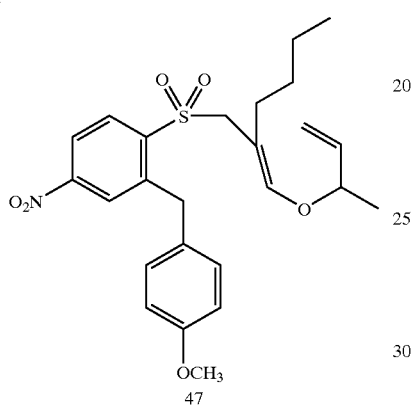

47

Eq. 16

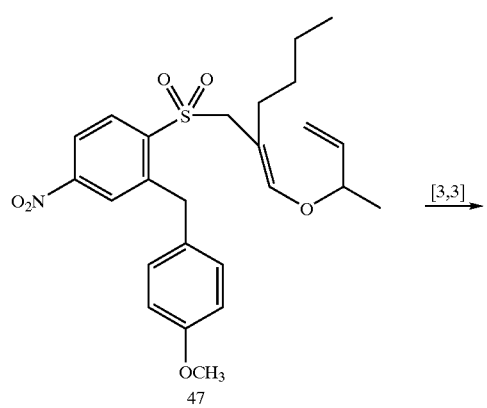

47

[3,3]

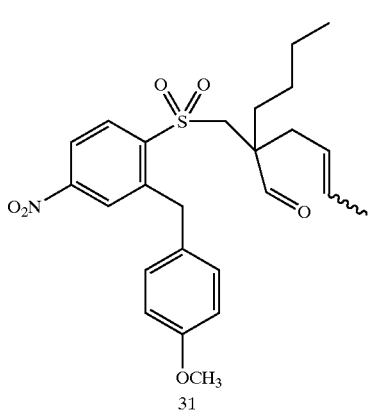

31

The conversion of 18a to 31 can be carried out for example by heating at 145° C. a toluene or o-xylene solution of a mixture comprising 18a or a mixture of 18a and 47, preferably in the presence of calcium hydride. Alternatively, the conversion of 18a to 31 can be achieved by filtering crude 18a through an acidic medium such as silica gel or a basic medium such as basic alumna prior to heating.

The addition of soluble bases such as triethylamine or pyridine during the conversion of 18a to 47 can be used, if desired, to decrease the thermolysis reaction rate relative to the situation in which the soluble base is absent.

Compound 18 can be prepared by a step in which a monoalkyl aldehyde compound having the structure of Formula 19 is reacted with an allyl alcohol compound having the structure of Formula 20 in the presence of a hydroxylated solvent having the structure $HOR^{13}$ to form an acetal compound having the structure of Formula 18, wherein $R^1$, $R^6$, $R^7$, $R^{13}$, and t are as defined above. Preferably t is 2. In a preferred embodiment, $R^{13}$ has the structure of Formula 43. For example, this embodiment can be realized if the allyl alcohol compound 20 itself is used as a hydroxylated solvent, preponderating over another hydroxylated solvent or essentially in the absence of another hydroxylated solvent. The conversion of compound 19 into compound 18 is shown in Eq. 17.

Eq. 17

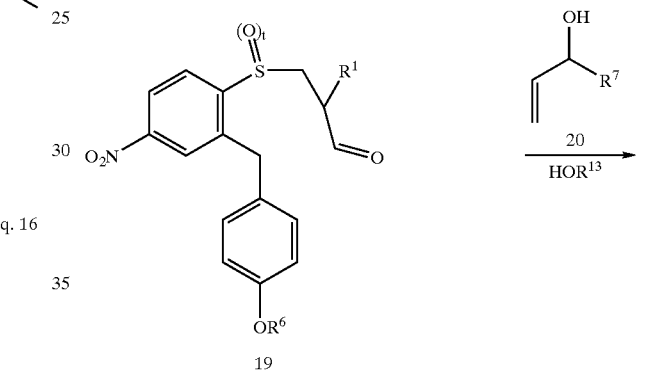

19

18

Acetal compound 18 can be prepared by numerous methods employing various conditions known in the art. The reaction to form the acetal is preferably performed in the presence of an acid catalyst. The catalyst can be, for example, a strong acid such as sulfuric acid, hydrochloric acid, phosphorous acid, phosphoric acid, trifluoroacetic acid, or a sulfonic acid. Useful sulfonic acids include methanesulfonic acid, toluenesulfonic acid, benzenesulfonic acid, and trifluoromethanesulfonic acid. However, organic acids and acidic heterogeneous catalysts also work to mediate this reaction, for example pyridinium p-toluenesulfonate, acetic acid, propionic acid, Amberlyst 15, acidic zeolites, acidic clay, $Pd(PhCN)_2Cl_2$, and $AlCl(CH_2CH_3)_2$. Virtually any Bronsted-Lowry or Lewis acid can be employed as a catalyst. The acetal-forming reaction can if desired be performed in the presence of a solvent. Useful solvents include chlorinated solvents such as methylene chloride, chloroform, or carbon tetrachloride; aromatic solvents such as benzene, toluene, o-xylene, m-xylene, p-xylene, mesitylene, or trifluoromethylbenzene; aprotic solvents including $CH_3CN$, ethyl acetate, isopropyl acetate, butyl acetate, tetrahydrofuran, methyl isobutyl ketone, 1,4-dioxane; or alcohols such as 3-buten-2-ol. The reaction can be run at essentially any convenient temperature that does not lead to significant degradation of starting material or product. For example, the temperature can be in the range of about 0° C. to about 200° C.; preferably about 20° C. to about 150° C.; more preferably about 30° C. to about 135° C. The reaction can be performed in a refluxing solvent such as refluxing methylene chloride. The conversion can conveniently be performed during azeotropic removal (distillation) of the solvent and water. For example, the conversion can be achieved during azeotropic removal of toluene (about 105° C. to about 115° C.) or of xylene (about 125° C. to about 135° C.).

Optionally, removal of water during the reaction or concomitant with the reaction can advantageously be used to increase conversion or yield. Without meaning to limit the scope of the invention, it is believed that removal of water drives the acetal-forming reaction toward completion. For example, process apparatus similar to a Dean-Stark trap or azeotropic distillation equipment can be used to remove water. Other methods such as molecular sieve (zeolites), isopropenyl acetate, and trimethyl orthoformate can also be used.

Advantageously, the conversion of 18a to 47 and the conversion of 47 to 31 can be carried out sequentially or simultaneously in a single reaction vessel or in a single reaction mixture without isolation. To further advantage, the preparation of the acetal 18 from aldehyde 19, the conversion of 18 to the corresponding enol ether intermediate, and the conversion of the enol ether intermediate to 31 can all be carried out in a single reaction vessel or reaction mixture. For example, 2-(((4-methylphenyl)sulfonyl)methyl)hexanal can be heated in a solvent such as toluene in the presence of 3-buten-2-ol and p-toluenesulfonic acid with removal of water (e.g., with a Dean-Stark trap) to produce 2-butyl-2-(((4-methylphenyl)sulfonyl)methyl)hex-4-enal.

This useful and surprising overall method for preparing a 2-alkenyl-2,2-disubstituted aldehyde 49 has general applicability. The general method can be employed in the conversion of a 3-sulfur-propionaldehyde compound 48 to the 3-sulfur-propionaldehyde olefin compound 49 as shown in Eq. 18. Conditions described above for the conversion of compound 19 to compound 16 are useful in the broad reaction of Eq. 18.

Eq. 18

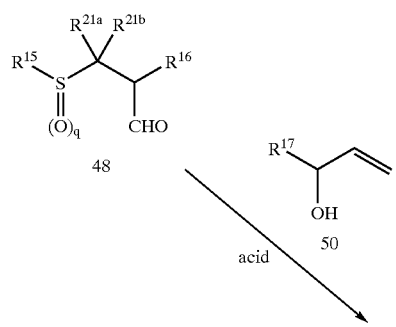

In the reaction of Eq. 18:

$R^{15}$ is selected from the group consisting of H, alkyl, alkenyl, alkynyl, aryl, alkylaryl, arylalkylaryl, and acyl, wherein alkyl, alkenyl, alkynyl, aryl, alkylaryl, arylalkylaryl, and acyl optionally are substituted with at least one $R^{22}$ group;

$R^{16}$, $R^{17}$, $R^{21a}$, and $R^{21b}$ are independently selected from the group consisting of H and hydrocarbyl;

$R^{22}$ is selected from the group consisting of H, $-NO_2$, amino, $C_1$ to about $C_{10}$ alkylamino, di($C_1$ to about $C_{10}$)alkylamino, $C_1$ to about $C_{10}$ alkylthio, hydroxy, $C_1$ to about $C_{10}$ alkoxy, cyanato, isocyanato, halogen, $OR^6$, $SR^6$, $SR^6R^{6a}$, and $NR^6R^{6a}$;

$R^6$ and $R^{6a}$ independently are selected from the group consisting of H and a protecting group; and q is 0, 1, or 2.

Preferably $R^{15}$ is selected from the group consisting of aryl, alkylaryl, and arylalkylaryl. More preferably $R^{15}$ is selected from the group consisting of aryl, alkylaryl, and arylalkylaryl, wherein aryl, alkylaryl, and arylalkylaryl are optionally substituted with at least one $R^{22}$ group. More preferably still, $R^{15}$ is arylalkylaryl optionally substituted with at least one $R^{22}$ group, and more preferably still $R^{15}$ is 2-(phenylmethyl)phenyl optionally substituted with at least one $R^{22}$ group. $R^{15}$ therefore can include without limitation any of the moieties shown in Table A, wherein $R^6$ is as defined above.

TABLE A

| Number | Structure |
|--------|-----------|
| 59a | 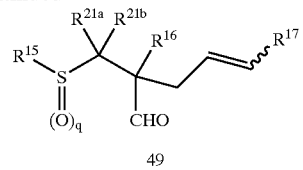 |
| 59b | 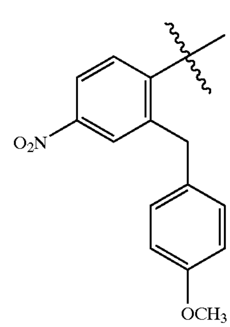 |

TABLE A-continued

| Number | Structure |
|---|---|
| 59c | (4-nitro substituted benzyl-phenyl) |
| 59d | (4-dimethylamino substituted benzyl-phenyl-OR⁶) |
| 59e | (4-nitro substituted benzyl-phenyl-OH) |
| 59f | (H₃CO, Cl substituted benzyl-phenyl) |
| 59g | (benzyl-phenyl) |
| 59h | (H₃CO, Cl substituted benzyl-phenyl-OR⁶) |
| 59i | (O₂N substituted benzyl-phenyl-OCH₃) |
| 59j | (H₃CO, Cl substituted benzyl-phenyl-OCH₃) |

When $R^{16}$ is hydrocarbyl, it can be unsubstituted hydrocarbyl, for example $C_1$ to about $C_{10}$ alkyl and preferably $C_1$ to about $C_5$ alkyl. More preferably, when $R^{16}$ is unsubstituted hydrocarbyl, it is ethyl or butyl.

In the reaction of Eq. 18, $R^{17}$ is preferably hydrocarbyl, more preferably $C_1$ to about $C_{10}$ alkyl, still more preferably $C_1$ to about $C_5$ alkyl, and more preferably still methyl.

$R^{21a}$ and $R^{21b}$ preferably independently are selected from the group consisting of H, $C_1$ to about $C_{10}$ alkyl, $C_2$ to about $C_{10}$ alkenyl, and $C_2$ to about $C_{10}$ alkynyl; more preferably $R^{21a}$ and $R^{21b}$ are both H.

Preferably q is 2 in the reaction of Eq. 18.

The reaction of Eq. 18 can be run at essentially any convenient temperature that does not lead to significant degradation of starting material or product. For example, the temperature can be in the range of about 0° C. to about 200° C.; preferably about 20° C. to about 150° C.; more preferably about 30° C. to about 135° C.; and more preferably still about 30° C. to about 100° C.

Compound 48 can be prepared by any of a variety of methods. For example, 48 can be prepared by the reaction of Eq. 18a wherein an acrolein compound (5) is treated with a nucleophilic organosulphur compound (66) to produce compound 48. The reaction of Eq. 18a is preferably performed in the presence of a base, preferably an amine, and more preferably an alkylamine such as triethylamine. Preferably the base is present in a catalytic amount. In Eq. 18a $R^{15}$, $R^{16}R^{21a}$, $R^{21b}$, and q are as defined above. ,

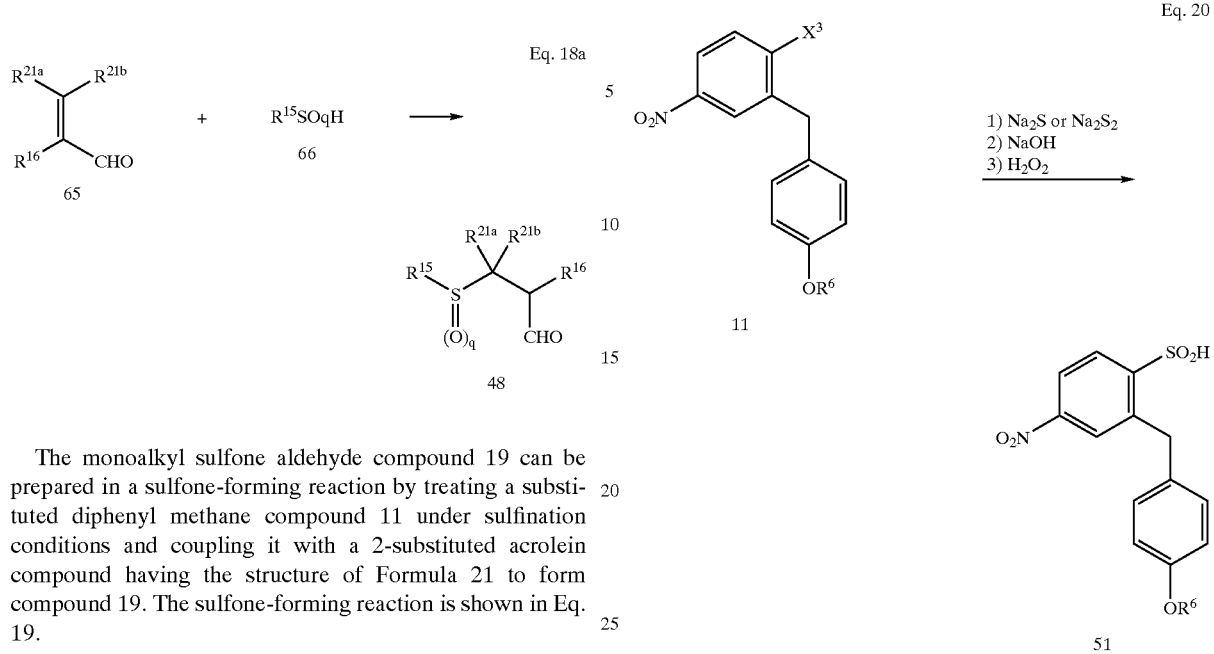

The monoalkyl sulfone aldehyde compound 19 can be prepared in a sulfone-forming reaction by treating a substituted diphenyl methane compound 11 under sulfination conditions and coupling it with a 2-substituted acrolein compound having the structure of Formula 21 to form compound 19. The sulfone-forming reaction is shown in Eq. 19.

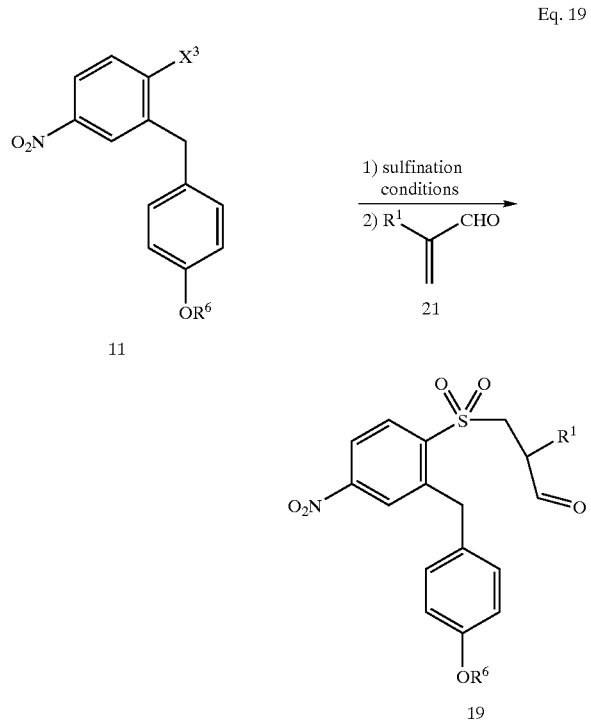

The sulfination conditions can comprise, for example, treating compound 11 with a source of a metal sulfide such as $Na_2S$, $Na_2S_2$, or $Li_2S$, preferably $Na_2S_2$. The sulfination conditions can further comprise water. After treating with the metal sulfide, the substrate can be oxidized to form sulfinic acid 51 or a salt thereof (Eq. 20). A variety of oxidizing conditions can be used to effect this oxidation. For example, a useful oxidizing agent includes a source of hydrogen peroxide.

During the addition of the metal sulfide, the temperature of the mixture can vary over a wide range. It is useful to react compound 11 with the metal sulfide at a temperature of about 25° C. to about 125° C., preferably about 40° C. to about 100° C., and more preferably about 50° C. to about 80° C. This reaction can be run in the presence of a solvent. Essentially any solvent into which hydrogen peroxide can dissolve is useful for the present reaction. Useful solvents include an alcohol such as a $C_1$ to about $C_{10}$ alcohol; preferably a $C_1$ to about $C_5$ alcohol; more preferably methanol, ethanol, propanol, or 2-propanol; still more preferably ethanol. Other useful solvents include amides such as dimethylacetamide. During the oxidation with hydrogen peroxide, the reaction is preferably maintained at less than about 30° C., more preferably less than about 25° C., more preferably less than about 20° C. If desired, sulfinic acid compound 51 can be isolated as the acid or, preferably, as a salt.

Alternatively, 51 can be further used with or without isolation. For example, 51 can be treated with acrolein compound 21 to produce monoalkyl sulfone aldehyde compound 19. The reaction with compound 21 can be done at essentially any convenient temperature, including ambient temperature. The present reaction can also be run in the presence of a solvent. Useful solvents include nitrites such as acetonitrile; aromatic solvents such as benzene, toluene, o-xylene, m-xylene, p-xylene, or mesitylene; or chlorinated solvents such as methylene chloride. In one embodiment, the present reaction is run under biphasic conditions in the presence of tetrabutylammonium iodide.

When $R^6$ is methyl and when $R^1$ is 2-butylacrolein, the product of the sulfone-forming step is butyl sulfone aldehyde 32.

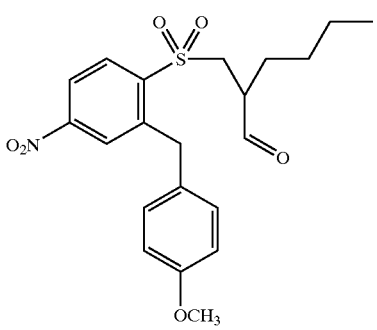

32

Figure 3:
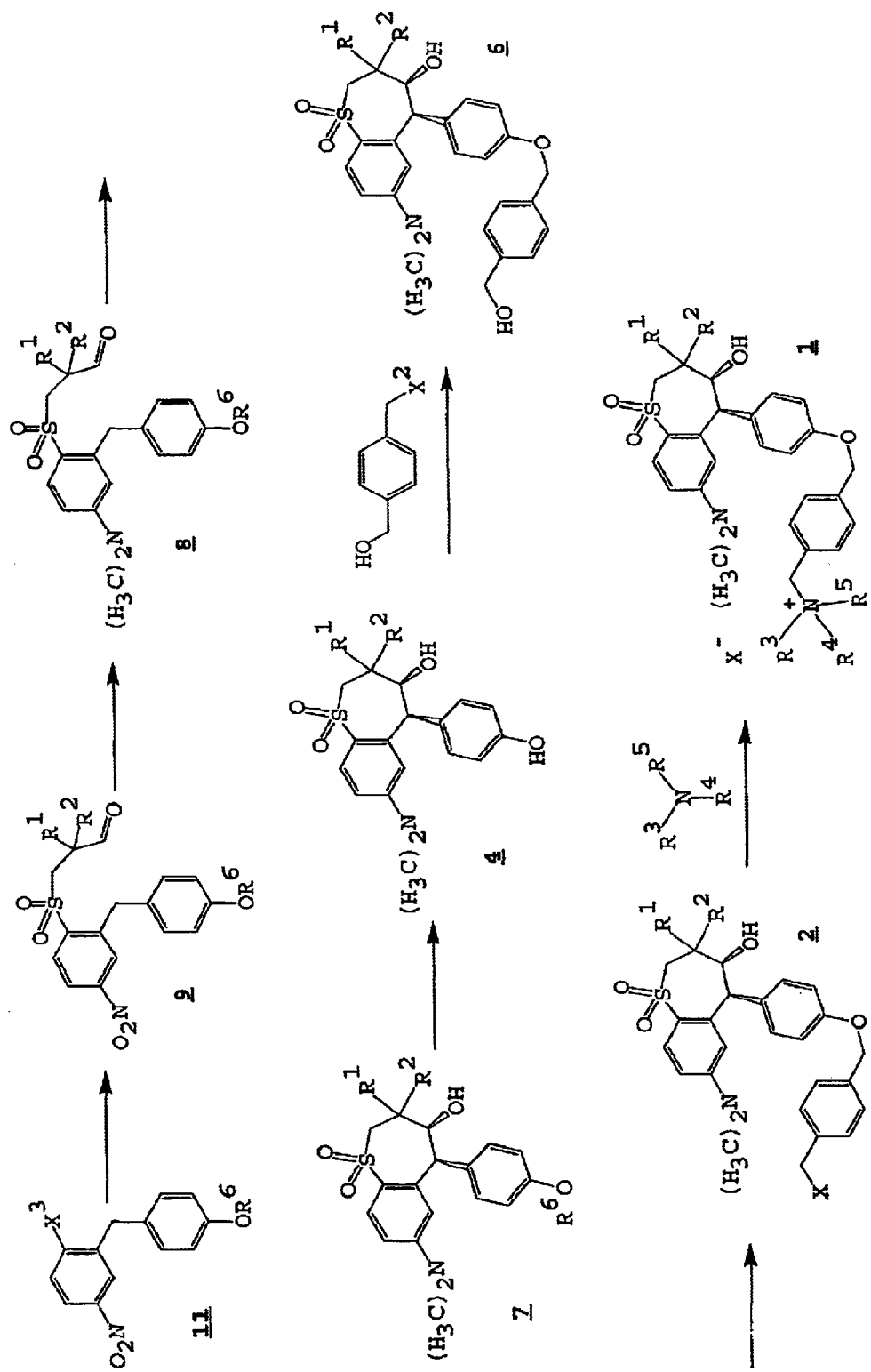
FIG. 3 shows an overall process for the preparation of benzylammonium compound 1.
Figure 4:
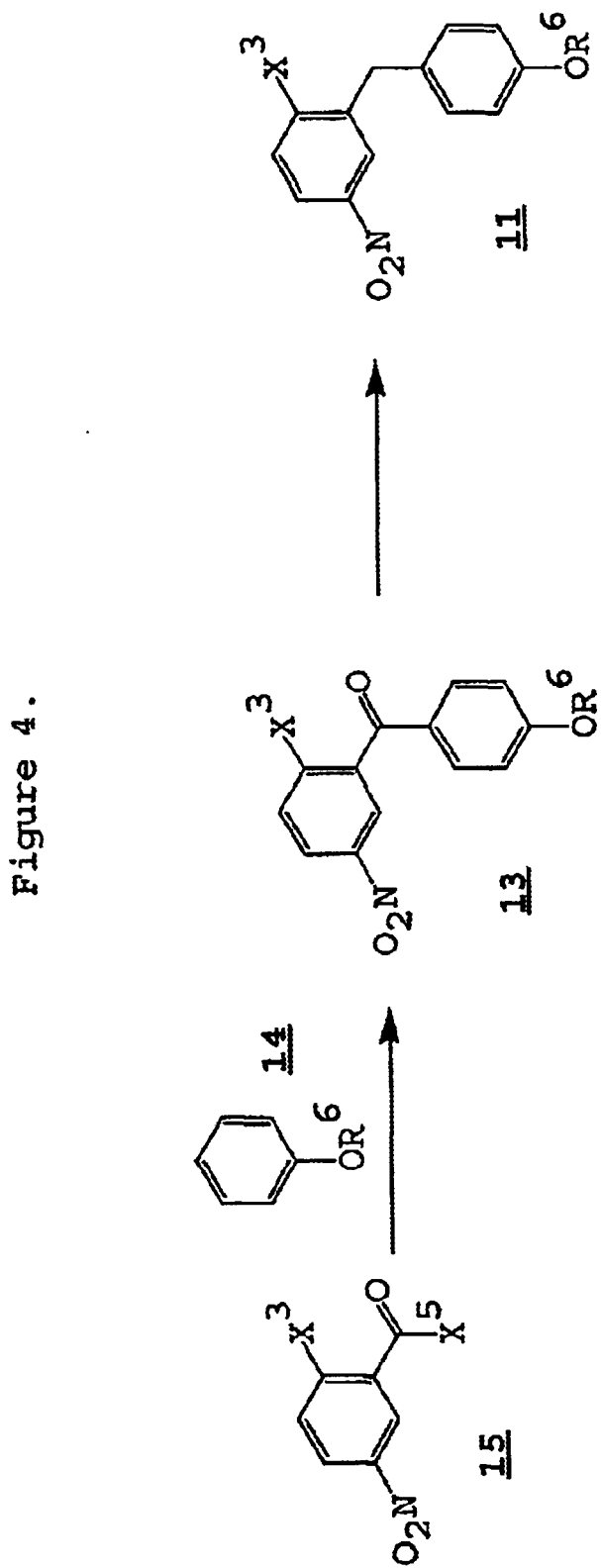
FIG. 4 shows an overall process for the preparation of diphenyl methane compound 11.

The reactions described herein can be run individually, for example to prepare intermediate compounds for storage, use in other reactions, or for commerce. Alternatively two or more of the reactions can be combined. For example, an overall process for the preparation of benzylammonium compound 1 is shown in FIG. 3. Methods and reagents described in this disclosure can be used in the process of FIG. 3. Diphenyl methane compound 11 can, if desired, be prepared by the process shown in FIG. 4, also using methods and reagents described herein.

Figure 5:
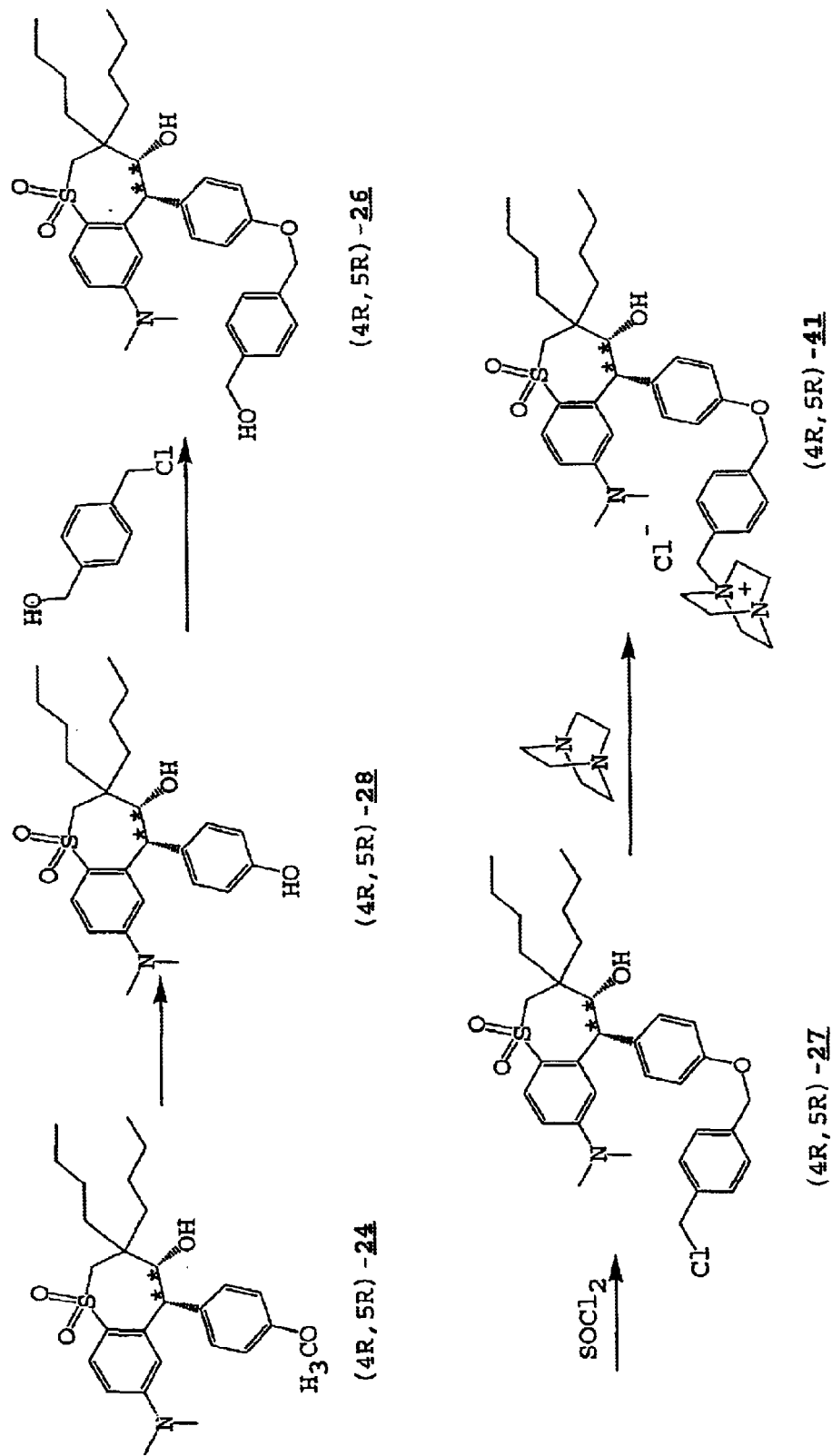
FIG. 5 shows a method in which an enantiomerically enriched tetrahydrobenzothiepine oxide 24 (for example (4R,5R)-24) can be used in combination with the methods of the present invention to prepare an enantiomerically enriched benzylammonium compound.

The methods described herein can also be combined with other reactions in the art and still be within the scope and spirit of the present invention. For example, PCT Patent Application No. WO 99/32478 describes a method of preparing an enantiomerically enriched tetrahydrobenzothiepine oxide such as compound (4R,5R)-24 (Example 9 in WO 99/32478) using an asymmetric oxidizing agent. The process of FIG. 5 shows one of many ways in which an enantiomerically enriched tetrahydrobenzothiepine oxide 24 (for example (4R,5R)-14) can be used in combination with the methods of the present invention to prepare an enantiomerically enriched benzylammonium compound (for example (4R,5R)-1 and more specifically (4R,5R)-41). The enantiomerically enriched compound 24 as used can be prepared as in WO 99/32478 or it can be prepared using methods disclosed hereinbelow. As used herein, asterisks in chemical structures represent chiral centers.

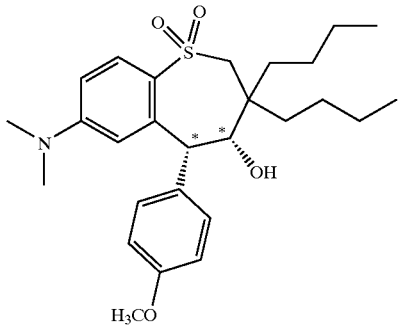

(4R,5R)-24

Other methods can alternatively be used in the process of the present invention to obtain an enantiomerically enriched benzylammonium compound. For example, one of the intermediates or products having one or more chiral centers in FIG. 3 can be optically resolved. An optical resolution is any technique by which an enantiomer of a compound is enriched in concentration relative to another enantiomer of the compound. Useful methods of optical resolution include co-crystallization with a chiral agent, for example as a salt with an optically active counterion, i.e., crystallization of a diastereomeric salt. Another useful technique for the optical resolution of the compounds in the present invention is to derivatize a compound having one or more chiral centers with an optically active derivatizing agent thereby forming a diastereomeric derivative. The diastereomeric derivative can then be separated into its individual diastereomers for example by fractional crystallization or chromatography.

Another method useful for optically resolving intermediates or products in the present process is chiral chromatography. Any of several types of chiral chromatography can be used in the instant invention. For example, the chiral chromatographic technique can include continuous chromatography, semi-continuous chromatography, or single column (batch) chromatography. An example of continuous chromatography is simulated moving bed chromatography (SMB). U.S. Pat. No. 2,985,589, herein incorporated by reference, describes the general theory of SMB. Another reference that describes the general theory of SMB is U.S. Pat. No. 2,957,927, herein incorporated by reference. Still another reference describing SMB is U.S. Pat. No. 5,889,186.

Still another chiral chromatographic technique useful in the present invention is a semi-continuous technique such as closed-loop recycling with periodic intra-profile injection (CLRPIPI). CLRPIPI is described by C. M. Grill in J. Chrom. A, 796, 101–113 (1998).

Single column or batch chromatography is also useful in the present invention for performing the optical resolution.

In any of the chiral chromatographic techniques referenced herein, a variety of conditions can be used. Each of the techniques requires a stationary phase and a mobile phase. The stationary phase can comprise a chiral substrate. For example the chiral substrate can comprise a saccharide or a polysaccharide such as an amylosic, cellulosic, xylan, curdlan, dextran, or inulan saccharide or polysaccharide. The chiral substrate optionally can be on a solid support such as silica gel, zirconium, alumina, clay, glass, a resin, or a ceramic. The chiral substrate can, for example, be absorbed by the solid support, adsorbed onto the solid support, or chemically bound to the solid support. Alternatively, the stationary phase can comprise another chiral substrate such as a tartaric acid derivative. In another alternative, the stationary phase can comprise a derivatized silica sorbent such as a Pirkle sorbent.

The chiral chromatographic technique of the present invention also comprises a mobile phase. Any mobile phase that is capable of differentially partitioning each enantiomer between the stationary phase and the mobile phase is useful in the present invention. For example, the mobile phase can comprise water, an alcohol, a hydrocarbon, a nitrile, an ester, a chlorinated hydrocarbon, an aromatic solvent, a ketone, or an ether. If the mobile phase comprises an alcohol, preferably it is a $C_1$ to about $C_{10}$ alcohol, more preferably a $C_1$ to about $C_8$ alcohol, and more preferably a $C_1$ to about $C_5$ alcohol. If the mobile phase comprises a hydrocarbon, preferably it is a $C_1$ to about $C_{20}$ hydrocarbon, more preferably a $C_1$ to about $C_{15}$ hydrocarbon, and still more preferably a $C_1$ to about $C_{10}$ hydrocarbon. Other useful solvents include acetonitrile, propionitrile, ethyl acetate, methylene chloride, toluene, benzene, xylene, mesitylene, acetone, methyl t-butyl ether, or diethyl ether. Preferably the mobile phase comprises acetonitrile, toluene, or methyl t-butyl ether. The mobile phase can also comprise a mixture of solvents. A preferred mobile phase mixture comprises toluene and methyl t-butyl ether. The mobile phase can also comprise a supercritical fluid such as supercritical $CO_2$.

Carbon dioxide can also be used as a mobile phase in a subcritical state such as liquid $CO_2$. Supercritical or subcritical $CO_2$ can also be used in combination with any of the other mobile phases mentioned above.

The chiral separation can be performed at any convenient temperature, preferably about 5° C. to about 45° C., more preferably about 20° C. to about 40° C.

The optical resolution can be performed on any convenient compound or intermediate having a chiral center in the preparation of the benzylammonium compound. For example, the optical resolution can be performed on any one or more of compounds 1, 2, 4, 6, 7, 8, 9, 10, 12, 35, 36, or 37. In one preferred embodiment, the optical resolution is performed on compound 7. A further preferred embodiment is one in which compound 7 is represented by compound 24, preferably compound syn-24.

Typically in an optical resolution, two enantiomers are partially or essentially completely separated from each other. If the goal of the separation is to obtain an enriched sample of one desired enantiomer, it is useful to have a method of converting or recycling the other enantiomer into the desired enantiomer or into an essentially racemic mixture of enantiomers so that further optical resolution can be performed. Where more than one chiral center exists in a molecule, a plurality of diastereomers can exist. Similarly, diastereomers can be separated to obtain an enriched sample of one or more desired diastereomers. It is further useful to have a method of converting one or more other diastereomers into the desired diastereomer(s) or into a mixture of diastereomers so that further separation can be performed.

Surprisingly, it has been found that this conversion or recycle of stereoisomers can be performed in the process of the present invention. As used herein the word "stereoisomer" includes enantiomer and diastereomer. A method is now disclosed of treating a stereoisomer of a tetrahydrobenzothiepine compound 22

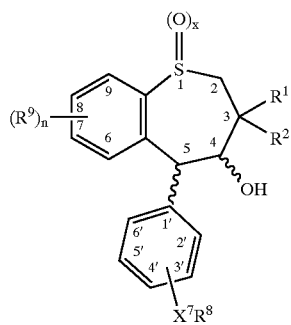

(22)

wherein Formula 22 comprises a (4,5)-stereoisomer selected from the group consisting of a (4S,5S)-diastereomer, a (4R,5R)-diastereomer, a (4R,5S)-diastereomer, and a (4S,5R)-diastereomer, to produce a mixture comprising the (4S,5S)-diastereomer and the (4R,5R)-diastereomer, wherein the method comprises contacting a base with a feedstock composition comprising the (4,5)-stereoisomer of the tetrahydrobenzothiepine compound, thereby producing a mixture of diastereomers of the tetrahydrobenzothiepine compound; and wherein:

$R^1$ and $R^2$ independently are $C_1$ to about $C_{20}$ hydrocarbyl;

$R^8$ is selected from the group consisting of H, hydrocarbyl, heterocyclyl, ((hydroxyalkyl)aryl)alkyl, ((cycloalkyl)alkylaryl)alkyl, ((heterocycloalkyl)alkylaryl)alkyl, ((quaternary heterocycloalkyl)alkylaryl)alkyl, heteroaryl, quaternary heterocycle, quaternary heteroaryl, and quaternary heteroarylalkyl, wherein hydrocarbyl, heterocycle, heteroaryl, quaternary heterocycle, quaternary heteroaryl, and quaternary heteroarylalkyl optionally have one or more carbons replaced by a moiety selected from the group consisting of O, $NR^3$, $N^+R^3R^4A^-$, S, SO, $SO_2$, $S^+R^3A^-$, $PR^3$, $P^+R^3$, $R^4A$, $P(O)R^3$, phenylene, carbohydrate, amino acid, peptide, and polypeptide, and $R^8$ is optionally substituted with one or more moieties selected from the group consisting of sulfoalkyl, quaternary heterocycle, quaternary heteroaryl, $OR^3$, $NR^3R^4$, $N^+R^3R^4R^5A^-$, $SR^3$, $S(O)R^3$, $SO_2R^3$, $SO_3R^3$, oxo, $CO_2R^3$, CN, halogen, $CONR^3R^4$, $SO_2OM$, $SO_2NR^3R^4$, $PO(OR^{23})OR^{24}$, $P^+R^3R^4R^5A^-$, $S^+R^3R^4A^-$, and C(O)OM;

$R^3$, $R^4$, and $R^5$ are as defined above;

$R^{23}$ and $R^{24}$ are independently selected from the substituents constituting $R^3$ and M;

$A^-$ is a pharmaceutically acceptable anion and M is a pharmaceutically acceptable cation;

$R^9$ is selected from the group consisting of H, hydrocarbyl, hydroxyalkyl, alkoxyalkyl, aminoalkyl, alkylaminoalkyl, ammoniumalkyl, polyalkoxyalkyl, heterocyclyl, heteroaryl, quaternary heterocycle, quaternary heteroaryl, $OR^3$, $NR^3R^4$, $N^+R^3R^4R^5A^-$, $SR^3$, $S(O)R^3$, $SO_2R^3$, $SO_3R^3$, oxo, $CO_2R^3$, CN, halogen, NCO, $CONR^3R^4$, $SO_2OM$, $SO_2$ $NR^3R^4$, $PO(OR^{23})OR^{24}$, $P^+R^3R^4R^5A^-$, $S^+R^3R^4A^-$, and C(O)OM;

n is a number from 0 to 4;

$X^7$ is S, NH, or O; and x is 1 or 2.

Preferably the group $X^7R^8$ in compound 22 is in the 3' or the 4' position of the phenyl group, more preferably the 4' position. Preferably $X^7$ is NH or O, more preferably O.

A wide variety of bases can be used to effect the conversion or recycle of stereoisomers of the present invention. For example, the base can be an alkali metal hydroxide, an alkaline earth metal hydroxide, an alkali metal alkoxide, a metal hydride, an alkali metal amide, and an alkali metal hydrocarbyl base. Preferably the base is an alkali metal amide, a metal hydride, or an alkali metal alkoxide. Useful alkali metal amides include lithium diethylamide (IDA), lithium diisopropylamide, lithium N-methylanilide, lithium methylamide, potassium amide, sodamide, and $((CH_3)_3Si)_2NNa$. Useful metal hydrides include lithium hydride, sodium hydride, and calcium hydride. Useful alkali metal alkoxides include for example a lithium alkoxide, a sodium alkoxide, and a potassium alkoxide; preferably a sodium alkoxide or a potassium alkoxide. The alkoxide is preferably a $C_1$ to about $C_{10}$ alkoxide; more preferably a $C_1$ to about $C_6$ alkoxide; still more preferably a $C_1$ to about $C_5$ alkoxide such as a methoxide, an ethoxide, a n-propoxide, an isopropoxide, a n-butoxide, a sec-butoxide, an isobutoxide, a t-butoxide, or a t-amylate. A particularly useful alkoxide is potassium t-butoxide. $R^8$ can be for example H, $C_1$ to about $C_{20}$ alkyl, hydroxyalkylarylalkyl, or heterocycloalkylalkylarylalkyl. Preferably $R^8$ is H, or $C_1$ to about $C_{20}$ alkyl; more preferably $C_1$ to about $C_{20}$ alkyl; still more preferably $C_1$ to about $C_{10}$ alkyl; and more preferably still $C_1$ to about $C_5$ alkyl. In a particularly preferred embodiment $R^8$ is methyl. $R^9$ can for example be H, amino, alkylamino, alkoxy, or nitro; preferably H or alkylamino, more preferably alkylamino, and more preferably still dimethylamino. In a particularly preferred embodiment, $R^9$ is dimethylamino and n is 1. When $R^9$ is dimethylamino and n is 1, it is preferred that $R^9$ be located at the 7-position of the tetrahydrobenzothiepine compound structure. $R^1$ and $R^2$ are as defined above. In one preferred embodiment both of $R^1$ and $R^2$ are butyl. In another preferred embodiment one of one of $R^1$ and $R^2$ is ethyl and the other of $R^1$ and $R^2$ is butyl. It is preferred that the (4,5)-stereoisomer of compound 22 is a (4S,5S) diastereomer, a (4R,5S) diastereomer, or a (4S,5R) diastereomer; more preferably a (4S,5S) diastereomer. The present conversion conditions can also comprise a solvent. Useful solvents include any solvent that is essentially non-reactive toward the base under the reaction conditions. Preferred solvents include ethers such as tetrahydrofuran, diethyl ether, or dioxane; or alcohols such as a $C_1$ to about $C_{10}$ alcohol. If the solvent is an alcohol, preferably it is a $C_1$ to about $C_6$ alcohol; more preferably methanol, ethanol, propanol, isopropyl alcohol, butanol, t-butyl alcohol, or t-amyl alcohol; still more preferably ethanol, t-butyl alcohol, or t-amyl alcohol; and more preferably still t-butyl alcohol. The conversion of the present invention is particularly advantageous when the tetrahydrobenzothiepine compound has the structure of Formula 24.

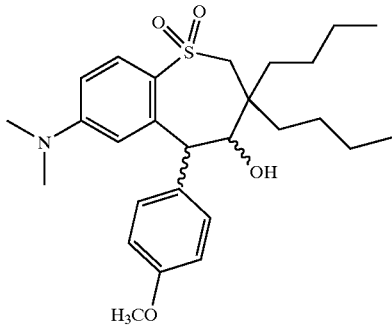

24

The feedstock composition used in the stereoisomeric conversion of the present invention can further comprise amino sulfone aldehyde compound 8 wherein $R^1$, $R^2$, and $R^6$ are as defined above.

An alternate method for the stereoisomeric conversion of the present invention comprises treating compound 22 under elimination conditions to produce a dihydrobenzothiepine compound having the structure of Formula 23

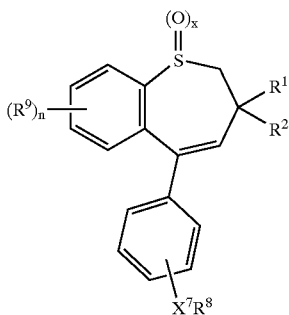

23 and oxidizing the dihydrobenzothiepine compound to produce the mixture of stereoisomers including the (4S,5S)-diastereomer and the (4R,5R)-diastereomer. $R^1$, $R^2$, $R^8$, $R^9$, n, $X^7$, and x are as defined above. The elimination conditions can comprise an acid or the conditions can comprise a base, or the elimination conditions can occur at a neutral pH. The elimination conditions can further comprise derivatizing the diastereomer of a tetrahydrobenzothiepine compound to form a tetrahydrobenzothiepine derivative having an elimination-labile group at the 4-position, and eliminating the elimination-labile group to form the dihydrobenzothiepine compound. The elimination-labile group can be, for example, acid labile or base labile. The elimination-labile group can also be thermally labile. For example, it can be an acetate group or a 3-buten-2-oxy group. The oxidation step can comprise an alcohol-forming step in which the dihydrobenzothiepine compound is reacted under alcohol-forming conditions to produce a mixture of stereoisomers of the tetrahydrobenzothiepine compound. For example the alcohol-formation conditions can comprise oxymercuration-demercuration. In another example, the alcohol-formation conditions can comprise epoxidation followed by reduction using conditions described in PCT Patent Application No. WO 97/33882, herein incorporated by reference. Preferably the (4,5)-stereoisomer is selected from the group consisting of a (4S,5S) diastereomer, a (4R,5S) diastereomer, and a (4S,5R) diastereomer; more preferably a (4S,5S) diastereomer. In a particularly preferred embodiment, the tetrahydrobenzothiepine compound has the structure of compound 24 and the dihydrobenzothiepine compound has the structure of compound 25.

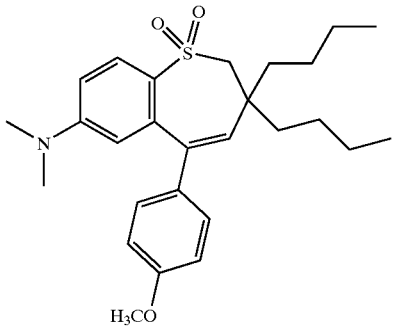

25

It would be particularly useful to have a form of the tetrahydrobenzothiepine compounds that is easily handled, reproducible in form, easily prepared, and that is nonhygroscopic. A hygroscopic compound can absorb water, for example from the ambient atmosphere, and a sample of the compound can gain weight as more water is absorbed. Absorbance of water into a sample of a compound can also affect measurements of the compound, for example, infrared spectra. Hygroscopicity of a pharmaceutical compound can be problematic if that compound absorbs water to an extent and at such a rate that weighing and measurement of the compound is made difficult. Accurate weighing and measurement of a pharmaceutical compound is important to assure that patients receive an appropriate dose. Crystal-forms of the tetrahydrobenzothiepine compounds described herein and particularly of compound 41 are now disclosed.

A first crystal form (Form I) of compound 41 or its enantiomer has a melting point or a decomposition point of about 220° C. to about 235° C., preferably about 228° C. to about 232° C., and more preferably about 230° C. Form I can be prepared, for example, by crystallization of compound 41 or its enantiomer from a solvent that comprises acetonitrile, methanol, or methyl t-butyl ether. Preferably, Form I can be prepared by crystallization of compound 41 or its enantiomer from a solvent comprising methanol or methyl t-butyl ether, and more preferably from a solvent comprising methanol and methyl t-butyl ether. Methods for the preparation of Form I include those described in U.S. Pat. No. 5,994,391, herein incorporated by reference, examples 1426 and 1426a.

Another crystal form (Form II) of compound 41 or its enantiomer has a melting point or a decomposition point of about 278° C. to about 285° C. Form II can be prepared, for example, by crystallization of compound 41 or its enantiomer from a solvent, preferably a ketone solvent, more preferably a ketone solvent comprising methyl ethyl ketone (MEK) or acetone. By way of example, compound 41 or its (4S,5S) enantiomer can be mixed in a solvent comprising MEK and Form II can be induced to crystallize from that solution. Preferably, compound 41 or its (4S,5S) enantiomer is dissolved in a solvent comprising a ketone such as MEK and a quantity of water (for example about 0.5% to about 5% water by weight, preferably 1% to about 4% water by weight, and more preferably 2% to about 4% water by weight). The crystallization can be induced, for example, by evaporating the solvent (e.g., by distillation or by exposure to a stream of a gas such as air or nitrogen for a period of time) or by evaporating the water (e.g. by distillation or azeotroping). Alternatively, the crystallization will be induced by other traditional crystallization methods such as chilling or by addition of another solvent or by addition of a seed crystal. As another alternative, crystallization can be induced by adding additional MEK (decreasing the % by weight of water in the crystallization solvent). Form II can conveniently be caused to precipitate from a reaction mixture in which compound 41 is prepared (e.g., the reaction of (4R,5R)-27 with DABCO) by running that reaction in a solvent comprising MEK, and preferably in a solvent comprising MEK and about 0.5% to about 5% by weight of water. The precipitation can be facilitated by distilling solvent off of the reaction mixture.

Therefore in one embodiment, the present invention provides the tetrahydrobenzothiepine compound in a useful crystalline form. Particularly, the present invention provides a crystalline form (i.e., Form II) of a tetrahydrobenzothiepine compound wherein the tetrahydrobenzothiepine compound has the structure of Formula 71 and wherein the crystalline form has a melting point or a decomposition point of about 278° C. to about 285° C. Preferably, Form II has a melting point or a decomposition point of about 280° C. to about 283° C., and more preferably about 282° C.

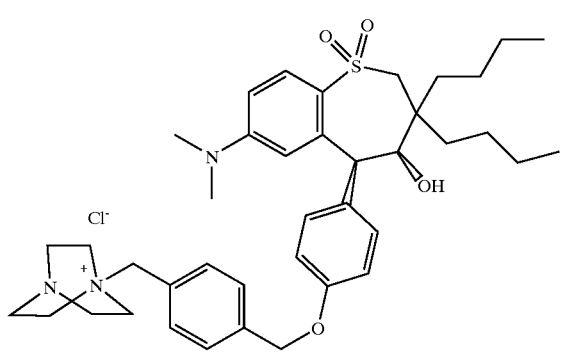

71

Preferably, the compound of Formula 71 has an absolute configuration of (4R,5R) (i.e., compound 41) and this is a preferred absolute configuration for the compound forming the crystal structure of Form II. However, the (4S,5S) enantiomer of compound 71 can also be prepared in the crystalline form of the present invention.

Figure 6:
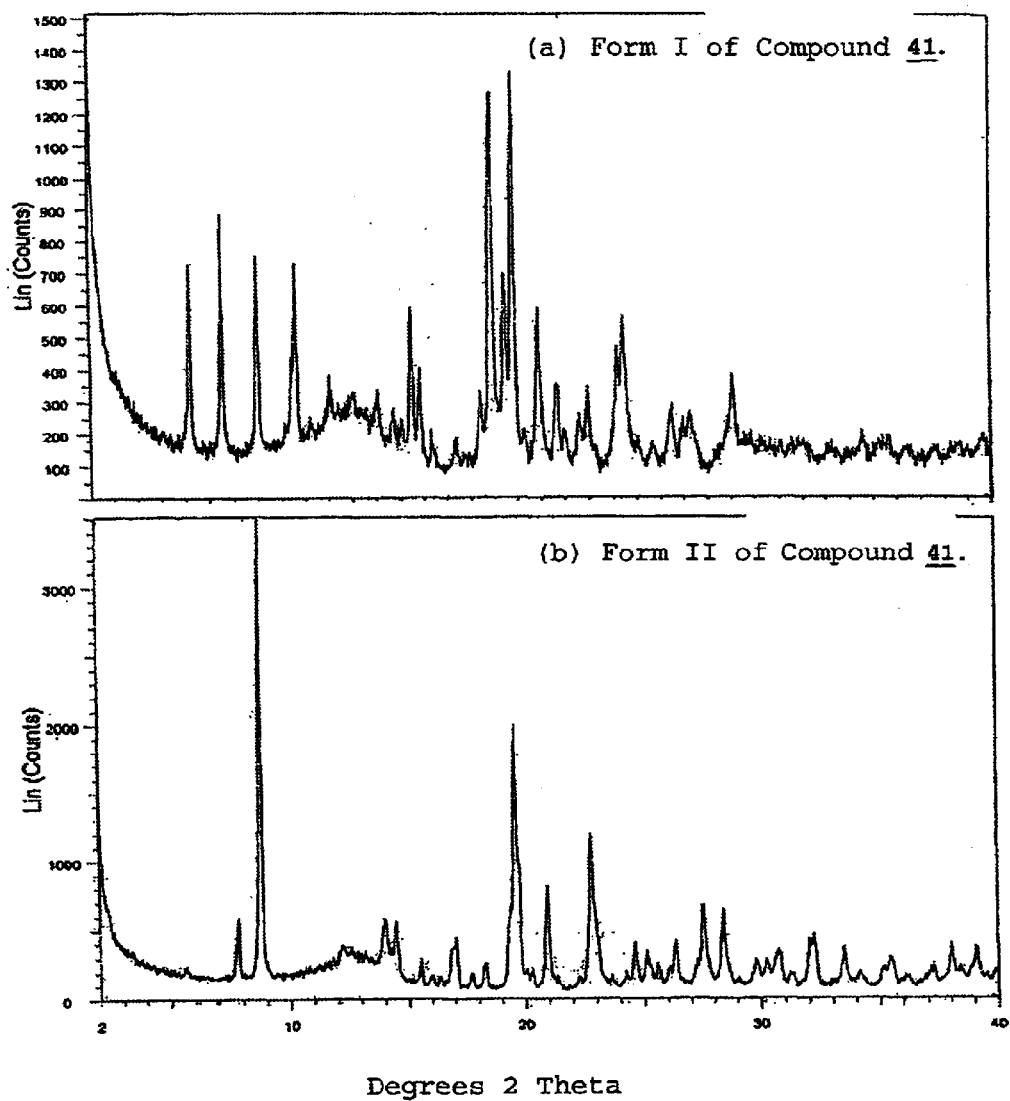
FIG. 6 shows representative X-ray powder diffraction patterns for Form I (plot (a)) and Form II (plot (b)) of compound 41. Horizontal axis values are in degrees 2 theta.

FIG. 6 shows typical X-ray powder diffraction patterns for Form I (plot (a)) and Form II (plot (b)) of compound 41. Preferably the Form II crystalline form has the X-ray powder diffraction pattern shown in FIG. 6, plot (b). Typically, Form II has an X-ray powder diffraction pattern with peaks at about 9.2 degrees 2 theta, about 12.3 degrees 2 theta, and about 13.9 degrees 2 theta. The Form II X-ray powder diffraction pattern typically lacks peaks at about 7.2 degrees 2 theta and at about 11.2 degrees 2 theta. Table 1 shows a comparison of prominent X-ray powder diffraction peaks for Form I and Form II.

Figure 7:
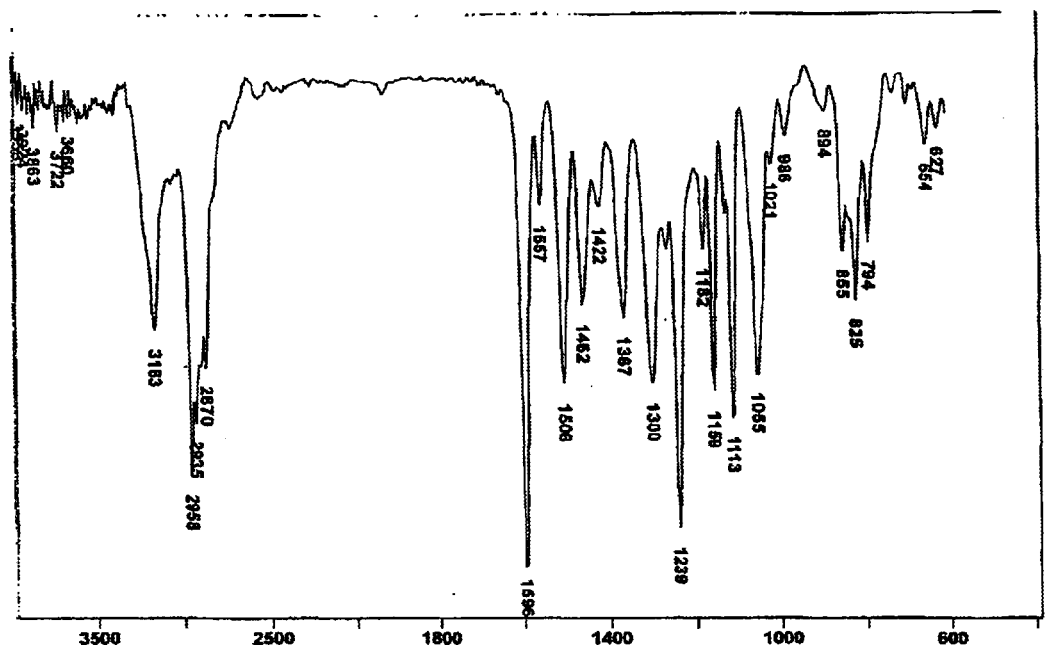
FIG. 7 shows representative Fourier transform infrared (FTIR) spectra for Form I (plot (a)) and Form II (plot (b)) of compound 41. Horizontal axis values are in cm$^{-1}$.
Figure 7:
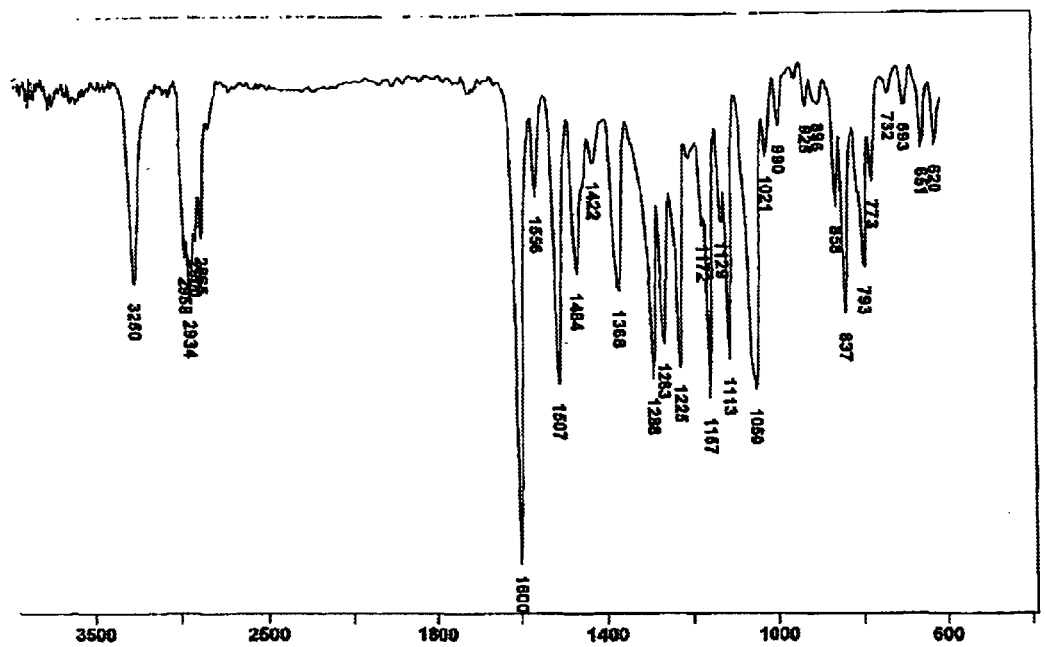

FIG. 7 shows typical Fourier transform infrared (FTIR) spectra for Form I (plot (a)) and Form II (plot (b)) for compound 41. Preferably the Form II crystalline form has the infrared (IR) spectrum shown in FIG. 7, plot (b). Typically, Form II has an IR spectrum with a peak at about 3245 cm$^{-1}$ to about 3255 cm$^{-1}$. Preferably, Form II also has an IR peak at about 1600 cm$^{-1}$. Also preferably, Form II has an IR peak at about 1288 cm$^{-1}$. Table 2 shows a comparison of prominent FTIR peaks for Form I and Form II.

Figure 8:
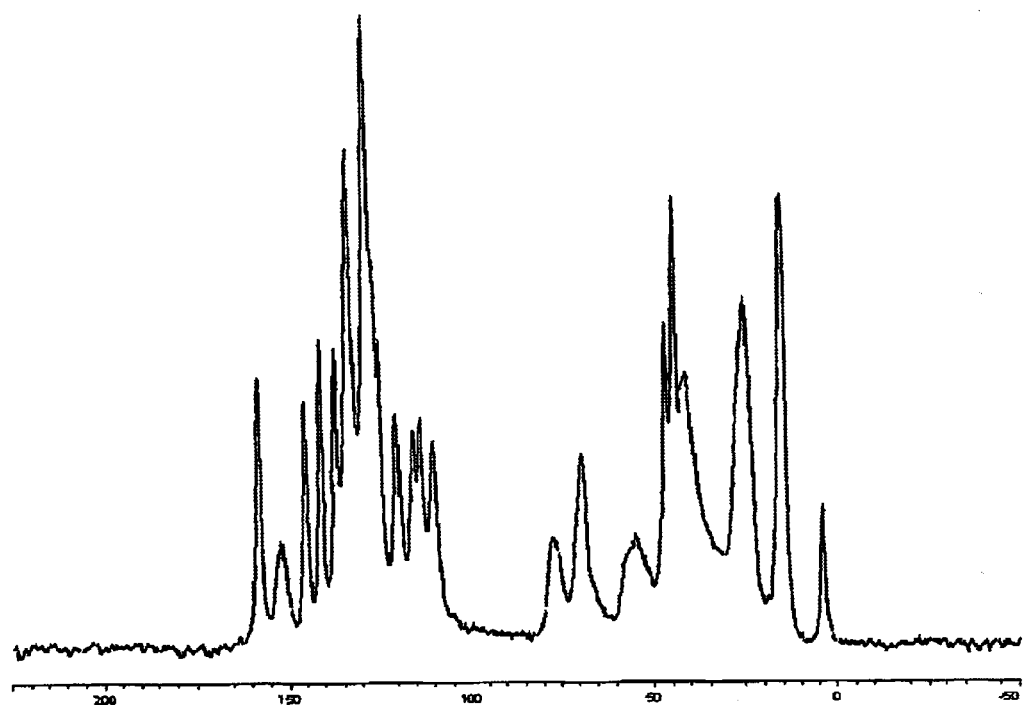
FIG. 8 shows representative solid state carbon-13 nuclear magnetic resonance (NMR) spectra for Form I (plot (a)) and Form II (plot (b)) of compound 41. Horizontal axis values are in ppm.
Figure 8:
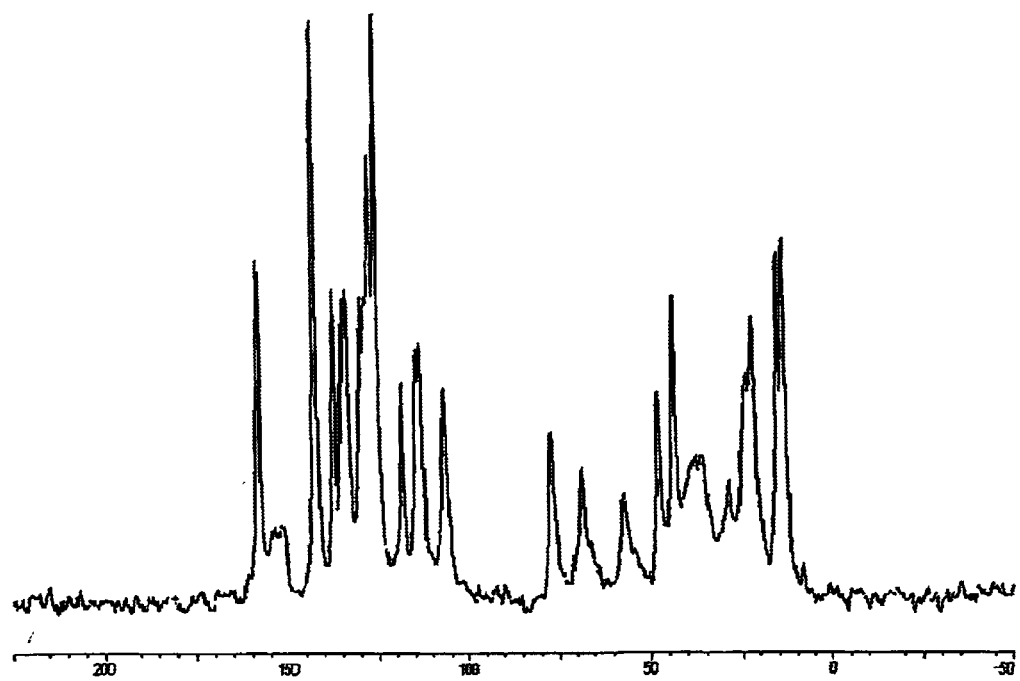

FIG. 8 shows typical solid state carbon-13 nuclear magnetic resonance (NMR) spectra for Form I (plot (a)) and Form II (plot (b)) of compound 41. Preferably the Form II crystalline form has the solid state carbon-13 NMR spectrum shown in FIG. 8, plot (b). Typically, Form II has a solid state carbon-13 NMR spectrum with peaks at about 142.3 ppm, about 137.2 ppm, and about 125.4 ppm. Table 3 shows a comparison of prominent solid state carbon-13 NMR peaks for Form I and Form II.

Figure 9:
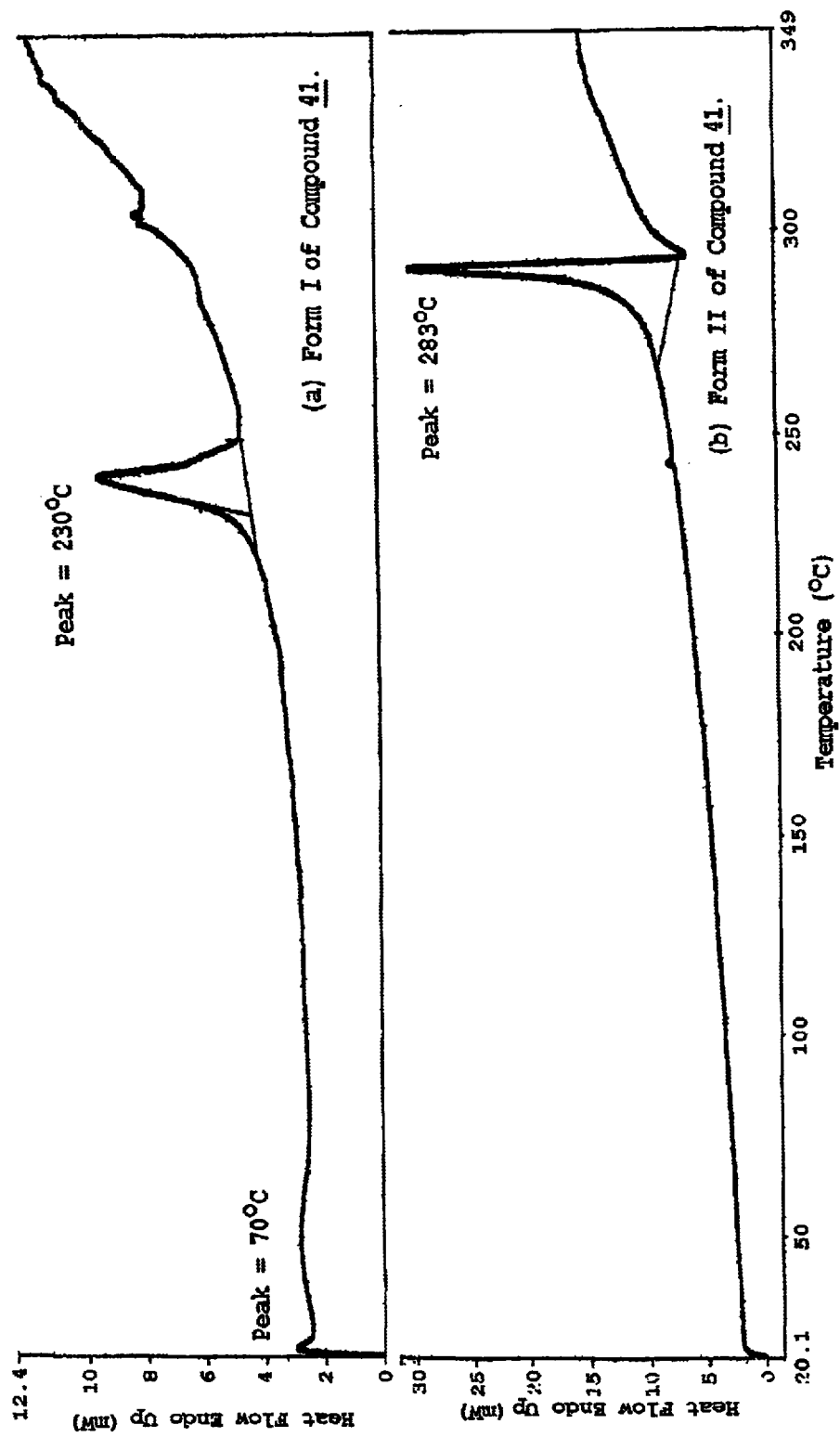
FIG. 9 shows representative differential scanning calorimetry profiles for Form I (plot (a)) and Form II (plot (b)) of compound 41.

FIG. 9 shows typical differential scanning calorimetry profiles for Form I (plot (a)) and Form II (plot(b)) of compound 41.

A dry sample of the crystalline form having a melting point or a decomposition point of about 278° C. to about 285° C. (i.e., Form 11) typically gains less than about 1% of its own weight when equilibrated under 80% relative humidity (RH) air at 25° C. Such a crystalline form is essentially nonhygroscopic. For example, when a sample of Form II crystalline form of compound 41 or an enantiomer thereof is dried at essentially 0% RH at about 25° C. under a purge of essentially dry nitrogen until the sample exhibits essentially no weight change as a function of time, the sample gains less than 1% of its own weight when it is then equilibrated under about 80% RH air at about 25° C. For the present purposes, the term "essentially 0% RH" means less than about 1% RH. The term "equilibrated" means that the change in weight of a sample over time at a given relative humidity is less than 0.0003% ((dm/dt)/m$_0$×100, where m is mass in mg, m$_0$ is initial mass, and t is time in minutes).

The present invention also provides a crystalline form of a tetrahydrobenzothiepine compound wherein the tetrahydrobenzothiepine compound has the structure of Formula 71 wherein the crystalline form is produced by crystallizing the tetrahydrobenzothiepine compound from a solvent comprising methyl ethyl ketone. Preferably in the crystalline form of the present invention, compound 71 has a (4R,5R) absolute configuration; i.e., compound 41. Alternatively, a crystal form of the present invention can be prepared by crystallizing the (4S,5S)-enantiomer of compound 71 from a solvent comprising methyl ethyl ketone.

The present invention provides a method of preparing the crystalline form of the present invention. Particularly, the present invention provides a method for the preparation of a crystalline form of a tetrahydrobenzothiepine compound having the structure of Formula 63

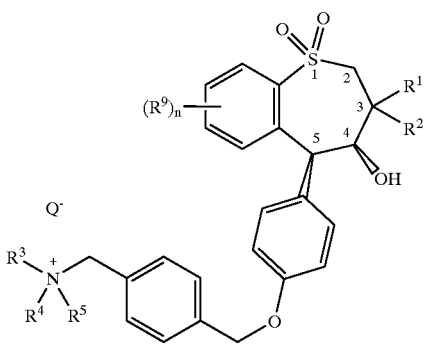

wherein the method comprises crystallizing the tetrahydrobenzothiepine compound from a solvent comprising methyl ethyl ketone, and wherein:

$R^1$ and $R^2$ independently are $C_1$ to about $C_{20}$ hydrocarbyl;

$R^3$, $R^4$, and $R^5$ independently are selected from the group consisting of H and $C_1$ to about $C_{20}$ hydrocarbyl, wherein optionally one or more carbon atom of the hydrocarbyl is replaced by O, N, or S, and wherein optionally two or more of $R^3$, $R^4$, and $R^5$ taken together with the atom to which they are attached form a cyclic structure;

$R^9$ is selected from the group consisting of H, hydrocarbyl, hydroxyalkyl, alkoxyalkyl, aminoalkyl, alkylaminoalkyl, ammoniumalkyl, polyalkoxyalkyl, heterocyclyl, heteroaryl, quaternary heterocycle, quaternary heteroaryl, $OR^3$, $NR^3R^4$, $N^+R^3R^4R^5A^-$, $SR^3$, $S(O)R^3$, $SO_2R^3$, $SO_3R^3$, oxo, $CO_2R^3$, CN, halogen, NCO, $CONR^3R^4$, $SO_2OM$, $SO_2NR^3R^4$, $PO(OR^{23})OR^{24}$, $P^+R^3R^4R^5A^-$, $S^+R^3R^4A^-$, and $C(O)OM$;

$R^{23}$ and $R^{24}$ are independently selected from the substituents constituting $R^3$ and M;

n is a number from 0 to 4;

$A^-$ and $Q^-$ independently are pharmaceutically acceptable anions; and

M is a pharmaceutically acceptable cation.

Preferably in the method of the present invention the tetrahydrobenzothiepine compound has the structure of Formula 64, and more preferably it has the structure of compound 41.

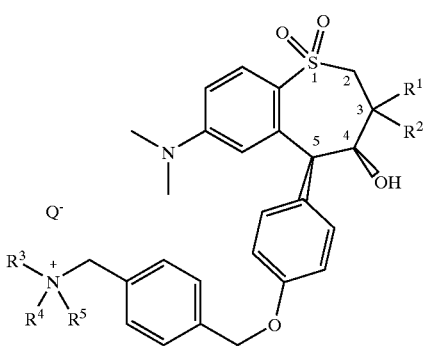

The present invention also provides a crystal form of compound 41 or an enantiomer thereof wherein the crystalline form is produced by crystallizing the tetrahydrobenzothiepine compound or the enantiomer from a solvent comprising a ketone solvent. Preferably the ketone solvent is methyl ethyl ketone, acetone, or methyl isobutyl ketone. More preferably the ketone is methyl ethyl ketone.

Another aspect of the present invention embodies a method for the preparation of Form II ("product crystal form") of compound 41 from Form I ("initial crystal form") of compound 41 wherein the method comprises applying heat to Form I. Accordingly, the present invention provides a method for the preparation of a Form II of a tetrahydrobenzothiepine compound having the compound structure of Formula 41 wherein Form II has a melting point or a decomposition point of about 278° C. to about 285° C., wherein the method comprises applying heat to Form I of the tetrahydrobenzothiepine compound wherein Form I has a melting point or a decomposition point of about 220° C. to about 235° C., thereby forming Form II of compound 41. Conveniently in the present method Form I is heated to a temperature from about 20° C. to about 150° C., preferably about 50° C. to about 125° C., and more preferably about 60° C. to about 100° C. The method can further comprise a cooling step after the step in which Form I is heated. If desired, the conversion of Form I into Form II can be performed in the presence of a solvent. For example, the conversion can be performed on a slurry of Form I mixed with a solvent. The solvent can comprise essentially any convenient solvent. Preferably the solvent comprises a ketone, and more preferably the ketone is methyl ethyl ketone, acetone, or methyl isobutyl ketone. More preferably still the ketone is methyl ethyl ketone. However, the conversion can if desired be performed in acetone. Alternatively, the conversion can be performed in methyl isobutyl ketone.

Although the discussion and examples of this application illustrate the preparation of tetrahydrobenzothiepine oxides having a para-substituted phenyl group at the 5-position of the benzothiepine ring, tetrahydrobenzothiepine oxides having a meta-substituted phenyl group at the 5-position can be prepared in a similar manner by selection of the proper starting materials. For example, use of a meta-substituted phenyl analog of a compound of Formula 7 in the applicable processes of the present application would yield the corresponding tetrahydrobenzothiepine oxide having a meta-substituted phenyl group at the 5-position. The preparation of selected suitable starting materials is disclosed in U.S. Pat. No. 5,994,391 (such as described in Examples 1398a, 1400, 1425, 1426 and 1426a).

c. Detailed Preparative Methods

The starting materials for use in the methods of preparation of the invention are known or can be prepared by conventional methods known to a skilled person or in an analogous manner to processes described in the art.

Generally, the process methods of the present invention can be performed as follows.

EXAMPLE 1

Preparation of 1-chloro-2-(4-methoxyphenyl)
methyl-4-nitrobenzene, 33

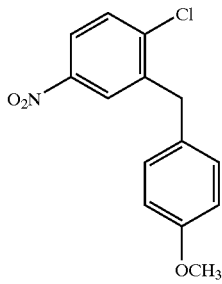

Step A. Preparation of 2-chloro-5-nitrophenyl-4'-methoxyphenyl ketone, 34.

Method 1.

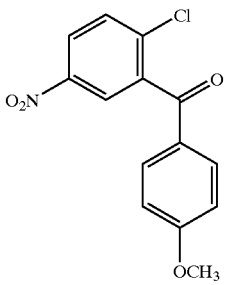

In an inert atmosphere, weigh out 68.3 g of phosphorus pentachloride (0.328 mole, Aldrich) into a 2-necked 500 mL round bottom flask. Fit the flask with a $N_2$ inlet adapter and suba seal. Remove from the inert atmosphere and begin $N_2$ purge. Add 50 mL of anhydrous chlorobenzene (Aldrich) to the $PCl_5$ via syringe and begin stirring with a magnetic stir bar.

Weigh out 60 g of 2-chloro-5-nitrobenzoic acid (0.298 mole, Aldrich). Slowly add the 2-chloro-5-nitrobenzoic acid to the chlorobenzene solution while under $N_2$ purge. Stir at room temperature overnight. After stirring at room temperature for about 20 hrs, place in an oil bath and heat at 50° C. for 1 hr. Remove chlorobenzene under high vacuum. Wash the residue with anhydrous hexane. Dry the acid chloride (wt=61.95 g). Store in inert and dry atmosphere.

In an inert atmosphere, dissolve the acid chloride in 105 mL of anhydrous anisole (0.97 mole, Aldrich). Place solution in a 2-neck 500 mL round bottom flask.

Weigh out 45.1 g of aluminum trichloride (0.34 moles, Aldrich) and place in a solid addition funnel. Fit the reaction flask with an addition funnel and a $N_2$ inlet adapter. Remove from inert atmosphere. Chill the reaction solution with an ice bath an begin the $N_2$ purge. Slowly add the $AlCl_3$ to the chilled solution. After addition is complete, allow to warm to room temperature. Stir overnight.

Quench the reaction by pouring into a solution of 300 mL 1N HCl and ice. Stir for 15 min. Extract twice with ether. Combine the organic layers and extract twice with 2% NaOH, then twice with deionized $H_2O$. Dry over $MgSO_4$, filter, and rotovap to dryness. Remove the anisole under high vacuum. Crystallize the product from 90% ethanol/10% ethyl acetate. Dry on a vacuum line. Wt=35.2 g. yield 41%. Mass spec (m/z=292).

Method 2.

Change 230 kg of 2-chloro-5-nitrobenzoic acid (CNBA) to a clean dry reactor flushed with $N_2$. Seal the reactor and flush with $N_2$. To the reactor charge 460 kg of anisole. Start agitation and heat the mixture to 90° C., dissolving most of the CNBA. To the reactor charge 785 kg of polyphosphoric acid (PPA). PPA containers are warmed in a hot box (70° C.) prior to charging in order to lower viscosity. Two phases result. The upper phase contains the majority of the CNBA and anisole. The lower phase contains most of the PPA. The reaction conditions are maintained for 5 hr at which time sampling begins to determine residual CNBA. Analysis of samples is by gas chromatography. The reaction is quenched when 1.0% residual CNBA is achieved. The reaction is quenched into 796 kg $H_2O$. The temperature of the quenched mass is adjusted to 60° C. and maintained at this temperature until isolation. Agitation is stopped and the phases are split. The lower spent acid phase is sent to waste disposal. The upper product phase is washed with 18 kg of sodium bicarbonate in 203 kg of water, then washed with 114 kg of potable water. Agitation is stopped and the phases are split. The upper aqueous phase is sent to waste disposal. The lower product phase is cooled to about 0° C. and 312 kg of heptane is added. A mixture of ortho- and para-substituted product (total 10 kg) precipitates out of solution and is recovered by pressure filtration. To the product phase is added another 134 kg of heptane causing another 317 kg of a mixture of ortho- and para-substituted product to precipitate. The precipitate is recovered by pressure filtration. The wetcake is washed with heptane to remove residual anisole. The wetcake is dried in a rotary vacuum dryer at 60° C. Final yield of 34 is 65.1% (30.3% yield of the ortho-substituted product).

Step B. Preparation of 1-chloro-2-(4-methoxyphenyl) methyl-4-nitrobenzene, 33.

To a clean dry nitrogen purged 500 mL round bottom flask was charged 60.0 g (0.206 moles) of 34. Trifluoroacetic acid (100 grams, ca. 67 mL) was added to the reactor and the resulting suspension was heated to 30° C. to give a homogeneous wine colored solution. Next, 71.0 g (0.611 moles) of triethylsilane was placed in an addition funnel and 1.7 g (0.011 moles) of trifluoromethanesulfonic acid (triflic acid) was added to reactor. The color changed from burgundy to greenish brown. Triethylsilane was added dropwise to the solution at 30° C. The batch color changed to a grass green and an exothermic reaction ensued. The exotherm was allowed to raise the batch temperature to 45° C. with minimal cooling in a water bath. The reaction temperature was controlled between 45–50° C. for the duration of addition. Addition of triethylsilane was complete in 1 hour. The batch color became greenish brown at completion. The batch was stirred for three more hours at 40° C., then allowed to cool. When the batch temperature reached ca. 30° C., product started to crystallize. The batch was further cooled to 1–2° C. in a water/ice bath, and after stirring for another half hour at 1–2° C., the slurry was filtered. The crystalline solid was washed with two 60 mL portions of hexane, the first as a displacement wash and the second as a reslurry on the filter. The solids were vacuum filtered until dry on the filter under a stream of nitrogen and the solids were then transferred to a clean container. A total of 49.9 grams of material was isolated. Mp 87.5–90.5° C. and HNMR identical with known samples of 33. GC (HP-5 25 meter column, 1 mL $N_2$/min at 100° C., FID detection at 300° C., split 50:1) of the product showed homogeneous material. The isolated yield was 88% of 33.

EXAMPLE 2

Preparation of 2,2-dibutyl-1,3-propanediol, 54

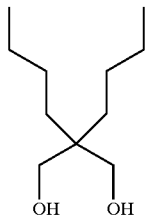

54

(This method is similar to that described in U.S. Pat. No. 5,994,391, Example Corresponding to Scheme XI, Step 1, column 264.) Lithium aluminum hydride (662 ml, 1.2 equivalents, 0.66 mol) in 662 mL of 1M THF was added dropwise to a stirred solution of dibutyl-diethylmalonate (150 g, 0.55 mol) (Aldrich) in dry THF (700 ml) while maintaining the temperature of the reaction mixture at between about −20?C to about 0?C using an acetone/dry ice bath. The reaction mixture was then stirred at room temperature overnight. The reaction was cooled to −20?C and 40 ml of water, 80 ml of 10% NaOH and 80 ml of water were successively added dropwise. The resulting suspension was filtered. The filtrate was dried over sodium sulfate and concentrated under vacuum to give 98.4 g (yield 95%) of the diol as an oil. Proton NMR, carbon NMR and MS confirmed the product.

Alternate reducing agents that will be useful in this preparation of compound 54 include diisobutylaluminum hydride (DIBAL-H) or sodium bis(2-methoxyethyxy) aluminum hydride (for example, Red-Al supplied by Aldrich).

EXAMPLE 3

Preparation of 1-bromo-2-butyl-2-(hydroxymethyl)hexane, 52

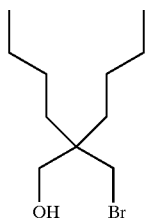

52

A 250 mL 3-necked round-bottomed flask was fitted with a mechanical stirrer, a nitrogen inlet, an addition funnel or condenser or distilling head with receiver, a thermocouple connected to a J-Kem temperature controller and a thermocouple connected to analog data acquisition software, and a heating mantle. The flask was purged with nitrogen and charged with 20 grams of 54. To this was added 57 grams of a 30 wt. % solution of HBr in acetic acid. The mixture was heated to 80° C. for 4 hrs. The solvents were distilled off to a pot temperature of 125° C. over 20 minutes. This removes most of the residual HBr. The mixture was cooled to 80° C. and 100 mL of Ethanol 2B (source: Aaper) was added at once. Next 1.0 mL of concentrated sulfuric acid was added. The solvent was distilled off (10 to 15 ml solvent at 79–80° C.). And the mixture was refluxed for 2 h. An additional 10 to 15 ml of solvent was distilled off and the mixture was again held at reflux temperature for 2 h. Further solvent was distilled off to a pot temperature of 125° C. and then the flask contents were cooled to 25.0° C. To the flask was added 100 mL of ethyl acetate and 100 mL of 2.5N sodium hydroxide. The mixture was agitated for 15 minutes and the aqueous layer was separated. Another 100 mL of water was added to the pot and the contents were agitated 15 minutes. The aqueous layer was separated and solvent was distilled off to a pot temperature of 125° C. During this process water is removed by azeotropic distillation with ethyl acetate. The product was concentrated under reduced pressure to afford 26.8 g of a brown oil containing the product 52 (96.81% by GC: HP1 column; initial temp. 50° C., hold for 2.5 min, Ramp 10° C./min to ending temp. 275° C., final time 15 min).

Example 3a

Alternate Preparation of 1-bromo-2-butyl-2-(hydroxymethyl)hexane, 52

A 250 mL 3-necked round-bottomed flask is fitted with a mechanical stirrer, a nitrogen inlet, an addition funnel or condenser or distilling head with receiver, a thermocouple connected to a J-Kem temperature controller and a thermocouple connected to analog data acquisition software, and a heating mantle. The flask is purged with nitrogen and charged with 20 grams of 54. To this is added 57 grams of a 30 wt. % solution of "Br in acetic acid. The mixture is heated to 80° C. for 4 hrs. The solvents are vacuum distilled off to a pot temperature of 90° C. over 20 minutes. This removes most of the residual HBr. The mixture is cooled to 80° C. and 100 mL of Ethanol 2B (source: Aaper) is added at once. Next 1.0 mL of concentrated sulfuric acid is added. The solvent is distilled off (10 to 15 ml solvent at 79–80° C.). And the mixture is refluxed for 2 h. An additional 10 to 15 ml of solvent is distilled off and the mixture is again held at reflux temperature for 2 h. Further solvent is distilled off to a pot temperature of 85° C. and then the flask contents are cooled to 25.0° C. To the flask is added 100 mL of ethyl acetate and 100 mL of 2.5N sodium hydroxide. The mixture is agitated for 15 minutes and the aqueous layer is separated. Another 100 mL of water is added to the pot and the contents are agitated 15 minutes. The aqueous layer is separated and solvent is distilled off to a pot temperature of 85° C. During this process water is removed by azeotropic distillation with ethyl acetate. The material is concentrated under reduced pressure to afford the product 52.

EXAMPLE 4

Preparation of 2-(bromomethyl)-2-butylhexanal

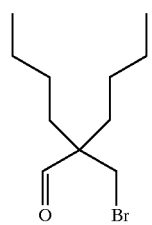

53

A 500 mL 3-necked round-bottom flask was fitted with a mechanical stirrer, a nitrogen inlet, an addition funnel or condenser or distilling head with receiver, a thermocouple connected to a J-Kem temperature controller and a thermocouple connected to analog data acquisition software, and a heating mantle. The flask was purged with nitrogen gas and charged with 26.0 grams of 52 and 15.6 grams of triethylamine. In a 250 ml flask was slurried 37.6 grams of sulfur trioxide-pyridine in 50 mL of DMSO. The DMSO slurry was added to the round-bottom flask by addition funnel over 15 min. The addition temperature started at 22° C. and reached a maximum of 41.0° C. (Addition of the slurry at temperatures below 18.0° C. will result in a very slow reaction, building up sulfur trioxide with will react rapidly when the temperature rises above 25° C.) The mixture was stirred for 15 minutes. To the mixture was added 100 mL of 2.5M HCl over 5 minutes. The temperature was maintained below 35° C. Next, 100 mL of ethyl acetate was added and the mixture was stirred 15 minutes. The mixture was then cooled to ambient and the aqueous layer was separated. To the pot was added 100 mL of water and the mixture was agitated for 15 minutes. The aqueous layer was separated. The solvent was distilled to a pot temperature of 115° C. and the remaining material was concentrated under reduce pressure to afford 21.8 g of a brown oil containing the product 53 (95.1% by GC: HP1 column; initial temp. 50° C., hold for 2.5 min, Ramp 10° C./min to ending temp. 275° C., final time 15 min).

Example 4a

Alternate Preparation and Purification of 2-(Bromomethyl)-2-butylhexanal, 53 a. Preparation of Compound 52

To the reactor is charged 2,2-dibutyl-1,3-propanediol followed by 30 wt % HBr in acetic acid. The vessel is sealed and heated at an internal temperature of ca. 80° C. and held for a period of ca. 7 hours, pressure maintained below 25 psia. A GC of the reaction mixture is taken to determine reaction completion (i.e., conversion of 2,2-dibutyl-1,3-propanediol into 3-acetoxy-2,2-dibutyl-1-propanol). If the reaction is not complete at this point, the mixture may be heated for an additional period of time to complete the conversion. Acetic acid/HBr is then removed using house vacuum (ca. 25 mmHg) up to a maximum internal temperature of ca. 90° C. Ethanol is then added followed by sulfuric acid. A portion of the ethanol is removed (ca. one-quarter of the ethanol added) via atmospheric distillation. Ethanol is then added back (ca. the amount removed during the distillation) to the reactor containing the 3-acetoxy-2,2-dibutyl-1-propanol and the contents are heated to reflux (ca. 80° C. with a jacket temperature of 95° C.) and then held at reflux for ca. 8 hours. Ethanol is then removed via atmospheric distillation up to a maximum internal temperature of 85° C., using a jacket temperature of 95° C. A GC is taken to determine reaction completion (i.e., conversion of 3-acetoxy-2,2-dibutyl-1-propanol to compound 52). If the reaction is not complete, ethanol is added back to the reactor and the contents are heated to reflux and then held at reflux for an additional 4 hours (ca. 80° C., with a jacket of 95° C.). Ethanol is then removed via atmospheric distillation up to a maximum internal temperature of 85° C., using a jacket temperature of 95° C. A GC is taken to determine reaction completion (i.e., conversion of 3-acetoxy-2,2-dibutyl-1-propanol to compound 52). Once the reaction is deemed to be complete, the remaining ethanol is removed via atmospheric distillation up to a maximum internal temperature of 125° C. Methyl t-butyl ether is then added followed by a 5% sodium bicarbonate solution. The layers are separated, the aqueous layer is extracted once with MTBE, the organic extracts are combined, washed once with water, dried over $MgSO_4$, and concentrated under house vacuum (ca. 25 mmHg) to a maximum internal temperature of 60° C. The resultant oil is stored in the cooler until it is needed for further processing.

b. Preparation of Compound 53.

Methyl sulfoxide is charged to the reactor followed by compound 52 and triethylamine. Pyridine-sulfur trioxide complex is then added portion-wise to the reactor while maintaining an internal temperature of <35° C. Once the pyridine-sulfur trioxide complex addition is complete, a GC of the reaction mixture is taken to determine reaction completion (i.e., conversion of 52 into 53). If the reaction is not complete at this point, the mixture may be stirred for an additional period of time to complete the conversion. The reaction is quenched with an 11 wt % aqueous HCl solution. Ethyl acetate is added and the layers are separated, the aqueous layer is extracted once with ethyl acetate, the organic extracts are combined, washed once with water, dried over $MgSO_4$, and concentrated under house vacuum (ca. 25 mm/Hg) to a maximum internal temperature of 30° C. The resultant oil is stored in the cooler until it is needed for further processing.

c. Alternate Preparation of Compound 53.

Compound 52 and methylene chloride are charged to the reactor followed by TEMPO. The solution is cooled to ca. 0–5° C. Potassium bromide and sodium bicarbonate are dissolved in a separate reactor and added to the solution of 52 and TEMPO at 0–5° C. The biphasic mixture is cooled to 0–5° C. and sodium hypochlorite is added at such a rate to maintain an internal temperature of 0–5° C. When the add is complete a GC of the reaction mixture is performed to determine reaction completion. If the reaction is not complete (>1% 52 remaining), additional sodium hypochlorite may be added to drive the reaction to completion. Immediately after the reaction is determined to be complete, an aqueous solution of sodium sulfite is added to quench the remaining sodium hypochlorite. The layers are separated, the aqueous layer is back-extracted with methylene chloride, the combined organic fractions are washed and dried over sodium sulfate. Compound 53 is then concentrated via a vacuum distillation, up to a maximum internal temperature of ca. 30° C. The crude aldehyde is stored in the cooler until it is required for further processing.

d. Purification of Compound 53.

A Wiped Film Evaporated (WFE) apparatus is set up with the following conditions: evaporator temperature of 90° C., vacuum of ca. 0.2 mmHg and a wiper speed of 800 rpm's. The crude compound 53 is fed at a rate of 1.0–1.5 kilograms of crude per hour. The approximate ratio of product to residue during distillation is 90:10.

EXAMPLE 5

Preparation of 1-(2,2-dibutyl-S,S-dioxido-3-oxopropylthio)-2-((4-methoxyphenyl)methyl)-4-nitrobenzene, 30

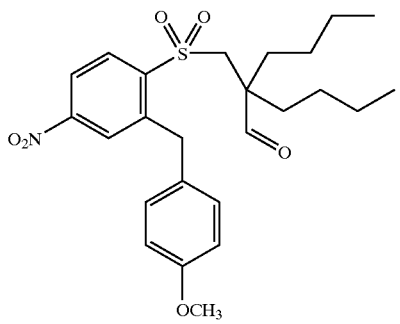

A 1000 mL 4 neck jacketed Ace flask was fitted with a mechanical stirrer, a nitrogen inlet, an addition funnel or condenser or distilling head with receiver, a thermocouple, four internal baffles and a 28 mm Teflon turbine agitator. The flask was purged with nitrogen and charged with 75.0 grams of 33. Next, the flask was charged with 315.0 grams' of dimethylacetamide (DMAC), agitation was started and the mixture was heated to 30° C. Sodium sulfide (39.2 grams) was dissolved in 90 ml water in a separate flask. The aqueous sodium sulfide solution was charged into the flask over a 25 minute period. Temperature reached 37° C. at completion of addition. The solution turned dark red immediately and appeared to form a small amount of foam-like globules that adhered to the wall of the reactor. The temperature was held for two hrs at 40° C. To the flask was charged 77.9 grams of 53 all at once. The reaction mixture was heated to 65° C. and held for 2 hrs. Next 270 ml water was added at 65° C. The mixture was agitated 15 minutes. To the flask was then charge 315 ml of benzotrifluoride and the mixture was agitated 15 minutes. The aqueous layer was separated at 50° C. The organic layer was washed with 315 ml of 3% sodium chloride solution. The aqueous layer was separated at 50° C. The solvent was distilled to a pot temperature of 63° C. at 195 to 200 mmHg. The flask contents were cooled to 60° C. and to it was charged 87.7 grams of trimethyl orthoformate, and 5.2 grams of p-toluenesulfonic acid dissolved in 164.1 mL of methanol. The mixture was heated to reflux, 60 to 65° C. for 2 hours. The solvent was distilled to a pot temperature of 63° C. at 195 to 200 mmHg to remove methanol and methylformate. The flask was then charged with 252 ml benzotrifluoride and then cooled to 15° C. Next 22.2 grams sodium acetate as a slurry in 30 ml water was added to the flask. The flask was then charged with 256.7 grams of commercial peracetic acid (nominally 30–35% assay) over 20 minutes, starting at 15° C. and allowing the exotherm to reach 30 to 35° C. The addition was slow at first to control initial exotherm. After the first equivalent was charged the exotherm subsided. The mixture was heated to 30° C. and held for 3 hours. The aqueous layer was separated at 30° C. The organic layer was washed with 315 ml 6% sodium sulfite. The aqueous layer was separated. The flask was then charged with 40% by wt. sulfuric acid and heated to 75° C. for 2 hrs. The aqueous layer was separated from the bottom at 40 to 50° C. To the flask was added 315 ml saturated sodium bicarbonate and the contents were stirred for 15 minutes. The aqueous layer was separated. The solvent was distilled to a reactor temperature of 63° C. at 195 to 200 mmHg. Next, 600 ml isopropyl alcohol was charged over 10 minutes and the temperature was maintained at 50° C. The reactor was cooled to 38° C. and held for 1 hour. (The product may oil slightly at first then crystallize during the hold period. If product oils out at 38° C. or does not crystallize it should be seeded to promote crystallization before cooling.) The reactor was cooled to 15° C. over 30 minutes then held for 60 minutes. The solids were filtered and dried to yield 102.1 grams of a crystalline yellow solid. Wash with 150 ml 10° C. IPA. Analysis by HPLC (Zorbax RX-C8 column, 0.1% aq. TFA/acetonitrile gradient mobile phase, UV detection at 225 nm) showed 97.7% by weight of 30, 79.4% isolated molar corrected yield.

Example 5a

Alternate Preparation of 1-(2,2-dibutyl-S,S-dioxido-3-oxopropylthio)-2-((4-methoxyphenyl)methyl)-4-nitrobenzene, 30

Step 1. Preparation of Sulfide Aldehyde Compound 69.

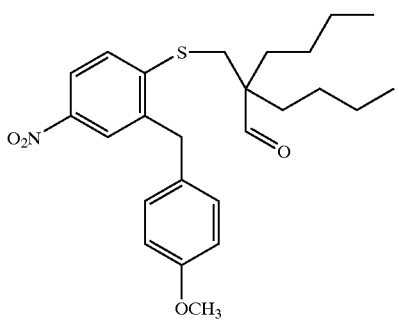

A 1000 mL 4 neck jacketed Ace reator is fitted with a mechanical stirrer, nitrogen inlet, additional funnel, a thermocouple, four internal baffles, and a 28 mm Teflon turbine agitator. The flask is purged with nitrogen gas and charged with 145 g of compound 33 and 609 mL of N,N-dimethylacetamide (DMAC). Agitation is started and the mixture is heated to 30° C. In a separate flask 72.3 g of $Na_2S$ (Spectrum) is dissolved in 166.3 mL of water. The aqueous $Na_2S$ is charged to the flask over a period of about 90 minutes. Addition rate should be adjusted to maintain the reaction temperature below 35° C. The mixture is stirred at 35° C. for 2 hours and then 150.7 g of compound 53 is added all at once. The mixture is heated to 70° C. and held for 2 hours. To the mixture is adjusted to 50° C., to it is added 442.7 mL water and the mixture is agitated for 15 minutes. To the reactor is then charged 609 mL of benzotrifluoride followed by 15 minutes of agitation. The aqueous layer is separated at 50° C. The organic layer is washed with 3% aq. NaCl. The aqueous layer is separated at 50° C. The organic layer contains compound 69. The organic layer is stable and can be held indefinitely.

Step 2. Preparation of Compound 70.

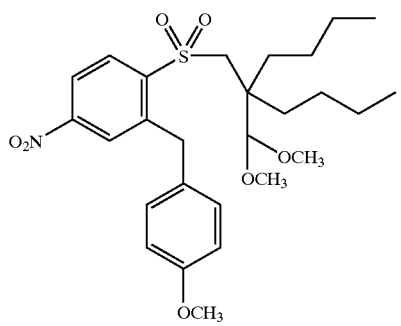

The solvent is distilled at about 63° C. to 66° C. and 195 to 200 mmHg from the organic layer resulting from Step 1 until a third to a half of the benzotrifluoride volume is distilled. The mixture is cooled to about 60° C. and charged with 169.6 g of trimethylorthoformate and about 10 g of p-toluenesulfonic acid dissolved in 317.2 mL of methanol. (Note: alternate orthoformates, for example triethylorthoformate, can be used in place of trimethylorthoformate to obtain other acetals.) The reactor is fitted with a condenser add a distillation head. The mixture is heated to boiling and from it is distilled 5 mL of methanol to remove residual water from the condenser and the mixture is held at reflux at 60° C. to 65° C. for about 2 hours. Solvent is then distilled to a pot temperature of 60° C. to 66° C. at 195 to 200 mm Hg to remove methanol and methylformate. To the mixture is added 355.4 mL benzotrifluoride and the mixture is cooled to 15° C. To the reactor is charged 32.1 g sodium acetate slurried in 77.2 mL water. The reaction is held for 72 hours. To the reactor is then charged 340.4 g of peracetic acid over a 2 hour period starting at 15° C. Addition was adjusted to keep the temperature at or below 20° C. The mixture was then heated to 25° C. for 4 hours. The aqueous (top) layer was separated at 25° C. and the organic layer was washed with 190 mL of 10% sodium sulfite. The organic layer contains compound 70 and can be stored indefinitely.

Step 3. Preparation of Compound 30.

To the organic layer of Step 2 is added 383.8 g of concentrated sulfuric acid. The mixture is heated at 75° C. for 2 hours and the aqueous (bottom) layer is separated at 40 to 50° C. To the reactor is charged 609 mL of 10% sodium bicarbonate and the mixture is stirred for 15 minutes. The aqueous (top) layer is separated. Solvent is distilled from the organic layer at 63 to 66° C. at 195 to 200 mm Hg. To the reactor is charged 1160 mL of isopropyl alcohol over 10 minutes at 50° C. The reactor is cooled to 38° C. and held for 1 hour. Some crystallization occurs. The reactor is cooled to 15° C. over 30 minutes and held for 120 minutes, causing further crystallization of 30. The crystals are filtered and dried to yield 200.0 g of a crystalline yellow solid. The crystals of 30 are washed with 290 mL of 10° C. isopropyl alcohol.

EXAMPLE 6

Preparation of 1-(2,2-dibutyl-S,S-dioxido-3-oxopropylthio)-2-((4-methoxyphenyl)methyl)-4-dimethylaminobenzene, 29

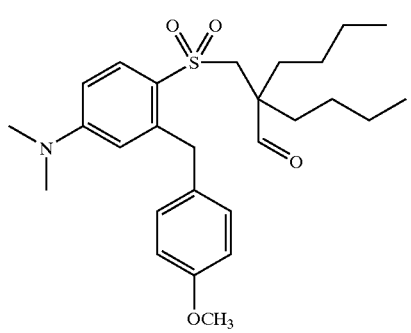

A 300 ml autoclave was fitted with a Stirmix hollow shaft gas mixing agitator, an automatic cooling and heating temperature control, and an in-reactor sampling line with sintered metal filter. At 20° C. the autoclave was charged with 15.0 grams of 30, 2.5 grams of Pd/C catalyst, 60 grams of ethanol, 10.0 grams of formaldehyde (36% aqueous solution), and 0.55 grams of concentrated sulfuric acid. The reactor was closed and pressurized the reactor to 60 psig (515 kPa) with nitrogen to check for leakage. The pressure was then reduced to 1–2 psig (108–115 kPa). The purge was repeated three times. The autoclave was then pressurized with $H_2$ to 60 psig (515 kPa) while the reactor temperature was held at 22° C. The agitator was started and set to 800–1000 rpm and the reactor temperature control is set at 30–40° C. When the cooling capacity was not enough to control the temperature, the agitator rpm or the reactor pressure was reduced to maintain the set temperature. After about 45 minutes when the heat release was slowing down (about 70% of hydrogen usage was reacted), the temperature was raised to 60° C. Hydrogen was then released and the autoclave was purged with nitrogen three times. The content of the reactor was pressure filtered through a sintered metal filter at 60° C. The filtrate was stirred to cool to the room temperature over 1–2 hours and 50 grams of water was added over 1 hour. The mixture was stirred slowly at 4° C. overnight and filtered through a Buche type filter. The cake was air dried to give 13.0 grams of 29 with 99+% assay. The isolated yield was 89%.

EXAMPLE 7

Preparation of syn-3,3-dibutyl-7-(dimethylamino)-1,1-dioxido-4-hydroxy-5-(4-methoxyphenyl)-2,3,4,5-tetrahydrobenzothiepine, syn-24

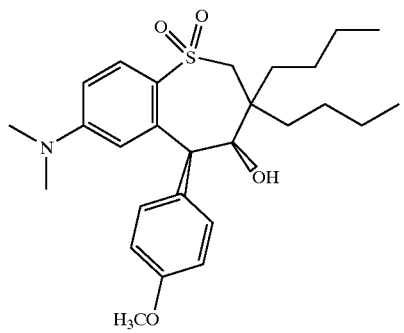

syn-24

A 250 ml round bottom glass reactor fitted with mechanical agitator and a heating/cooling bath was purged with nitrogen. Forty-five grams of potassium t-butoxide/THF solution were charged to the reactor and agitation was started. In a separate container 18 grams of 29 was dissolved in 25 grams of THF. The 29/THF solution was charged into the reactor through a addition funnel over about 2.0 hours. The reactor temperature was controlled between about 16–20° C. Salt precipitated after about half of 29 was added. The slurry was stirred at 16–20° C. for an hour. The reaction was quenched with 54 grams of 7.4% ammonium chloride aqueous solution over a period of about 30 minutes while keeping the reactor temperature at 16–24° C. The mixture was gently stirred until all salt is dissolved (about 10 minutes). Agitation was stopped and the phases were allowed to separate. The aqueous layer was drained. The organic layer was charged with 50 ml water and 25 grams of isopropyl alcohol. The agitator was started and crystallization was allowed to take place. The THF was distilled under the ambient pressure, with b.p. from 60 to 65° C. and pot temperature from 70 to 77° C. The crystals dissolved as the pot gets heated and reappeared when the THF started to distill. After distillation was complete, the slurry was slowly cooled to 4° C. over 2–3 hours and stirred slowly for several hours. The slurry was filtered with a 150 ml Buche filter and the cake was washed with 10 grams of cold 2:1 water/isopropyl alcohol solution. Filtration was complete in about 5 minutes. The cake was air dried to give 16.7 grams of syn-24 with 99+% assay and a 50/50 mixture of R,R and S,S isomers.

Example 8a

Conditions for Optical Resolution of Compound (4R,5R)-24

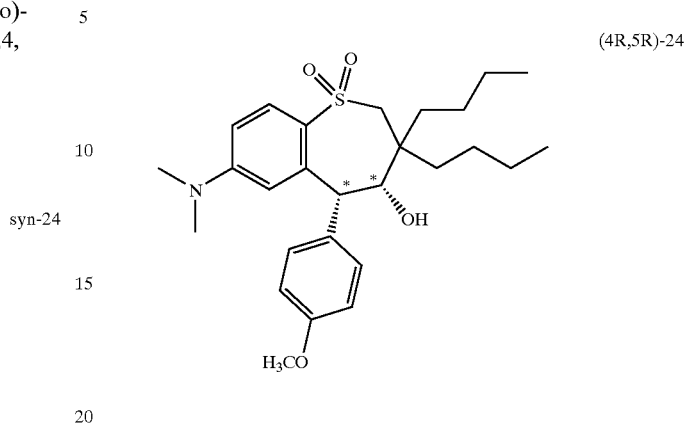

(4R,5R)-24

The following simulated moving bed chromatography (SMB) conditions are used to separate the (4R,5R) and (4S,5S) enantiomers of compound syn-24.

| | |
|---|---|
| Column (CSP): | Daicel Chiralpak AS |
| Mobile Phase: | acetonitrile (100%) |
| Column Length: | 11 cm (9 cm for column 6) |
| Column I.D.: | 20.2 cm |
| Number of Columns: | 6 columns |
| Feed Concentration: | 39 grams/liter |
| Eluent Flowrate: | 182 L/hour |
| Feed Flowrate: | 55 L/hour |
| Extract Flowrate: | 129.4 L/hour |
| Raffinate Flowrate: | 107.8 L/hour |
| Recycling Flowrate: | 480.3 L/hour |
| Period: | 0.6 minute |
| Temperature: | ambient |

SMB Performance:

| | |
|---|---|
| Less retained enantiomer purity (%) | 92.8% |
| Less retained enantiomer concentration | 10 g/L |
| More retained enantiomer recovery yield (%) | 99.3% |
| More retained enantiomer concentration | 7 g/L |

Example 8b

Alternate Conditions for Optical Resolution of Compound (4R,5R)-24

The following simulated moving bed chromatography (SMB) conditions are used to separate the (4R,5R) and (4S,5S) enantiomers of compound syn-24.

| | |
|---|---|
| Column (CSP): | di-methyl phenyl derivative of tartaric acid (Kromasil DMB) |
| Mobile Phase: | toluene/methyl tert-butyl ether (70/30) |
| Column Length: | 6.5 cm |
| Column I.D.: | 2.12 cm |
| Number of Columns: | 8 columns |
| Zones: | 2-3-2-1 |
| Feed Concentration: | 6.4 weight percent |
| Eluent Flowrate: | 20.3 g/minute |
| Feed Flowrate: | 0.7 g/minute |

|  |  |
|---|---|
| Extract Flowrate: | 5.0 g/minute |
| Raffinate Flowrate: | 16.0 g/minute |
| Period: | 8 minute |
| Temperature: | ambient |

SMB Performance:

|  |  |
|---|---|
| Less retained enantiomer purity (%) | >98% |
| Less retained enantiomer recovery yield (%) | >95% |

Example 8c

Alternate Conditions for Optical Resolution of Compound (4R,5R)-24

The following simulated moving bed chromatography (SMB) conditions are used to separate the (4R,5R) and (4S,5S) enantiomers of compound syn-24.

|  |  |
|---|---|
| Column (CSP): | di-methyl phenyl derivative of tartaric acid (Kromasil DMB) |
| Mobile Phase: | toluene (100%) |
| Column Length: | 6.5 cm |
| Column I.D.: | 2.12 cm |
| Number of Columns: | 8 columns |
| Zones: | 2-3-2-1 |
| Feed Concentration: | 64 weight percent |
| Eluent Flowrate: | 20.3 g/minute |
| Feed Flowrate: | 0.5 g/minute |
| Extract Flowrate: | 4.9 g/minute |
| Raffinate Flowrate: | 15.9 g/minute |
| Period: | 8 minute |
| Temperature: | ambient |

SMB Performance:

|  |  |
|---|---|
| Less retained enantiomer purity (%) | >98% |
| Less retained enantiomer recovery yield (%) | >95% |

Example 8d

Racemization of Compound (4S,5S)-24

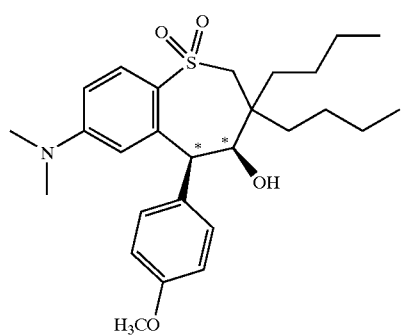

(4S,5S)-24

A 250 mL round bottom glass reactor with mechanical agitator and a heating/cooling bath is purged with nitrogen gas. In a flask, 18 g of (4S,5S)-24 (obtained as the more retained enantiomer in Examples 8a–8c) is dissolved in 50 g of dry THF. This solution is charged into the reactor and brought to about 23–25° C. with agitation. To the reactor is charged 45 g of potassium t-butoxide/THF solution (1 M, Aldrich) through an addition funnel over about 0.5 hour. A slurry forms. Stir the slurry at about 24–26° C. for about 1–1.5 hours. The reaction is quenched with 54 g of 7.5% aqueous ammonium chloride while keeping the reactor temperature at about 23–26° C. The first ca. 20% of the ammonium chloride solution is charged slowly until the slurry turns thin and the rest of the ammonium chloride solution is charged over about 0.5 hour. The mixture is stirred gently until all the salt is dissolved. The agitation is stopped and the phases are allowed to separate. The aqueous layer is removed. To the organic layer is charged 50 mL of water and 25 g of isopropyl alcohol. The agitator is started and crystallization is allowed to take place. THF is removed by distillation at ambient pressure. The crystals dissolve as the pot warms and then reappear when the THF starts to distill. The resulting slurry is cooled slowly to 4° C. within 2–3 hours and slowly stirred for 1–2 hours. The slurry is filtered with a 150 mL Buche filter and washed with 20 g of 0–4° C. isopropyl alcohol. The cake is air dried at about 50–60° C. under vacuum to give 16.7 g of racemic 24.

EXAMPLE 9

Preparation of (4R,5R)-3,3-dibutyl-7-(dimethylamino)-1,1-dioxido-4-hydroxy-5-(4-hydroxyphenyl)-2,3,4,5-tetrahydrobenzothiepine, (4R,5R)-28

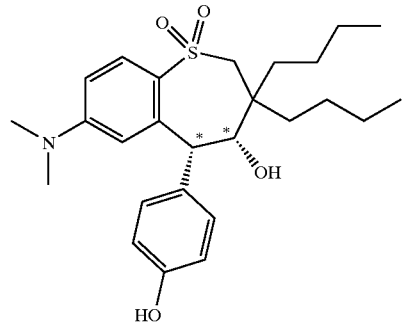

(4R,5R)-28

A 1000 mL 4 neck Reliance jacketed reactor flask was fitted with a mechanical stirrer, a nitrogen inlet, an addition funnel, condenser or distillation head with receiver, a thermocouple, and a Teflon paddle agitator. The flask was purged with nitrogen gas and was charged with 41.3 grams of (4R,5R)-24 and 18.7 grams of methionine followed by 240 grams of methanesulfonic acid. The mixture was heated to 75° C. and stirred for 8 hrs. The mixture was then cooled to 25° C. and charged with 480 mL of 3-pentanone. The solution was homogeneous. Next, the flask was charged with 320 mL of dilution water and was stirred for 15 minutes. The aqueous layer was separated and to the organic layer was added 250 mL of saturated sodium bicarbonate. The mixture was stirred for 15 minutes and the aqueous layer was separated. Solvent was distilled to approximately one-half volume under vacuum at 50° C. The flask was charged with 480 mL of toluene, forming a clear solution. Approximately half the volume of solvent was removed at 100 mmHg. The mixture was cooled to 10° C. and stirred overnight. Crystals were filtered and washed with 150 mL cold toluene and allowed to dry under vacuum. Yielded 29.9 g with a 96.4 wt % assay. The filtrate was concentrated and toluene was added to give a second crop of 2.5 grams of crystals. A total of 32.1 g of dry off white crystalline (4R,5R)-28 was obtained.

Example 9a

Alternate Preparation of (4R,5R)-3,3-dibutyl-7-(dimethylamino)-1,1-dioxido-4-hydroxy-5-(4-hydroxyphenyl)-2,3,4,5-tetrahydrobenzothiepine, (4R,5R)-28

A 1000 mL 4 neck Ace jacketed reactor flask is fitted with a mechanical stirrer, a nitrogen inlet, an addition funnel, condenser or distillation head with receiver, a thermocouple, and a Teflon paddle agitator. The flask is purged with nitrogen gas and is charged with 40.0 grams of (4R,5R)-24 and 17.8 grams of methionine followed by 178.6 grams of methanesulfonic acid. The mixture is heated to 80° C. and stirred for 12 hrs. The mixture is then cooled to 15° C. and charged with 241.1 mL of water over 30 minutes. The reactor is then charged with 361.7 mL of 3-pentanone. Next, the flask is stirred for 15 minutes. The aqueous layer is separated and to the organic layer is added 361.7 mL of saturated sodium bicarbonate. The mixture is stirred for 15 minutes and the aqueous layer was separated. Solvent is distilled to approximately one-half volume under vacuum at 50° C. Crystals start to form at this time. The flask is charged with 361.7 mL of toluene and the mixture is cooled to 0° C. Crystals are allowed to form. Crystals are filtered and washed with 150 mL cold toluene and allowed to dry under vacuum at 50° C. Yield 34.1 g of off-white crystalline (4R,5R)-28.

Example 9b

Alternate Preparation of (4R,5R)-3,3-dibutyl-7-(dimethylamino)-1,1-dioxido-4-hydroxy-5-(4-hydroxyphenyl)-2,3,4,5-tetrahydrobenzothiepine, (4R,5R)-28

A first 45 L reactor is purged with nitrogen gas. To it is charged 2.5 kg of (4R,5R)-24 followed by 1.1 kg of methionine and 11.1 kg of methanesulfonic acid. The reaction mixture is heated to 85° C. with agitation for 7 hours. The reaction mixture is then cooled to 5° C. and 17.5 L of water is slowly charged to the first reactor. The reaction temperature will reach about 57° C. Next, 17.5 L of methyl isobutyl ketone (MIBK) are charged to the first reactor and the reaction mixture is stirred for 30 minutes. The mixture is allowed to stand for 30 minutes and the layers are separated. The aqueous phase is transferred to a second 45 L reactor and 10 L of MIBK is charged to the second reactor. The second reactor and its contents are stirred for 30 minutes and then allowed to stand for 30 minutes while the layers separate. The organic phase is separated from the second reactor and the two organic phases are combined in the first reactor. To the first reactor is carefully charged 1.4 kg of aqueous sodium bicarbonate. The mixture is stirred for 30 minutes and then allowed to stand for 30 minutes. The phases are separated. If the pH of the aqueous phase is less than 6 then a second bicarbonate wash is performed. After the bicarbonate wash, 15 L of water is charged to the first reactor and the mixture is heated to 40° C. The mixture is stirred for 30 minutes and then allowed to stand for 30 minutes. The phases are separated. The organic phase is concentrated by vacuum distillation so that approximately 5 L of MIBK remain in the concentrate. The distillation starts when the batch temperature is at 35° C. at 1 psia. The distillation is complete when the batch temperature reaches about 47.8° C. The batch temperature is then adjusted to 45° C. and 20 L of heptane is charged to the product mixture over 20 minutes. The resulting slurry is cooled to 20° C. The product slurry is filtered (10 micron cloth filter) and washed with 8 L of 20% MIBK/heptane solution. The product is dried on the filter at 80° C. for 21 hours under vacuum. A total of 2.16 kg of white crystalline (4R,5R)-28 is isolated.

Example 9c

Batch Isolation of Compound (4R,5R)-28 (or Compound (4S,5S)-28) from Acetonitrile Solution A 1 L reactor is equipped with baffles and a 4-blade radial flow turbine. The reactor is purged with IL of nigrogen gas and charged with 300 mL of water. The water is stirred at a minimum rate of 300 rpm at 5° C. The reactor is charged with 125–185 mL of (4R,5R)-28 in acetonitrile solution (20% w/w) at a rate of 1.4 mL/min. Upon addition, crystals start to form. After addition of the acetonitrile solution, crystals are filtered through a Buchner funnel. The cake is washed with 3 volumes of water and/or followed by 1–2 volumes of ice cold isopropyl alcohol before drying. Alternatively, this procedure can be used on an acetonitrile solution of (4S,5S)-28 to isolate (4S,5S)-28.

Example 9d

Continuous Isolation of Compound (4R,5R)-28 (or Compound (4S,5S)-28) from Acetonitrile Solution A 1 L reactor is equipped with baffles and a 4-blade radial flow turbine. The reactor is purged with 1L of nigrogen gas and charged with 60 grams of water and 30 grams of acetonitrile. The mixture is stirred at 300 rpm and 5° C. Into the reactor are fed 300 mL of water and 125 mL of 20% (w/w) (4R,5R)-28 in acetonitrile solution at rates of 1.7 mL/min and 1 mL/min, respectively. When the contents of the reactor reach 70–80% of the volume of the reactor, the slurry can be drained to a filter down to aminimum stirring level in the reactor and followed by more feeding. Alternatively, the reactor can be drained continuously as the feeds continue. The water/acetonitrile ratio can be in the range of about 2:1 to about 3:1. Filtered cake can be handled as described in Example 9c. Alternatively, this procedure can be used on an acetonitrile solution of (4S,5S)-28 to isolate (4S,5S)-28.

EXAMPLE 10

Preparation of 1-(chloromethyl)-4-(hydroxymethyl) benzene, 55

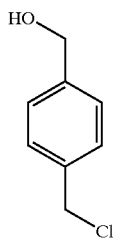

55

A reaction flask fitted with a nitrogen inlet and outlet, a reflux condenser, and a magnetic stirrer was purged with nitrogen. The flask was charged with 25 g of 4-(chloromethyl)benzoic acid. The flask was charged with 75 mL of THF at ambient temperature. Stirring caused a suspension to form. An endothermic reaction ensued in which the temperature of the reaction mixture dropped 22° C. to 14° C. To the reaction mixture 175 mL of borane-THF adduct was added via a dropping funnel over about 30 minutes. During this exothermic addition, an ice-bath was used for external cooling to keep the temperature below 30° C. The reaction mixture was stirred at 20° C. for 1 h and it was then cooled to 0° C. The reaction mixture was quenched by slow addition of 1M sulfuric acid. The resulting reaction mixture was diluted with 150 mL of t-butyl methyl ether (TBME) and stirred for at least 20 min to destroy boric acid esters. The layers were separated and the aqueous layer was washed with another portion of 50 mL of TBME. The combined organic layers were washed twice with 100 mL of saturated sodium bicarbonate solution. The organic layer was dried over 11 g of anhydrous sodium sulfate and filtered. The solvents were evaporated on a rotary evaporator at 45° C. (bath temperature) and <350 mbar yielding a colorless oil. The oil was seeded with crystals and the resulting solid 55 was dried under vacuum. Yield: 19.7 g (86%). Assay by GC (HP-5 25 meter column, 1 mL N$_2$/min at 100° C., FID detection at 300° C., split 50:1).

EXAMPLE 11

Preparation of (4R,5R)-1-((4-(4-(3,3-dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane chloride, 41

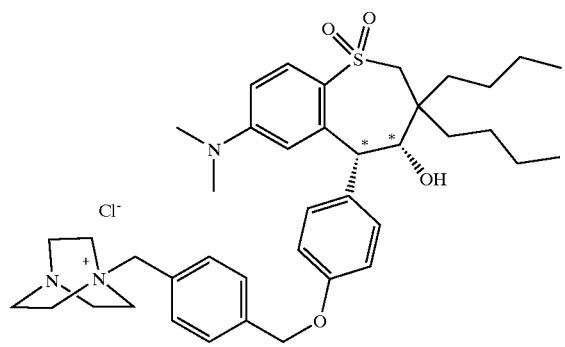

Step 1. Preparation of (4R,5R)-26.

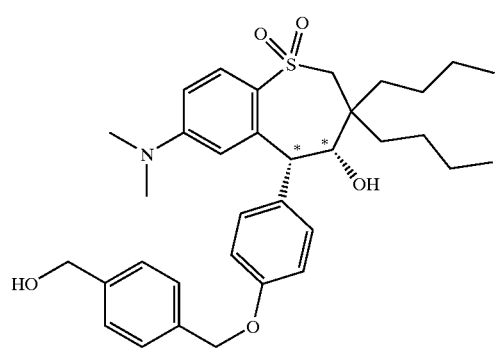

A 1000 mL 4 neck jacketed Ace reactor flask was fitted with a mechanical stirrer, a nitrogen inlet, an addition funnel or condenser or distilling head with receiver, a thermocouple, four internal baffles and a 28 mm Teflon turbine agitator. The flask was purged with nitrogen gas and charged with 25.0 grams of (4R,5R)-28 and 125 mL of N,N-dimethylacetamide (DMAC). To this was added 4.2 grams of 50% sodium hydroxide. The mixture was heated to 50° C. and stirred for 15 minutes. To the flask was added 8.3 grams of 55 dissolved in 10 mL of DMAC, all at once. The temperature was held at 50° C. for 24 hrs. To the flask was added 250 mL of toluene followed by 125 mL of dilution water. The mixture was stirred for 15 minutes and the layers were then allowed to separate at 50° C. The flask was then charged with 125 mL of saturated sodium chloride solution and stirred 15 minutes. Layers separated cleanly in 30 seconds at 50° C. Approximately half of the solvent was distilled off under vacuum at 50° C. The residual reaction mixture contained (4R,5R)-26.

Step 2. Preparation of (4R,5R)-27.

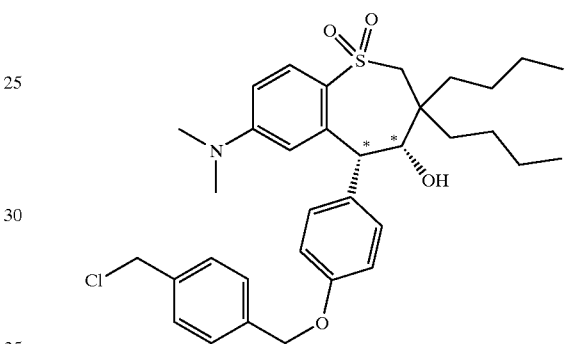

Toluene was charged back to the reaction mixture of Step 1 and the mixture was cooled to 35° C. To the mixture was then added 7.0 grams of thionyl chloride over 5 minutes. The reaction was exothermic and reached 39° C. The reaction turned cloudy on first addition of thionyl chloride, partially cleared then finally remained cloudy. The mixture was stirred for 0.5 hr and was then washed with 0.25N NaOH. The mixture appeared to form a small amount of solids that diminished on stirring, and the layers cleanly separated. The solvent was distilled to a minimum stir volume under vacuum at 50° C. The residual reaction mixture contained (4R,5R)-27.

Step 3. Preparation of 41.

To the reaction mixture of Step 2 was charged with 350 mL of methyl ethyl ketone (MEK) followed by 10.5 mL water and 6.4 grams of diazabicyclo[2.2.2]octane (DABCO) dissolved in 10 mL of MEK. The mixture was heated to reflux, and HPLC showed <0.5% of (4R,5R)-27. The reaction remained homogenous initially then crystallized at the completion of the reaction. An additional 5.3 mL of water was charged to the flask to redissolve product. Approximately 160 mL of solvent was then distilled off at atmospheric pressure. The mixture started to form crystals after 70 mL of solvent was distilled. Water separated out of distillate indicating a ternary azeotrope between toluene, water and methyl ethyl ketone (MEK). The mixture was then cooled to 25° C. The solids were filtered and washed with 150 mL MEK, and let dry under vacuum at 60° C. Isolated 29.8.0 g of off-white crystalline 41.

Example 11a

Alternate Preparation of (4R,5R)-1-((4-(4-(3,3-dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane chloride, Form II of 41

A 1000 mL 4 neck jacketed Ace reactor flask is fitted with a mechanical stirrer, a nitrogen inlet, an addition funnel or condenser or distilling head with receiver, a thermocouple, four internal baffles and a 28 mm Teflon turbine agitator. The flask is purged with nitrogen gas and charged with 25.0 grams of (4R,5R)-28 and 100 mL of N,N-dimethylacetamide (MAC). The mixture is heated to 50° C. and to it is added 4.02 grams of 50% sodium hydroxide. The mixture is stirred for 30 minutes. To the flask is added 8.7 grams of 55 dissolved in 12.5 mL of DMAC, all at once. The charge vessel is washed with 12.5 mL DMAC and the wash is added to the reactor. The reactor is stirred for 3 hours. To the reactor is added 0.19 mL of 49.4% aq. NaOH and the mixture is stirred for 2 hours. To the mixture is added 0.9 g DABCO dissolved in 12.5 mL DMAC. The mixture is stirred 30 to 60 minutes at 50° C. To the flask is added 225 mL of toluene followed by 125 mL of dilution water. The mixture is stirred for 15 minutes and the layers are then allowed to separate at 50° C. The bottom aqueous layer is removed but any rag layer is retained. The flask is then charged with 175 mL of 5% hydrochloric acid solution and stirred 15 minutes. Layers are separated at 50° C. to remove the bottom aqueous layer, discarding any rag layer with the aqueous layer. Approximately half of the solvent is distilled off under vacuum at a maximum pot temperature of 80° C. The residual reaction mixture contains (4R,5R)-26.

Step 2. Preparation of (4R,5R)-27.

Toluene (225 mL) is charged back to the reaction mixture of Step 1 and the mixture is cooled to 30° C. To the mixture is then added 6.7 grams of thionyl chloride over 30 to 45 minutes. The temperature is maintained below 35° C. The reaction turns cloudy on first addition of thionyl chloride, then at about 30 minutes the layers go back together and form a clear mixture. The mixture is stirred for 0.5 hr and is then charged with 156.6 mL of 4% NaOH wash over a 30 minute period. The addition of the wash is stopped when the pH of the mixture reaches 8.0 to 10.0. The bottom aqueous layer is removed at 30° C. and any rag layer is retained with the organic layer. To the mixture is charged 175 mL of saturated NaCl wash with agitation. The layers are separated at 30° C. and the bottom aqueous layer is removed, discarding any rag layer with the aqueous layer. The solvent is distilled to a minimum stir volume under vacuum at 80° C. The residual reaction mixture contains (4R,5R)-27.

Step 3. Preparation of 41.

To the reaction mixture of Step 2 is charged 325 mL of methyl ethyl ketone (MEK) and 13 mL water. Next, the reactor is charged 6.2 grams of diazabicyclo[2.2.2]octane (DABCO) dissolved in 25 mL of MEK. The mixture is heated to reflux and held for 30 minutes. Approximately 10% of solvent volume is then distilled off. The mixture starts to form crystals during distillation. The mixture is then cooled to 20° C. for 1 hour. The off-white crystalline 41 (Form II) is filtered and washed with 50 mL MEK, and let dry under vacuum at 100° C.

Example 11b

Alternate Preparation of (4R,5R)-1-((4-(4-(3,3-dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane Chloride, Form II of 41

A 1000 mL 4 neck jacketed Ace reactor flask is fitted with a mechanical stirrer, a nitrogen inlet, an addition funnel or condenser or distilling head with receiver, a thermocouple, four internal baffles and a Teflon turbine agitator. The flask is purged with nitrogen gas and charged with 25.0 grams of (4R,5R)-28 and 125 mL of N,N-dimethylacetamide (DMAC). The mixture is heated to 50° C. and to it is added 7.11 grams of 30% sodium hydroxide over a period of 15 to 30 minutes with agitation. The mixture is stirred for 30 minutes. To the flask is added 9.5 grams of solid 55. The reactor is stirred for 3 hours. To the mixture is added 1.2 g of solid DABCO. The mixture is stirred 30 to 60 minutes at 50° C. To the flask is added 225 mL of toluene followed by 125 mL of water. The mixture is stirred for 15 minutes and the layers are then allowed to separate at 50° C. The bottom aqueous layer is removed but any rag layer is retained with the organic layer. The flask is then charged with 175 mL of 5% hydrochloric acid solution and stirred 15 minutes. Layers are separated at 50° C. to remove the bottom aqueous layer, discarding any rag layer with the aqueous layer. The flask is then charged with 225 mL of water and stirred 15 minutes. The layers are allowed to separate at 50° C. The bottom aqueous layer is removed, discarding any rag layer with the aqueous layer. Approximately half of the solvent is distilled off under vacuum at a maximum pot temperature of 80° C. The residual reaction mixture contains (4R,5R)-26.

Step 2. Preparation of (4R,5R)-27.

Toluene (112.5 mL) is charged back to the reaction mixture of Step 1 and the mixture is cooled to 25° C. To the mixture is then added 7.3 grams of thionyl chloride over 15 to 45 minutes. The temperature of the mixture is maintained above 20° C. and below 40° C. The reaction turns cloudy on first addition of thionyl chloride, then at about 30 minutes the layers go back together and form a clear mixture. The mixture is then charged with 179.5 mL of 4% NaOH wash over a 30 minute period. The mixture is maintained above 20° C. and below 40° C. during this time. The addition of the wash is stopped when the pH of the mixture reaches 8.0 to 10.0. The mixture is then allowed to separate at 40° C. for at least one hour. The bottom aqueous layer is removed and any rag layer is retained with the organic layer. To the mixture is charged 200 mL of dilution water. The mixture is stirred for 15 minutes and then allowed to separate at 40° C. for at least one hour. The bottom aqueous layer is removed, discarding any rag layer with the aqueous layer. The solvent is distilled to a minimum stir volume under vacuum at 80° C. The residual reaction mixture contains (4R,5R)-27.

Step 3. Preparation of 41.

To the reaction mixture of Step 2 is charged 350 mL of methyl ethyl ketone (MEK) and 7 mL water. The mixture is stirred for 15 minutes and the temperature of the mixture is adjusted to 25° C. Next, the reactor is charged with 6.7 grams of solid diazabicyclo[2.2.2]octane (DABCO). The mixture is maintained at 25° C. for three to four hours. It is then heated to 65° C. and maintained at that temperature for 30 minutes. The mixture is then cooled to 25° C. for 1 hour. The off-white crystalline 41 (Form II) is filtered and washed with 50 mL MEK, and let dry under vacuum at 100° C.

EXAMPLE 12

Alternate preparation of (4R,5R)-1-((4-(4-(3,3-dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane chloride, Form I of 41

(4R,5R)-27 (2.82 kg dry basis, 4.7 mol) was dissolved in MTBE (9.4 L).

The solution of (4R,5R)-27 was passed through a 0.2 mm filter cartridge into the feeding vessel. The flask and was rinsed with MTBE (2×2.5 L). The obtained solution as passed through the cartridge filter and added to the solution of (4R,5R)-27 in the feeding vessel. DABCO (diazabicyclo [2.2.2]octane, 0.784 kg, 7.0 mol) was dissolved in MeOH (14.2 L). The DABCO solution was passed through the filter cartridge into the 100 L nitrogen-flushed reactor. The Pyrex bottle and the cartridge filter were rinsed with MeOH (7.5 L) and the solution was added to the reactor. The (4R,5R)-27 solution was added from the feeding vessel into the reactor at 37° C. over a period of 10 min, while stirring. Methanol (6.5 L) was added to the Pyrex bottle and via the cartridge filter added to the feeding vessel to rinse the remaining (4R,5R)-27 into the reactor. The reaction mixture was brought to 50–60° C. over 10–20 min and stirred at that temperature for about 1 h. The mixture was cooled to 20–25° C. over a period of 1 h. To the reaction mixture, methyl t-butyl ether (MTBE) (42 L) was added over a period of 1 h and stirred for a minimum of 1 h at 20–25° C. The suspension was filtered through a Buchner funnel. The reactor and the filter cake were washed with MTBE (2×14 L). The solids were dried on a rotary evaporator in a 20 L flask at 400–12 mbar, 40° C., for 22 h. A white crystalline solid was obtained. The yield of 41 (Form I) was 3.08 kg (2.97 kg dry, 93.8%) and the purity 99.7 area % (HPLC; Kromasil C 4, 250×4.6 mm column; 0.05% TFA in H$_2$O/ 0.05% TFA in ACN gradient, UV detection at 215 nm).

Example 12a

Conversion of Form I of Compound 41 into Form II of Compound 41

To 10.0 grams of Form I of 41 in a 400 mL jacketed reactor is added 140 mL of MEK. The reactor is stirred (358 rpm) for 10 minutes at 23° C. for 10 minutes and the stirring rate is then changed to 178 rpm. The suspension is heated to reflux over 1 hour using a programmed temperature ramp (0.95° C./minute) using batch temperature control (cascade mode). The delta T$_{max}$ is set to 5° C. The mixture is held at reflux for 1 hour. The mixture is cooled to 25° C. After 3 hours at 25° C., a sample of the mixture is collected by filtration. Filtration is rapid (seconds) and the filtrate is clear and colorless. The white solid is dried in a vacuum oven (80° C., 25 in. Hg) to give a white solid. The remainder of the suspension is stirred at 25° C. for 18 hours. The mixture is filtered and the cake starts to shrink as the mother liquor reaches the top of the cake. The filtration is stopped and the reactor is rinsed with 14 mL of MEK. The reactor stirrer speed is increased from 100 to 300 rpm to rinse the reactor. The rinse is added to the filter and the solid is dried with a rapid air flow for 5 minutes. The solid is dried in a vacuum oven at 25 in. Hg for 84 hours to give Form II of 41.

EXAMPLE 13

Preparation of 2-(phenylthiomethyl)hexanal

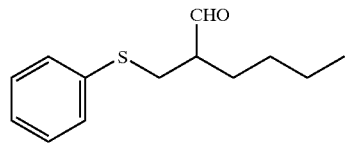

To a stirred mixture of n-butylacrolein (9.5 ml, 71.3 mmol) and Et$_3$N (0.5 mL, 3.6 mmol) at 0° C. under nitrogen is added thiophenol (7.3 mL, 71.3 mmol) in 5 minutes. The mixture is allowed to warm to room temperature in 30 minutes. $^1$H NMR of the reaction mixture sample will show quantitative conversion. Et$_3$N is removed under reduced pressure.

EXAMPLE 14

Preparation of 2-((4-methoxyphenylthio)methyl)hexanal

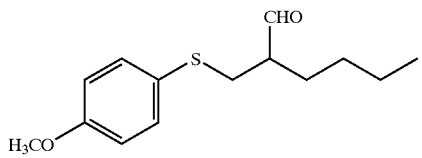

To a stirred mixture of n-butylacrolein (2.66 ml, 20 mmol) and Et$_3$N (0.14 mL, 1 mmol) at 0° C. under nitrogen is added 4-methoxythiophenol (2.46 mL, 20 mmol) in 5 minutes. The mixture is allowed to warm to room temperature in 30 minutes. $^1$HNMR of the reaction mixture sample will show quantitative conversion. Et$_3$N is then removed under reduced pressure.

EXAMPLE 15

Preparation of 2-((4-chlorophenylthio)methyl)hexanal

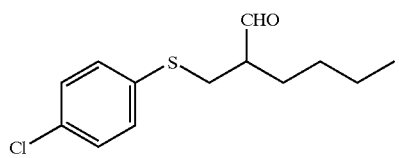

To a stirred mixture of n-butylacrolein (5.32 ml, 40 mmol) and Et$_3$N (0.28 mL, 2 mmol) at 0° C. under nitrogen is added 4-chlorothiophenol (5.78 g, 40 mmol) in 5 minutes. The mixture is allowed to warm to room temperature in 30 minutes. $^1$HNMR of the reaction mixture sample will show quantitative conversion. Et$_3$N is then removed under reduced pressure.

EXAMPLE 16

Preparation of 2-(acetylthiomethyl)hexanal

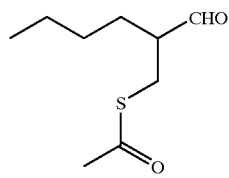

To a stirred mixture of n-butylacrolein (13.3 ml, 100 mmol) and Et$_3$N (0.7 mL, 5 mmol) at 0° C. under nitrogen is added thioacetic acid (7.2 mL, 100 mmol) in 5 minutes. The mixture is allowed to warm to room temperature in 30 minutes. $^1$HNMR of the reaction mixture sample will show quantitative conversion. Et$_3$N is then removed under reduced pressure.

EXAMPLE 17

Preparation of 2-methyl-3-phenylthiopropanal

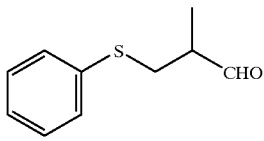

To a stirred mixture of 51.4 g (0.733 mole) of methacrolein and 2 g (0.018 mole) of triethylamine at 0–5° C. is added 80.8 g (0.733 mole) of benzenethiol slowly. The addition rate is such that the temperature was under 10° C. The reaction mixture is stirred at 0–5° C. for one hour. The mixture is placed on a rotary evaporator to remove triethylamine.

EXAMPLE 18

Preparation of 2-(((4-chlorophenyl)sulfonyl)methyl) hexanal

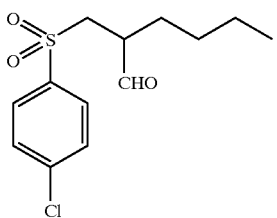

To a stirred solution of 4chlorobenzosulfinate sodium salt (4.10 g, 20.81 mmol) in 20 mL of acetic acid at 60° C. is added 2-butylacrolein (3.8 mL, 28.56 mmol) slowly. The reaction mixture us kept at 50° C. for 3.5 hours. The mixture us diluted with 10 mL of water and extracted with ethyl acetate (2×10 mL). The combined extract is washed with saturated NaHCO$_3$, water, brine, and dried with MgSO$_4$. After removing solvents, the product is obtained as a yellowish slightly viscous oil in 94% yield.

EXAMPLE 19

Preparation of 2-(((4-methylphenyl)sulfonyl)methyl) hexanal

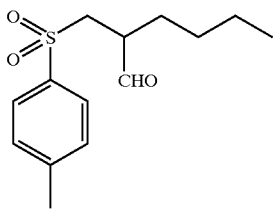

To a stirred solution of 4-toluenesulfinate sodium salt (10.10 g, 56.68 mmol) in 35 mL of acetic acid at 50° C. is added 2-butylacrolein (10.6 mL, 79.66 mmol) slowly. The reaction mixture is kept at 50° C. for 3 hours. After cooling to room temperature, the mixture is diluted with 50 mL of water and extracted with ethyl acetate (2×25 mL). The combined extract is washed with saturated NaHCO$_3$, water, brine, and dried with MgSO$_4$. After removing solvents, the product is obtained as a yellow liquid in 75% yield.

EXAMPLE 20

Preparation of (4E)-2-(acetylthiomethyl)-2-butylhex-4-enal

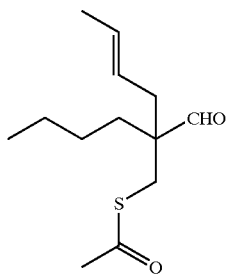

To a stirred solution of 2-(acetylthiomethyl)hexanal (32.6 g, 0.173 mole) in 325 ml of xylenes in a 500-mL RBF fitted with a Dean-Stark trap is added 2-hydroxy-3-butene (22.5 mL, 0.259 mole), followed by pyridinium p-toluenesulfonate (4.34 g, 0.017 mole) at room temperature under nitrogen. The mixture is heated to reflux overnight. After cooling to room temperature, the xylenes solution is washed with 300 mL of saturated NaHCO$_3$ solution. The aqueous phase is extracted with 300 mL of ethyl acetate. The combined organic extract is washed with 200 mL of brine and 200 mL of water. After removing solvents, the product is obtained by vacuum distillation (157–160° C./1.5 mmHg) in 80.5% yield.

EXAMPLE 21

Preparation of (4E)-2-butyl-2-(phenylthiomethyl) hex-4-enal

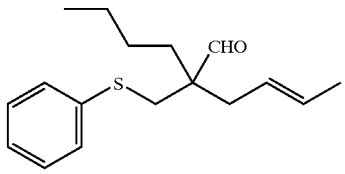

2-(Phenylthiomethyl)hexanal (2.67 g, 12 mmol), 3-buten-2-ol (5 mL, 58 mmol), and p-toluenesulfonic acid (0.05 g, 0.26 mmol) are added to 25 ml of xylenes. The reaction mixture is heated to reflux using a Dean-Stark trap to collect water. After 3 hours, the mixture is cooled to room temperature and diluted with ethyl acetate, which is washed saturated NaHCO$_3$ solution, brine, and dried with MgSO$_4$. After removing solvents, the crude product is purified by chromatography. The product is obtained in 78.6% as a colorless oil.

EXAMPLE 22

Preparation of (4E)-2-methyl-2-(phenylthiomethyl)-hept-4-enal

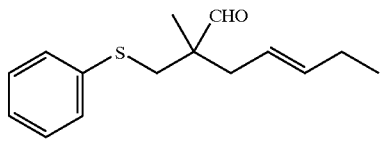

2-Methyl-3-phenylthiopropanal (9.07 g, 0.05 mole), 1-penten-3-ol (21.67 g, 0.25 mole), and p-toluenesulfonic acid (0.24 g, 0.0013 mole) are added to 90 ml of xylenes. The reaction mixture is heated to reflux using a Dean-Stark trap to collect water. After 3 hours, the mixture is cooled to room temperature and quenched with 30 ml of saturated $NaHCO_3$ solution. The two phases are separated and the aqueous phase is extracted with 30 ml of ethyl acetate. The combined organic extracts is washed with 30 ml of brine and dried with $Na_2SO_4$. After removing solvents, the crude product is purified by chromatography. The product is obtained in 77% as a colorless oil.

EXAMPLE 23

Preparation of (4E)-2-methyl-2-(phenylthiomethyl)-hex-4-enal

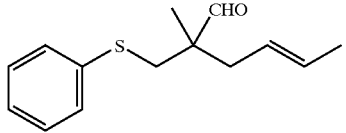

2-Methyl-3-phenylthiopropanal (9.07 g, 0.05 mole), 3-buten-2-ol (18.04 g, 0.25 mole), and p-toluenesulfonic acid (0.24 g, 0.0013 mole) are added to 90 ml of xylenes. The reaction mixture is heated to reflux using a Dean-Stark trap to collect water. After 3 hours, the mixture is cooled to room temperature and quenched with 30 ml of saturated $NaHCO_3$ solution. The two phases are separated and the aqueous phase is extracted with 30 ml of ethyl acetate. The combined organic extracts is washed with 20 ml of brine and dried with $Na_2SO_4$. After removing solvents, the crude product is purified by chromatography. The product is obtained in 74.3% as a colorless oil.

EXAMPLE 24

Preparation of (4E)-2-butyl-2-(((4-chlorophenyl)sulfonyl)methyl)hex-4-enal

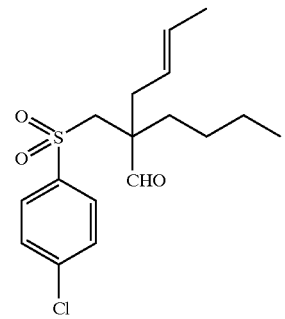

To a stirred solution of 2-(((4-chlorophenyl)-sulfonyl)methyl)hexanal (3.38 g, 11.73 mmol) in 30 ml of toluene in a RBF fitted with a Dean-Stark trap is added 2-hydroxy-3-butene (5 mL, 57.73 mmol), followed by p-toluenesulfonic acid (0.13 g) at room temperature under nitrogen. The mixture is heated to reflux for 20 hours. After cooling to room temperature, the toluene solution is diluted with 10 mL of ethyl acetate and washed with 10 mL of saturated $NaHCO_3$ solution. The aqueous phase is extracted with ethyl acetate. The combined organic extract is washed with water (2×10 mL), brine (1×10 mL), and dried with $MgSO_4$. After removing solvents, the product is obtained as a brownish oil in 98% yield.

EXAMPLE 25

Preparation of (4E)-2-butyl-2-(((4-methylphenyl)sulfonyl)methyl)hex-4-enal

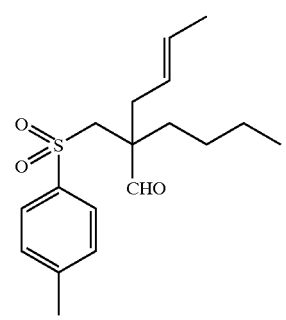

To a stirred solution of 2-(((4-methylphenyl)-sulfonyl)methyl)hexanal (5.63 g, 21 mmol) in 35 ml of toluene in a RBF fitted with a Dean-Stark trap is added 2-hydroxy-3-butene (10 mL, 115 mmol), followed by p-toluenesulfonic acid (0.13 g) at room temperature under nitrogen. The mixture is heated to reflux overnight. After cooling to room temperature, the toluene solution is washed with saturated $NaHCO_3$ solution (2×10 mL), water (2×20 mL), brine (1×20 mL), and dried with $MgSO_4$. After removing solvents, the product is obtained as a brownish oil in quantitative yield with a GC purity of 89%.

EXAMPLE 26

Preparation of 2-butyl-2-(((4-methylphenyl)sulfonyl)methyl)hexanal

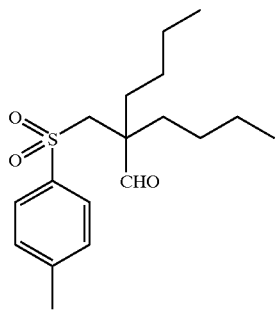

To a solution of 0.5 g of 2-butyl-2-(((4-ethyl-phenyl)sulfonyl)methyl)hexanal in 30 mL of toluene is added 5 mL of 37% formaldehyde and 220 mg of 20% Pd(OH)$_2$/C catalyst. The reaction mixture is purged with dry nitrogen gas (3×) and hydrogen gas (3×) and hydrogenated at 60 psi H2 and 60° C. for 15 hours. The catalyst is removed by filtration and washed with ethanol (2×20 mL). Solvents of the combined washes and filtrate are removed under vacuum to yield the crude product.

For the following examples $^1$H and $^{13}$C NMR spectra were recorded on a Varian 300 spectrometer at 300 and 75 MHz respectively. The $^1$H chemical shifts are reported in ppm downfield from tetramethylsilane. The $^{13}$C chemical shifts are reported in ppm relative to the center line of CDCl$_3$ (77.0 ppm). Melting points were recorded on a Buchi 510 melting point apparatus and are uncorrected. HPLC data was obtained on a Spectra Physics 8800 Chromatograph using a Beckman Ultrasphere C18 250×4.6 mm column. HPLC conditions: detector wavelength=254 nm, sample size=10 μL, flowrate=1.0 mL/min, mobile phase=(A) 0.1% aqueous trifluoroacetic acid: (B) acetonitrile. Quantitative HPLC analysis was determined by running samples of known concentration of the crude product and of purified product, adjusting the peak areas for concentration differences, and dividing the peak area of the crude sample by the peak area of the purified sample. HPLC Gradient:

| Time | % A | % B |
| --- | --- | --- |
| 0 min | 50 | 50 |
| 5 min | 50 | 50 |
| 30 min | 0 | 100 |
| 40 min | 0 | 100 |

EXAMPLE 27

Preparation of Compound 32

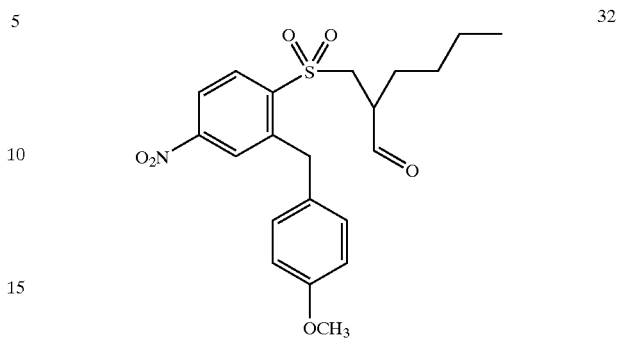

Procedure A: Na$_2$S.9H$_2$O (8.64 g, 36.0 mmol) and sulfur (1.16 g, 36.0 mmol) were combined in a 50 mL round-bottom flask. The mixture was heated to 50° C. until homogeneous, and water (10.0 mL) was added. Compound 33 (10.00 g, 36.0 mmol) and ethanol (100 mL) were combined in a 500 mL round-bottom flask. The reaction flask was purged with N$_2$ and equipped with mechanical stirrer. The reaction mixture was heated to 65° C. until homogeneous, and then increased to 74° C. The disulfide solution was added to the 500 mL reaction flask over 10 minutes. After 1.5 hrs at reflux, analysis of an aliquot by HPLC indicated complete conversion of 33. Aqueous 18% NaOH (20.0 g, 90.0 mmol) was added over 5 minutes (endothermic). After 15 minutes, the reaction mixture was cooled to 0° C., and 30% H$_2$O$_2$ (16.00 g, 140.0 mmol) was added dropwise keeping temp below 20° C. After 1.5 hrs at <20° C., analysis of an aliquot by HPLC indicated total oxidation of the sodium thiophenolate intermediate. The ethanol was removed under reduced pressure at <65° C. Water (100 mL) was added, and the mixture was washed with CH$_2$Cl$_2$ (100 mL). 10% HCl (~40 mL) was added until pH=1, and the reaction mixture was extracted with CH$_2$Cl$_2$ (100.0 mL). 2-Butylacrolein (5.20 mL, 39.2 mmol) was added to the organic extract, and the mixture was stirred for 1 hour. Analysis of an aliquot by HPLC indicated very little sulfinic acid intermediate. The organic layer was concentrated in vacuo to give an amber solid (14.19 g). Analysis by quantitative HPLC indicated 84% purity, which corresponds to 11.92 g Michael adduct (79% yield of 32 based on 3).

Procedure B: Compound 33 (4.994 g, 17.98 mmol) and dimethylacetamide (21.0 mL) were combined in a dry 250 mL round-bottom flask. The reaction flask was purged with N$_2$, equipped with magnetic stirrer, and heated to 40° C. until the mixture became homogeneous. Na$_2$S.3H$_2$O (2.91 g, 22.37 mmol) and water (4.0 mL) were combined in a separate flask and heated to 55° C. until homogeneous. The Na$_2$S solution was then added portion-wise to the reaction flask over 25 minutes. After 2.5 hrs at 40° C., analysis of an aliquot by HPLC indicated complete conversion of 33. After 2 hrs more, the reaction mixture was cooled to 30° C., and aq. 18% NaOH (10.02 g, 44.90 mmol) was added. After 20 min, the reaction mixture was cooled to 0° C., and 30% H$_2$O$_2$ (8.02 g, 70.6 mmol) was added dropwise over 30 minutes while maintaining a temperature of less than 15° C. After 10 min, an aliquot was removed and analyzed by HPLC, which indicated >93% oxidation of the sodium thiophenolate intermediate. After 1 hr, Na$_2$SO$_3$ (6.05 g, 48.0 mmol) and water (50.0 mL) were added, and the cooling bath was removed. After 20 min, the mixture was washed with toluene (or CH$_2$Cl$_2$) (2×50.0 mL). Toluene (or CH$_2$Cl$_2$) (50.0 mL), 2-butylacrolein (2.60 mL, 19.6 mmol), and n-Bu$_4$NI (0.032 g, 0.087 mmol) were added, and the reaction mixture was cooled to 0° C. To this, 10% HCl (~30 mL) was added until pH=1. The cooling bath was removed, and the reaction mixture was stirred for 30 min. Analysis of an aliquot of the aqueous layer by HPLC indicated very little sulfinic acid intermediate. After 30 min more, the aqueous layer was separated and discarded. The organic layer was kept at −10° C. overnight, stirred at R.T. for 5 hrs. Analysis of the toluene solution by quantitative HPLC indicated 6.444 g Michael adduct, (85% yield of 32 based on 33).

For characterization, a portion of the crude product was concentrated in vacuo and precipitated from ethyl ether to afford a yellow solid: mp 62.0–76.0° C.; HPLC (CH$_3$CN/ H$_2$O): rt=22.4 min. $^1$H NMR (CDCl$_3$) ????????t, J=6.0 Hz, 3H), 1.24 (m, 4H), 1.53 (m, 1H), 1.70 (m, 1H), 2.83 (dd, J=14.1, 4.2 Hz, 1H), 2.98 (m, 1H), 3.56 (dd, J=14.4, 7.8 Hz, 1H), 3.79 (s, 3H), 4.53 (s, 2H), 6.87 (dd, J=6.6, 2.4 Hz, 2H), 7.13 (d, J=8.7 Hz, 2H), 8.12 (s, 1H), 8.20 (d, J=1.2 Hz, 2H), 9.53 (d, J=0.9 Hz, 1"). $^{13}$C NMR (CDCl$_3$) ? 13.6, 22.4, 28.1, 28.5, 37.4, 45.4, 53.9, 55.2, 114.4, 121.7, 127.3, 129.6, 130.3, 132.1, 142.7, 144.1, 150.7, 158.7, 199.5. HRMS (ES+) calcd for C$_{21}$H$_{25}$NO$_6$S+NH$_4$: 437.1731, found: 437.1746. Anal. (C$_{21}$H$_{25}$NO$_6$S): C, 60.13; H, 6.01; N, 3.34; O, 22.88; S, 7.64. Found: C, 60.22; H, 5.98; N, 3.32; O, 22.77; S, 7.73.

EXAMPLE 28

Preparation of Compound 18a

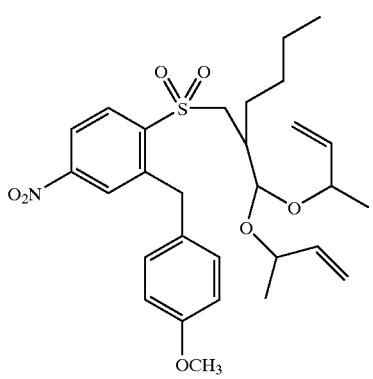

18a

Procedure A: Compound 32 (11.577 g, 27.598 mmol), p-toluenesulfonic acid monohydrate (0.6115 g, 3.21 mmol), CH$_2$Cl$_2$ (70 ml) and 3-buten-2-ol (13.91 mL, 160.5 mmol) were combined in a dry 250 mL round-bottom flask. The reaction flask was purged with N$_2$ and equipped with magnetic stirrer, Dean Stark trap, and reflux condenser. The reaction mixture was heated to reflux. After 10.25 hrs, analysis of an aliquot by HPLC indicated 78.6% 18a, 13.3% pre-Claisen enol ether, 3.7% 32 and approximately 4% byproducts. K$_2$CO$_3$ (1.50 g, 10.8 mmol) was added to the reaction flask. After 2.5 hrs, CH$_2$Cl$_2$ (50.0 mL) was added, and the mixture was filtered through celite. The filtrate was collected and concentrated in vacuo to yield an amber oil (15.73 g). Quantitative HPLC was performed using a sample of purified 18a. The total peak area of the crude product was determined by summing the pre-Claisen enol ether and 18a peaks. It was assumed that they have the same HPLC response factors. Analysis by quantitative HPLC indicated 90% purity, which corresponds to 14.20 g 18a and pre-Claisen enol ether 47, (94% yield of 18a based on 32).

Procedure B: Compound 32 (5.43 g, 12.9 mmol), 3-buten-2-ol (76.16 g, 85.4 mmol), p-toluenesulfonic acid monohydrate (0.258 g, 1.36 mmol) and toluene (51.0 mL) were combined in a 100 mL round-bottom flask. The reaction flask was purged with N$_2$ and equipped with magnetic stirrer, Dean Stark trap, condenser, and vacuum line. The condenser was cooled to −10° C. via a Cryocool bath, and the Dean Stark trap was filled with 3-buten-2-ol (about 11 mL). The reaction flask was evacuated to 107.5 mmHg via a pressure controller and heated to 49° C. After 4 hrs, the reaction flask was cooled to R.T. and concentrated in vacuo at 30° C. The crude product was collected as an amber oil (8.154 g). Quantitative HPLC was performed using a sample of purified 18a. The total peak area of the crude product was determined by summing the pre-Claisen enol ether and 18a peaks. It was assumed that they have the same HPLC response factors. Analysis by quantitative HPLC indicated 69% purity, which corresponds to 5.626 g 18a and pre-Claisen enol ether 47, (80% yield of 18a based on 32)):

HPLC (CH$_3$CN/H$_2$O): 18a: rt=32.56, 32.99, 33.09 min, pre-Claisen enol ether: rt=30.7 min. $^1$H NMR (CDCl$_3$) ? 0.84–0.93 (m, 3H), 1.09–1.34 (m, 1011), 1.40–1.70 (m, 2H), 2.16–2.35 (m, 1H), 2.88–2.98 (m, 1H), 3.52–3.63 (m, 1H), 3.80 (m, 3H), 3.84–4.10 (m, 2H), 4.49 (s, 1H), 4.50 (s, 1H), 4.59 (d, J=3.0 Hz, 0.25H), 4.60 (d, J=2.7 Hz, 0.25H), 4.65 (d, J=2.4 Hz, 0.25H), 4.70 (d, J=2.4 Hz, 0.25H), 5.00–5.18 (m, 4H), 5.42–5.84 (m, 2H), 6.87 (d, J=8.7 Hz, 1H), 6.88 (d, J=8.4 Hz, 1H), 7.12–7.17 (m, 2H), 8.02 (t, J=2.4 Hz, 1H), 8.14–8.17 (m, 1H), 8.23–8.27 (m, 1H); $^{13}$C NMR (CDCl$_3$) ??13.8, 20.1, 20.9, 21.0, 21.4, 21.51, 21.57, 21.6, 22.53, 22.55, 22.57, 28.7, 28.8, 28.94, 28.99, 29.0, 29.3, 29.4, 29.8, 37.1, 37.2, 37.3, 38.73, 38.75, 53.3, 55.2, 55.60, 55.66, 55.7, 55.9, 73.4, 73.5, 73.8, 73.9, 74.3, 75.1, 75.9, 97.7, 98.3, 98.4, 99.5, 113.6, 114.4, 114.5, 114.9, 115.7, 115.9, 116.1, 116.3, 116.7, 116.9, 121.22, 121.26, 121.31, 121.34, 126.70, 126.75, 126.8, 129.73, 129.77, 130.45, 130.48, 130.5, 131.51, 131.51, 131.57, 139.6, 139.8, 139.9, 140.1, 140.2, 140.3, 143.6, 143.70, 143.71, 143.81, 143.84, 144.26, 144.29, 144.34, 144.35, 144.37, 150.5, 158.6; HRMS (ES+) calcd for C$_{29}$H$_{39}$NO$_7$S+NH$_4$: 563.2791, found: 563.2804.

EXAMPLE 29

Preparation of Compound 31

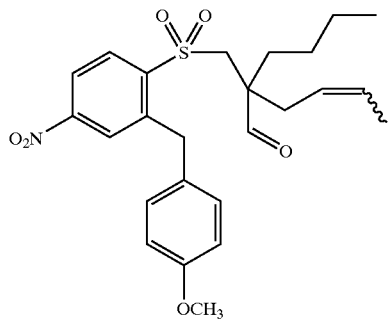

31

Procedure A: A crude mixture of 18a and pre-Claisen enol ether 47 (13.636 g, 24.989 mmol), o-xylene (75.0 mL), and calcium hydride (0.334 g, 7.93 mmol) were combined in a dry 250 mL round-bottom flask. The reaction flask was purged with N$_2$, equipped with magnetic stirrer, and heated to 145° C. After 3 hours, an aliquot was removed and analyzed by HPLC, which indicated 93% 31, 1% 32, 3% pre-Claisen enol ether 47, and 4% byproducts. The reaction mixture was cooled to RT and filtered through celite washing with o-xylene (50.0 mL). The crude product was concentrated in vacuo and collected as an amber oil (11.525 g). Analysis by quantitative HPLC indicated 86% purity, which corresponds to 9.9115 g Claisen product (80% yield based on the mixture of 31 and pre-Claisen enol ether 47).

Procedure B: A crude mixture of 18a and pre-Claisen enol ether 47 (2.700 g, 4.948 mmol), toluene (15.0 mL) and calcium hydride (0.0704 g, 1.67 mmol) were combined in a dry Fischer-Porter bottle. The reaction flask was purged with $N_2$, equipped with magnetic stirrer, and heated to 145° C. After 10 hours, analysis of an aliquot by HPLC indicated 90.9% Claisen product 31), 2.8% pre-Claisen enol ether 47, 1.3% 18a and 5% byproducts. Toluene (30.0 mL) was then added, and the mixture was filtered through celite. Concentration in vacuo of the filtrate afforded the crude product as an amber oil (2.6563 g). Analysis by quantitative HPLC indicated 82% purity, which corresponds to 2.1782 g Claisen product 31, (93% yield based on the mixture of 18a and pre-Claisen enol ether 47).

Procedure C: Purified 18a (0.228 g, 0.417 mmol) was placed in a 100 mL round-bottom flask. The reaction flask was placed in a Kugelrohr apparatus and evacuated to 100 mtorr. After 1 hr, the apparatus was heated to 40° C. After 15 minutes more, the apparatus was heated to 145° C. After 1 hr, the apparatus was cooled to R.T. to afford an dark oil (0.171 g). Analysis by HPLC indicated 88% Claisen product 31 3% pre-Claisen enol ether 47, 3% 18a and 6% byproducts. This corresponds to an 81% yield based on 18a. Quantitative HPLC was not performed.

For characterization, a portion of the residue was purified by flash column chromatography on silica gel (eluting with EtOAc/hexanes), concentrated in vacuo, and the desired product was collected as an amber oil: HPLC($CH_3CN/H_2O$): rt=29.1 min. $^1$H NMR ($CDCl_3$) ??0.88 (t, J=6.9 Hz, 3H), 1.06 (m, 1H), 1.17–1.34 (m, 3H), 1.61 (d, J=6.3 Hz, 3H), 1.68 (m, 1H), 1.83–1.93 (m, 1H), 2.42 (dd, J=14.4, 6.6 Hz, 1H), 2.63 (dd, J=14.7, 8.1 Hz, 1H), 3.12 (s, 2H), 3.80 (s, 3H), 4.52 (ABq, 2H), 5.16–5.26 (m, 1H), 5.52–5.64 (m, 1H), 6.88 (d, J=8.4 Hz, 2H), 7.11 (d, J=8.7 Hz, 2H), 8.09 (s, 1H), 8.21 (s, 1H), 8.22 (s, 1H), 9.40 (s, 1H)?? $^{13}$C NMR ($CDCl_3$) ? 13.7, 17.9, 22.8, 25.6, 32.6, 35.9, 37.2, 52.6, 55.1, 57.2, 114.4, 121.7, 123.4, 127.1, 129.8, 130.2, 131.2, 131.5, 143.7, 144.5, 150.5, 158.7, 202.5. HRMS (ES+) calcd for $C_{25}H_{31}NO_6S+NH_4$: 491.2216, found: 491.2192. Anal. ($C_{25}H_{31}NO_6S$): C, 63.40; H, 6.60; N, 2.96; O, 20.27; S, 6.77. Found: C, 63.36; H, 6.39; N, 3.05; O, 20.59; S, 6.71.

Other Reactions to Form Claisen Product 31

General procedure for other reactions of acetal to: In a typical reaction, the purified acetal 18a is combined with solvent, base and water removing agent (if indicated) and heated. The zeolites and molecular sieves are activated at 300° C. The reported conversion is based on the peak area of 31 vs. 18a in the HPLC data. The reported yield is based on the peak area of the products vs. byproducts in the HPLC data. The results are summarized below.

| Example No. | Base/Conditions | Results |
|---|---|---|
| 30 | 100° C. | 95% conv./32% yield @ 4 hrs. |
| 31 | 4 A sieves/o-xylene/145° C. | 6% conv./39% yield @ 5 hrs. |
| 32 | o-xylene/120° C. | 100% conv./58% yield @ 2.5 |

-continued

| Example No. | Base/Conditions | Results |
|---|---|---|
| 33 | o-xylene/145° C. | 100% conv./70% yield @ 2 hrs. |
| 34 | $CH_3CN$/140° C. | 0% conv. @ 6 hrs. |
| 35 | PPTS(0.1 eq.)/pyr.(0.15 eq.)/o-xylene/120° C. | 84% conv./74% yield @ 3 hrs. |
| 36 | PPTS(0.13 eq.)/4 A sieves/o-xylene/120° C. | 21% conv./74% yield @ 1 hrs. |
| 37 | pyr.(9.0 eq.)/$CH_3CN$/140° C. | 0% conv. @ 2.5 hrs. |
| 38 | pyr.(12.3 eq.)/xylenes/140° C. | 1% conv./100% yield @ 2 hrs. |
| 39 | $Et_3N$(0.3 eq.)/o-xylene/145° C. | 19% conv./78% yield @ 6 hrs. |
| 40 | $CaH_2$(0.46 eq.)/4 A sieves/o-xylene/145° C. | 97% conv./92% yield @ 5 hrs. |
| 41 | $CaH_2$(0.3 eq.)/$PhCH_3$/145° C. | 96% conv./95% yield @ 10 hrs. |
| 42 | $CaH_2$(0.43 eq.)/PTSA(0.07 eq.)/4 A sieves/o-xylene/145° C. | 100% conv./34% yield @ 1 hrs. |
| 43 | $CaH_2$(0.42 eq.)/4 A sieves/$CH_2Cl_2$/145° C. | 0.2% conv./11% yield @ 8 hrs. |
| 44 | $PhCH_3$/prefilter through basic alumina/145° C. | 98% conv./79% yield @ 3.5 hrs. |
| 45 | $AlCl_3$(2.0 eq.)/$Et_3N$(4.1 eq.)/THF/25° C. | 0% conv. @ 4 hrs. |
| 46 | $Pd(PhCN)_2Cl_2$ (0.1 eq.)/THF/25° C. | reversion to 32. |
| 47 | $BF_3 \cdot OEt_2$(1.2 eq.)/$CH_2Cl_2$/−50° C. | reversion to 32. |
| 48 | HMDS/TMSI/$CH_2Cl_2$/25° C. | 0% conv. @ 5 hrs. |

Other Reactions to Form Acetal 18a and the Pre-Claisen Enol Ether 47

General procedure: In a typical reaction, the sulfone aldehyde 32 is combined with 3-buten-2-ol (about 5 to about 50 eq.), solvent and acid source indicated. If indicated, 4 A molecular sieves (50 wt %), and trimethyl orthoformate TMOF (1.2 eq.) are added to the reaction flask. If no solvent is indicated, 3-buten-2-ol is the solvent. The zeolites and molecular sieves are activated at 300° C. The observed products are a mixture of the acetal 18a and the pre-Claisen enol ether, as determined by LCMS and NMR. The reported conversion is based on the peak area of product(s) vs. 32 in the HPLC data. The reported yield is based on the peak area of the products vs. byproducts in the HPLC data. The results are summarized below.

| Example No. | Acid/Conditions | Results |
|---|---|---|
| 49 | TFA(0.24 eq.)/CH$_3$CN/4 Å sieves/25° C. | 2.5% conv./50% yield @ 18 hrs. |
| 50 | TFA(3.5 eq.)/4 Å sieves/50° C. | 42% conv./74% yield @ 4.5 hrs. |
| 51 | TFA(3.8 eq.)/Isopropenyl acetate(3.3 eq.)/50° C. | 44% conv./95% yield @ 2 hrs. |
| 52 | TFA(3.5 eq.)/65° C. | 68% conv./86% yield @ 5.5 hrs. |
| 53 | TFA(3.0 eq.)/90° C. | 73% conv./75% yield @ 5.5 hrs. |
| 54 | TFA(3.0 eq.)/PhCH$_3$/4 Å sieves/TMOF/120° C. | 90% conv./53% yield @ 58 hrs. |
| 55 | TFA(3.0 eq.)/CH$_3$CN/4 Å sieves/TMOF/120° C. | 92% conv./58% yield @ 41 hrs. |
| 56 | PTSA(0.1 eq.)/25° C. | 78% conv./ 100% yield @ 16 hrs. |
| 57 | PTSA(0.1 eq.)/4 Å sieves/50° C. | 87% conv./99% yield @ 2 hrs. |
| 58 | PTSA(0.1 eq.)/4 Å sieves/70° C. | 95% conv./92% yield @ 5.75 hrs. |
| 59 | PTSA(0.1 eq.)/4 Å sieves/90° C. | 87% conv./74% yield @ 2 hrs. |
| 60 | PTSA(0.1 eq.)/Isopropenyl acetate (3.3 eq.)/50° C. | 63% conv./94% yield @ 2.5 hrs. |
| 61 | PTSA(0.12 eq.)/Isopropenyl acetate (3.2 eq.)/90° C. | 83% conv./91% yield @ 1 hrs. |
| 62 | PTSA(0.1 eq.)/PhCH$_3$/4 Å sieves/TMOF/90° C. | 29% conv./70% yield @ 18 hrs. |
| 63 | PTSA(0.3eq.)/PhCH$_3$/4 Å sieves/TMOF/120° C. | 37% conv./70% yield @ 70 hrs. |
| 64 | PTSA(0.1 eq.)/PhCH$_3$/49° C. @ 107.5 mmHg | 95% conv./93% yield @ 3.5 hrs. |
| 65 | PTSA(0.1 eq.)/o-xylene/4 Å sieves/50° C. | 92% conv./96% yield @ 3.5 hrs. |
| 66 | PTSA(0.1 eq.)/o-xylene/50° C. | 59% conv./58% yield @ 7.5 hrs. |
| 67 | PTSA(0.1 eq.)/CH$_2$Cl$_2$/4 Å sieves/47° C. | 95% conv./100% yield @ 3.5 hrs. |
| 68 | PTSA(0.05 eq.)/CH$_2$Cl$_2$/4 Å sieves/47° C. | 95% conv./99% yield @ 5 hrs. |
| 69 | PTSA(0.025eq.)/CH$_2$Cl$_2$/4 Å sieves/47° C. | 15% conv./91% yield @ 6.5 hrs. |
| 70 | PTSA(0.1 eq.)/CH$_2$Cl$_2$/47° C. | 100% conv./96% yield @ 1 hrs. |
| 71 | PTSA(0.1 eq.)/EtOAc/90° C. | 75% conv./85% yield @ 5 hrs. |
| 72 | PTSA(0.1 eq.)/EtOAc/4 Å sieves/50° C. | 44% conv./85% yield @ 1.5 hrs. |
| 73 | PTSA(0.1 eq.)/iPrOAc/4 Å sieves/50° C. | 62% conv./93% yield @ 6 hrs. |
| 74 | PTSA(0.1 eq.)/BuOAc/4 Å sieves/50° C. | 72% conv./69% yield @ 6 hrs. |
| 75 | PTSA(0.1 eq.)/THF/4 Å sieves/50° C. | 63% conv./94% yield @ 7 hrs. |
| 76 | PTSA(0.24 eq.)/CH$_3$CN/4 Å sieves/25° C. | 85% conv./100% yield @ 19 hrs. |
| 77 | PTSA(0.1 eq.)/MIBK/4 Å sieves/50° C. | 59% conv./95% yield @ 3 hrs. |
| 78 | PTSA(0.1 eq.)/PhCF$_3$/50° C. | 55% conv./65% yield @ 4 hrs. |
| 79 | PTSA(0.15 eq.)/Pd(PhCN)$_2$Cl$_2$ (0.09 eq.)/4 Å sieves/25° C. | 100% conv./97% yield @ 23 hrs. |
| 80 | PPTS(0.1 eq.)/4 Å sieves/ 90° C. | 65% conv./87% yield @ 7.5 hrs. |
| 81 | CBV 5020 zeolites(25 wt %)/CH$_3$CN/25 | 30% conv./97% yield @ 22 hrs. |
| 82 | CBV 5020 zeolites(25 wt %)/ 4 Å sieves/50° C. | 81% conv./99% yield @ 2 hrs. |
| 83 | CBV 5020 zeolites(25 wt %)/ 4 Å sieves/70° C. | 66% conv./94% yield @ 24 hrs. |
| 84 | CBV 5020 zeolites(25 wt %)/ 4 Å sieves/90° C. | 81% conv./98% yield @ 1 hrs. |
| 85 | CBV 5020 zeolites(25 wt %)/ 90° C. | 71% conv./93% yield @ 2 hrs |
| 86 | CBV 5020 zeolites(25 wt %)/Isopropeny acetate (3.0 eq.)/90° C. | 79% conv./91% yield @ 1.5 hrs. |
| 87 | CBV 5020 zeolites(10 wt %)/PhCH$_3$/4 Å sieves/TMOF/ 120° C. | 40% conv./53% yield @ 21 hrs. |

-continued

| Example No. | Acid/Conditions | Results |
|---|---|---|
| 88 | 300WN0030 g zeolites(10 wt %)/PhCH$_3$/4 Å sieves/ TMOF/120° C. | 22% conv./57% yield @ 21 hrs. |
| 89 | Montmorillonite K10(10 wt. %)/PhCH$_3$/4 Å sieves/TMOF/120° C. | 70% conv./64% yield @ 57 hrs. |
| 90 | Montmorillonite K10(20 wt %)/ 4 Å sieves/25° C. | 4% conv./99% yield @ 18 hrs. |
| 91 | Montmorillonite K10(20 wt %)/CH$_3$CN/4 Å sieves/25° C. | 4% conv./99% yield @ 21 hrs. |
| 92 | Amberlyst 15(20 wt. %)/ CH$_2$Cl$_2$/4 Å sieves/47° C. | 49% conv./96% yield @ 2 hrs. |
| 93 | Acetic acid(0.24 eq.)/ CH$_3$CN/4 Å sieves/25° C. | 0% conv./0% yield @ 22 hrs. |
| 94 | Acetic acid(3.0 eq.)/90° C. | 15% conv./78% yield @ 2.5 hrs. |
| 95 | Acetic acid (3.0 eq.)/4 Å sieves/90° C. | 79% conv./84% yield @ 6.5 hrs. |
| 96 | HCl (0.20 eq.)/25° C. | 3% conv./6% yield @ 1 hrs. |
| 97 | HCl (4.1 eq.)/4 Å sieves/ 25° C. | 87% conv./98% yield @ 2.5 hrs. |
| 98 | HCl (1.1 eq.)/dioxane/4 Å sieves/25° C. | 67% conv./100% yield @ 1 hrs. |
| 99 | HCl (1.1 eq.)/CH$_2$Cl$_2$/4 Å sieves/47° C. | 69% conv./100% yield @ 1 hrs. |
| 100 | AlClEt$_2$/(0.16 eq.)/4 Å sieves/25° C. | 80% conv./59% yield @ 47 hrs. |
| 101 | Pd(PPh$_3$)$_4$ (0.10 eq.)/4 Å sieves/25° C. | retro-Michael reaction only |
| 102 | Pd(PhCN)$_2$Cl$_2$ (0.10 eq.)/ THF/4 Å sieves/25° C. | 5% conv./47% yield @ 4.5 hrs. |
| 103 | Pd(PhCN)$_2$Cl$_2$ (0.12 eq.)/ 4 Å sieves/25° C. | 63% conv./100% yield @ 2 hrs. |

EXAMPLE 104

Preparation of Compound 29

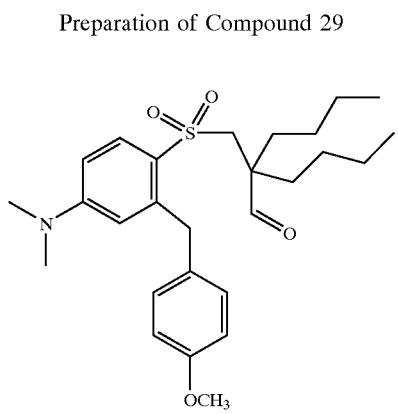

29

To a solution of 0.434 g of compound 31 in 30 mL of hot ethanol was added 5 mL of 37% formaldehyde and 220 mg of 20% Pd(OH)$_2$/C catalyst. The reaction mixture was purged with nitrogen gas (3×) and H2 (3×) and hydrogenated at 60 psi and 60° C. for 15 hours. The catalyst was removed by filtration and washed with ethanol (2×20 mL). Solvents of the combined washes and filtrate were removed to yield 370 mg of crude 29 (85%). An analytical sample was obtained by recrystallization from ethanol and water.

EXAMPLE 105

Preparation of Compound 12c

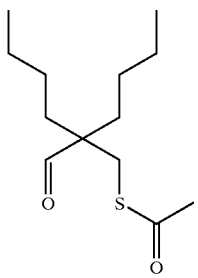

12c

A 1L 3-neck jacked flask is fitted with baffles, a bottom valve, an overhead stirred, an addition funnel, and a Neslab cooling bath. To the reactor is charged 35 grams of potassium thioacetate. The reactor is flushed with nitrogen gas and to it is charged 85 mL of dimethylformamide (DMF). Mixing is started at 180 rpm and the bath is cooled to 18° C. The reactor is again flushed with nitrogen gas and to it is added 73.9 grams of compound 53 over 20 minutes via a dropping funnel. The pot temperature is maintained at 23° C. during the addition. The mixture is stirred for 1 hour at about 23° C. to 27° C. To the mixture is then added 80 mL of water followed by 100 mL of ethyl acetate. The mixture is stirred for 20 minutes. The layers are allowed to separate and the aqueous layer is drained off. To the pot is added another 50 mL of water and the mixture is stirred for 15 minutes. The layers are separated and the aqueous layer is drained off. Then to the pot is added 50 mL of brine and the mixture is stirred for another 15 minutes. The layers are separated and the aqueous layer is removed. The organic layer is concentrated under reduced pressure (water aspirator pressure) at 47° C. to obtain 68.0 grams of orange oily compound 12c.

EXAMPLE 106

Preparation of Diethyl Acetal Compound 12d

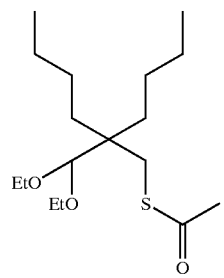

12d

A 250 mL 3-neck round bottom flask is fitted with an overhead stirrer, a Teflon coated temperature probe, and a separatory funnel. To the flask is charged 78 g of compound 12c and 200 mL of ethanol. The reactor is flushed with nitrogen gas and to it is charged 60 mL of triethylorthoformate. Then to the flask is added 4 grams of p-toluenesulfonic acid. The mixture is stirred at room temperature for 16 hours. The mixture is then concentrated under reduced pressure and to the flask is added 100 mL of ethyl acetate. Next is added 1.7 grams of sodium bicarbonate in 50 mL of water. The mixture is stirred for 3 minutes. The layers are allowed to separate and the aqueous layer is drained. The organic layer is filtered through a pad of sodium sulfate and the organic layer is concentrated under reduced pressure (water aspirator pressure) to afford 96.42 grams of orange oily compound 12d.

EXAMPLE 107

Preparation of Diethyl Acetal Compound 67

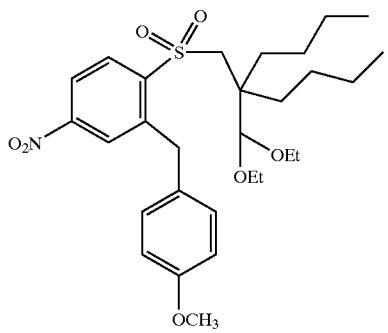

67

A 0.5 L 3-neck jacked flask is fitted with baffles, a bottom valve, an overhead stirrer, an addition funnel, a nitrogen inlet, a silicon oil bubbler, a Teflon-coated temperature probe, and a PolyScience cooling/heating bath. To the flask is charged 48.85 grams of compound 33. The flask is flushed with nitrogen gas and to it is charged 75 mL of DMSO. The mixture is again flushed with nitrogen and agitation is begun. The jacket temperature is set at 40° C. and to the flask is added 56.13 grams of compound 12d. Stirring is continued for 30 minutes and to the mixture is slowly added 28 mL of 50% aqueous NaOH over 120 minutes via a dropping funnel. The mixture is stirred for 3 hours while maintaining the jacket temperature at 40° C. The reaction is allowed to cool to ambient temperature and the mixture is stirred for 15 hours (overnight). The jacket temperature is then adjusted to 5° C. and to the mixture is slowly added 300 mL of water. The reaction is exothermic. The biphasic mixture is transferred to a separatory funnel and the mixture is extracted with 2×150 mL of ethyl acetate. The layers were allowed to separate for 30 minutes and the aqueous layer was drained off. The ethyl acetate layers are combined. The combined ethyl acetate mixture is extracted successively with 400 mL and 100 mL of water. If the layers do not readily separate within 30 minutes, 50 mL of brine may be added to the mixture to aid in separation of the layers. The aqueous layer is drained off. The ethyl acetate layer is then extracted with 100 mL of brine. The ethyl acetate layer is then dried over anhydrous magnesium sulfate and the solids are filtered off through a plug of activated charcoal/Supercel Hyflow. The filtrate is concentrated under reduced pressure and dried under vacuum for 18 hours to obtain 91.98 grams of an orange-brown, viscous oil (compound 67).

EXAMPLE 108

Conversion of Diethyl Acetal Compound 67 to 1-(2,2-Dibutyl-3-oxopropylsulfonyl)-2-((4-methoxyphenyl)methyl)benzene (29)

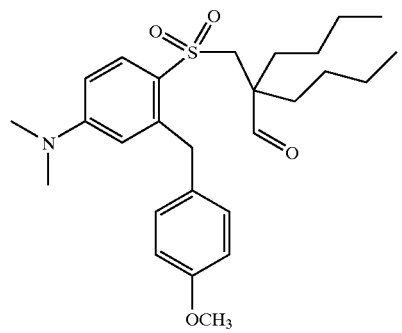

29

Compound 67 (36 grams dissolved in 122 mL of ethyl acetate), 300 mL acetic acid, 27.3 g of 37 wt % formaldehyde, and 50 mL of water are charged into a 500 mL 1-neck round bottom flask in a Parr Shaker. To the mixture is added 7.4 grams of 5% Pd/C (dry basis, Johnson Mathey). The reactor is purged three times with nitrogen gas and then purged three times with hydrogen gas. The reactor is pressurized to 60 psi and heated to 60° C. The temperature and pressure are held for 16 hours after which time the reactor is allowed to cool to room temperature. The reaction mixture is filtered through a pad of solka flock on a course fritted glass filter. The cake is washed twice with 40 mL of acetic acid and concentrated to dryness under reduced pressure. The solid is mixed with 100 mL ethanol and heated to 80° C. until all the solid is dissolved. To this is added 20 mL of tap water to form a homogeneous solution. The mixture is cooled to room temperature and to it is added 3 mL of ethyl acetate. A white slurry forms. The slurry is heated to 60° C. until a homogeneous solution forms. The mixture is cooled to room temperature and held for two hours. During this time compound 29 crystallizes. The solids are filtered through a coarse fritted glass filter. The cake is washed twice with 40 mL of a 20% (V/V) ethanol in water

EXAMPLE 109

Preparation of 2-(Acetylthiomethyl)-2-butyl-4-hexenal Ethylene Glycol Acetal, 74

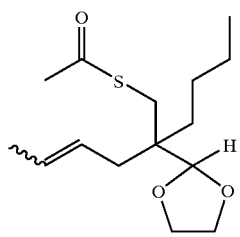

74

Step 1. Preparation of 2-(Acetylthiomethyl)hexanal, 72.

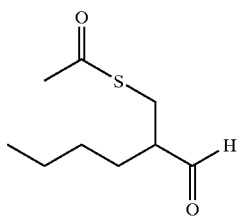

72

A 1 L 3-neck round bottom flask is fitted with a magnetic stir bar, a nitrogen inlet, a thermometer probe connected to a temperature monitor, a 50 mL addition funnel, and an ice-water bath. Into the flask is charged 37.0 mL of thiolacetic acid and the flask contents are cooled to 0–5° C. in the ice-water bath. To the flask is then charged 69.0 mL of butylacrolein via the addition funnel over 2 minutes. The temperature increases to a maximum of about 21° C. The reaction is cooled then to about 10° C. and the flask is charged with 0.72 mL of triethylamine. The temperature increases to about 57° C. within about one minute. Stirring continues until the temperature drops to about 15° C. The resulting product mixture contains compound 72.

Step 2. Preparation of 2-(Acetylthiomethyl)-2-butyl-4-hexenal, 73.

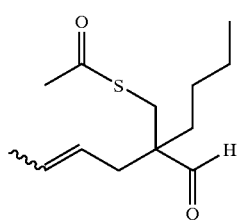

73

The apparatus of Step 1 of this example is further fitted with a Dean-Stark trap and a cold water condenser. The reaction flask, containing the product mixture of Step 1, is further charged with 50.0 mL of 3-buten-2-ol, 1.987 g of p-toluenesulfonic acid monohydrate, and 600 mL of toluene. The mixture is heated to about 105–110° C. with stirring for about 24 hours. During this time water, as well as some 3-buten-2-ol and toluene collect in the Dean-Stark trap. The reaction is complete when no more water distills over. If desired, an additional 0.5 equivalents of 3-buten-2-ol can be added to the flask to make up for loss from distillation. The mixture is allowed to cool to ambient temperature. The resulting aldehyde mixture contains compound 73.

Step 3. Preparation of 2-(Acetylthiomethyl)-2-butyl-4-hexenal Ethylene Glycol Acetal, 74.

The apparatus and resulting aldehyde mixture of Step 2 of this example are further charged with 31.0 mL of ethylene glycol. The mixture is heated with stirring to 105–110° C. for 2 hours. Water and toluene collect in the Dean-Stark trap during this time. The reaction is complete when no more water distills over. The mixture is cooled to ambient temperature and the reaction mixture is washed successively with 100 mL of saturated sodium bicarbonate aqueous solution, 100 mL of water, and 100 mL of brine. The solvent is removed by evaporation in a rotary evaporator. The yield is 149 grams of compound 74.

EXAMPLE 110

Preparation of Compound 67

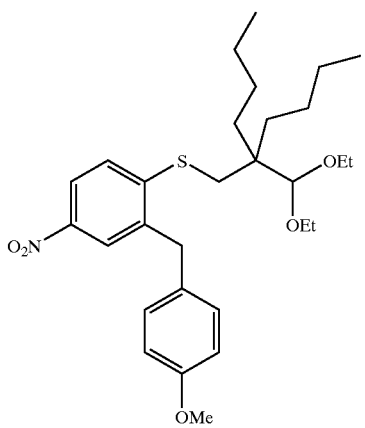

67

Step 1. Preparation of 2-(Acetylthiomethyl)-2-butyl-4-hexenal Diethyl Acetal, 75.

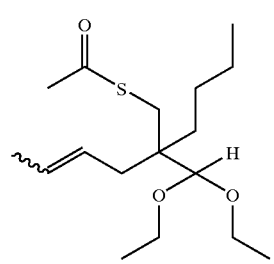

75

A 250 mL 3-neck round bottom flask is fitted with an overhead stirrer, a Teflon coated temperature probe, and a separatory funnel. To the flask is charged 78 g of compound 74 and 200 mL of ethanol. The reactor is flushed with nitrogen gas and to it is charged 60 mL of triethylorthoformate. Then to the flask is added 4 grams of p-toluenesulfonic acid. The mixture is stirred at room temperature for 16 hours. The mixture is then concentrated under reduced pressure and to the flask is added 100 mL of ethyl acetate. Next is added 1.7 grams of sodium bicarbonate in 50 mL of water. The mixture is stirred for 3 minutes. The layers are allowed to separate and the aqueous layer is drained. The organic layer is filtered through a pad of sodium sulfate and the organic layer is concentrated under reduced pressure (water aspirator pressure) to afford compound 75.

Step 2. Preparation of 2-butyl-2-(thiomethyl)hexanal Diethyl Acetal, 76.

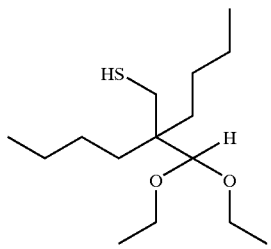

A 500 mL 3-neck round bottom flask is fitted with a condenser, a magnetic stir bar, a nitrogen inlet, a thermocouple connected to a temperature controller, and a heating mantle. The flask is purged with nitrogen gas and charged with 19.2 grams of compound 75, 96 mL of N-methylpyrrolidone (NMP), 28.3 grams (2.5 equiv.) of p-toluenesulfonyl hydrazide, and 18 mL (3.0 equiv.) of piperidine. While stirring, the mixture is warmed to about 100° C. for 2 hours. The temperature is kept below 107° C. by removing the heat, if necessary. The mixture is cooled to ambient temperature. The product mixture contains compound 76. If desired, this reaction can be run using 2.5 equiv. of p-toluenesulfonyl hydrazide and 2.5 equiv. of piperidine.

Step 3. Preparation of Compound 67.

The equipment and product mixture of Step 2 of this example are used in this step. To the flask containing the product mixture of Step 2 is charged 13.46 grams of compound 33 and 11.2 mL of 50% (w/w) aqueous NaOH. The mixture is heated to 100° C. with mixing and held at that temperature for 2.5 hours. The mixture is cooled to ambient temperature and to the flask is added 100 mL of ethyl acetate. This mixture is washed with 100 mL of water. The aqueous layer is separated and washed with 100 mL of ethyl acetate. The ethyl acetate layers are combined and washed in succession with 3×100 mL of water and with 2×50 mL of brine. The organic layer is dried over magnesium sulfate and the solvent is removed under vacuum in a rotary evaporator. The yield is 26 grams of compound 67 as a reddish brown oil.

EXAMPLE 111

Differential Scanning Calorimetry (DSC)

DSC experiments are performed either on a Perkin Elmer Pyris 7 Differential Scanning Calorimeter or on a TA Instruments Differential Scanning Calorimeter with 5–10 mg samples hermetically sealed in a standard aluminum pan (40 microliters) with a single hole punched in the lid. An empty pan of the same type is used as a reference. The heating rate is 10° C./min with dry nitrogen purge. FIG. 9 shows typical DSC thermograms for Form I (plot(a)) and Form II (plot(b)) of compound 41.

EXAMPLE 112

X-Ray Powder Diffraction Patterns

X-ray powder diffraction experiments are conducted on an Inel theta/theta diffraction system equipped with a 2 kW normal focus X-ray tube (copper). X-ray scatter data are collected from 0 to 80° 2 theta. Samples are run in bulk configuration. Data are collected and analyzed on a Dell computer running Inel's software. In at least one case, samples are placed in a glass capillary tube and ends are sealed to prevent loss of solvent. The capillary is mounted on a special adapter in the path of the X-ray beam and data were collected.

Alternatively, the X-ray diffraction experiments are conducted on a system comprising a Siemens D5000 diffraction system equipped with a 2 kW normal focus X-ray tube (copper). The system is equipped with an autosampler system with a theta—theta sample orientation. Data collection and analysis is performed on a MS-Windows computer with Siemens' proprietary software.

FIG. 6 shows typical X-ray powder diffraction patterns for Form I (plot (a)) and Form II (plot(b)) of compound 41. Table 1 shows a summary comparison of prominent X-ray powder diffraction peaks for Form I and Form II.

TABLE 1

| Form I | | Form II | |
|---|---|---|---|
| 2-Theta Value | Relative Peak Intensity (%) | 2-Theta Value | Relative Peak Intensity (%) |
| 7.203 | 15.0665 | 9.1962 | 18.6166 |
| 8.45 | 29.0688 | 12.277 | 29.2318 |
| 9.726 | 37.1457 | 12.584 | 8.39048 |
| 11.205 | 49.0207 | 12.833 | 7.67902 |
| 11.786 | 10.8439 | 13.872 | 100 |
| 12.51 | 15.9267 | 14.286 | 77.5682 |
| 13.342 | 11.0306 | 15.168 | 7.54978 |
| 14.25 | 16.3005 | 15.641 | 16.0194 |
| 14.859 | 16.1351 | 15.935 | 11.4935 |
| 15.526 | 43.0987 | 16.138 | 16.6656 |
| 15.874 | 25.424 | 16.399 | 36.1255 |
| 16.309 | 14.278 | 16.544 | 77.6935 |
| 17.121 | 14.1898 | 17.094 | 13.1102 |
| 17.498 | 13.173 | 17.645 | 38.4531 |
| 18.542 | 99.3626 | 18.511 | 33.0226 |
| 19.354 | 85.1982 | 18.826 | 91.0787 |
| 19.789 | 16.7251 | 19.128 | 25.2644 |
| 20.34 | 39.3083 | 19.327 | 18.8639 |
| 20.891 | 27.5965 | 19.906 | 38.7122 |
| 21.297 | 16.2266 | 20.085 | 12.7865 |
| 22.022 | 26.6845 | 20.23 | 10.2004 |
| 23.304 | 42.0171 | 21.00 | 8.58433 |
| 25.125 | 17.2159 | 21.48 | 47.6981 |
| 25.734 | 18.2944 | 21.729 | 33.6048 |
| 27.503 | 25.8376 | 22.089 | 12.1403 |
| 32.056 | 12.7407 | 22.4 | 10.0712 |
| 35.188 | 22.4211 | 22.748 | 13.3041 |
| 40.166 | 16.7913 | 22.959 | 14.5971 |
| | | 23.22 | 13.498 |
| | | 23.472 | 17.8224 |
| | | 23.965 | 16.9247 |
| | | 24.553 | 16.8594 |
| | | 25.038 | 9.6835 |
| | | 25.299 | 13.0904 |
| | | 25.626 | 13.9503 |
| | | 25.767 | 14.9202 |
| | | 25.887 | 11.2996 |
| | | 26.343 | 18.1531 |
| | | 26.873 | 9.87736 |
| | | 27.941 | 15.1787 |
| | | 28.228 | 15.4437 |
| | | 28.815 | 11.2996 |
| | | 29.475 | 13.7532 |
| | | 34.758 | 21.773 |
| | | 40.176 | 21.0731 |

EXAMPLE 113

Fourier Transform Infrared Spectra

The Fourier transform infrared (FTIR) spectra for Form I and Form II of compound 41 are obtained using a Bio-Rad FTS-45 Fourier-transform infrared spectrometer equipped with a micro-ATR (attenuated total reflectance) beam condensing accessory (IBM Corporation) mounted in the sample compartment of the instrument. The sample compartment and optical bench of the spectrometer is under a nitrogen purge. The software used for operating the instrument and collecting the spectrum is Bio-Rad's Windows 98-based Win-IR software. The spectra are obtained using an 8-wavenumber resolution and 16 scans.

A small amount of sample is placed onto one side of a 5×10×1 mm KRS5 (a type of infrared transmitting material commonly used in the IR world) ATR crystal, and lightly tamped with a stainless steel micro spatula in order to ensure good contact of the sample with the face of the crystal. The crystal is mounted into the ATR beam-condensing accessory, and the sample compartment allowed to purge for a few minutes to remove water vapor and carbon dioxide (their presence reduces the quality of the spectrum). This can be monitored on the screen of the operating console, and when down to an acceptable level, the 16 scans are collected to produce an interferogram. Prior to analyzing the sample, a clean KRS5 crystal is mounted on the ATR accessory and a background interferogram collected. The purge time and number of scans for collecting the background should be the same as will be used for analyzing the sample.

The Fourier-transform of the resulting interferogram is automatically done and spectrum appears on the screen. The resulting spectrum is then smoothed and baseline corrected, if necessary, then ATR corrected to obtain a spectrum that is comparable to an absorption or transmission spectrum.

FIG. 7 shows typical FTIR spectra for Form I (plot (a)) and Form II (plot (b)) of compound 41. Table 2 shows a summary comparison of prominent FTIR peaks for Form I and Form II.

TABLE 2

| Form I Peaks (cm$^{-1}$) | Form II Peaks (cm$^{-1}$) |
|---|---|
| 3163 | 3250 |
| 2870 | 2885 |
| 1596 | 1600 |
| 1300 | 1288 |
| 1239 | 1225 |
| 1182 | 1172 |
| 1055 | 1050 |
| 986 | 990 |
| 855 | 858 |
| 825 | 837 |
| 627 | 620 |

EXAMPLE 114

State Carbon-13 NMR Analysis

Solid-state NMR. Cross-polarization magic-angle spinning (CPMAS) $^{13}$C NMR spectra were collected on a Monsanto-built spectrometer operating at a proton resonance frequency of 127.0 MHz. Samples were spun at the magic angle with respect to the magnetic field in a double-bearing rotor system at a rate of 3 kHz. CPMAS$^{13}$C NMR spectra were obtained at 31.9 MHz following 2-ms matched, 50-kHz $^{1}$H-$^{13}$C cross-polarization contacts. High-power proton dipolar decoupling ($H_1(H)$=65–75 kHz) was used during data acquisition. Residual spinning sidebands were suppressed using the Total Suppression of Sidebands (TOSS) method. In each experiment, approximately 219 mg of Form I and approximately 142 mg Form II are used.

FIG. 8 shows typical solid-state $^{13}$C nuclear magnetic resonance (NMR) spectra for Form I (plot (a)) and Form II (plot (b)) of compound 41. Table 3 shows a summary comparison of prominent solid-state $^{13}$C NMR peaks for Form I and Form II.

TABLE 3

| Form I (ppm) | Form II (ppm) |
|---|---|
| 158.55 | 157.971 |
| 151.712 | 142.325 |
| 145.986 | 137.172 |
| 140.852 | 134.043 |
| 136.628 | 127.232 |
| 133.489 | 125.390 |
| 128.151 | 118.212 |
| 120.052 | 113.057 |
| 115.266 | 106.615 |
| 113.241 | 76.795 |
| 109.928 | 68.512 |
| 76.795 | 57.100 |
| 68.860 | 47.712 |
| 54.523 | 43.661 |
| 46.239 | 37.951 |
| 43.847 | 21.942 |
| 40.901 | 14.763 |
| 24.519 | 13.281 |
| 14.395 | |
| 3.351 | |

EXAMPLE 115

Water Uptake Experiments

Water sorption experiments are performed on a Dynamic Vapor Sorption (DVS) apparatus (DVS-1000 manufactured by Surface Measurements Systems, Inc.). Experiments are performed at 25° C. by initially drying the material of interest (about 10 mg sample) from 30% relative humidity (RH) (ambient room condition) to about 9% RH in a stepwise fashion (10% RH step) by purging with dry nitrogen until no further weight change was observed. The samples are then exposed to a stepwise (10% RH steps) increase in RH from about 0 to about 90% RH. Each successive step is initiated when the change in weight over time at the relative humidity was less than 0.0003% (($dm/dt$)/$m_0$×100, where m is mass in mg, $m_0$ is initial mass, and t is time in minutes). The sample is then taken through the reverse of the stepwise % RH increase. The data are collected on a computer and analyzed using SMS' proprietary MS-Excel macro interface software. FIG. 10 shows typical water sorption isotherm results for Form I (plot (a)) and Form II (plot (b)) of compound 41. Table 4 shows a summary comparison of water sorption and desorption isotherms for Form I and Form II at 25° C.

TABLE 4

| % RH at 25° C. | Sorption % Weight Change | Desorption % Weight Change |
|---|---|---|
| | Form I | |
| 0.45 | 0.057 | 0.057 |
| 9.2 | 0.9575 | 0.997 |
| 20.05 | 2.016 | 2.1025 |
| 29.75 | 3.4105 | 3.599 |
| 39.4 | 4.282 | 4.743 |
| 49.55 | 4.928 | 5.321 |
| 59.4 | 5.356 | 5.726 |

TABLE 4-continued

| % RH at 25° C. | Sorption % Weight Change | Desorption % Weight Change |
|---|---|---|
| 69.05 | 5.706 | 6.054 |
| 78.8 | 6.109 | 6.357 |
| 88.5 | 6.734 | 6.734 |
| Form II | | |
| 1.3 | −0.02695 | −0.02695 |
| 9.35 | 0.04715 | 0.04235 |
| 20.25 | 0.10585 | 0.09715 |
| 29.75 | 0.13755 | 0.14435 |
| 39.55 | 0.1809 | 0.1866 |
| 49.7 | 0.2386 | 0.2636 |
| 59.5 | 0.304 | 0.331 |
| 69.1 | 0.3945 | 0.3983 |
| 78.65 | 0.4695 | 0.4849 |
| 88.5 | 0.6446 | 0.6446 |

The examples herein can be performed by substituting the generically or specifically described reactants and/or operating conditions of this invention for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A compound having the structure of Formula (29)

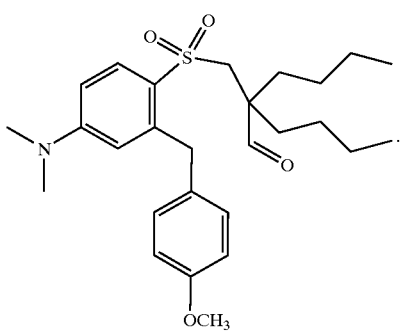

(29)

2. A compound having the structure of Formula (30)

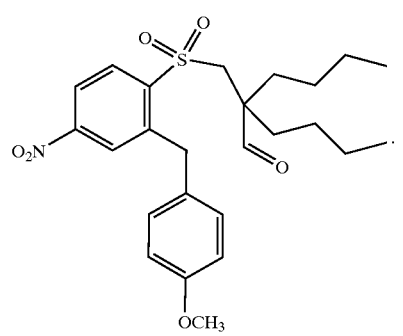

(30)

3. 2-Bromomethyl-2-butylhexanal.
4. 2-Bromomethyl-2-butylhexanol.
5. 1-Acetato-2-butyl-2-(hydroxymethyl)hexane.

6. A compound having the structure of Formula (31)

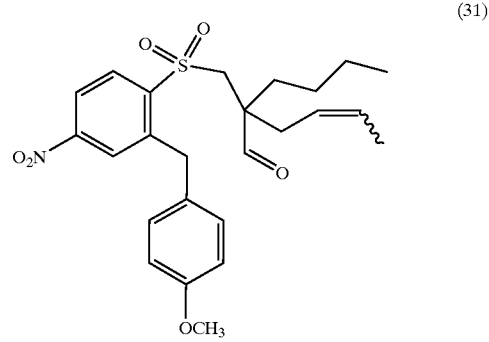

(31)

wherein Formula (31) represents a compound having either an E or a Z configuration about the butenyl double bond.

7. The compound of claim 6 having an E configuration about the butenyl double bond.

8. The compound of claim 6 having a Z configuration about the butenyl double bond.

9. A compound having the structure of Formula (32)

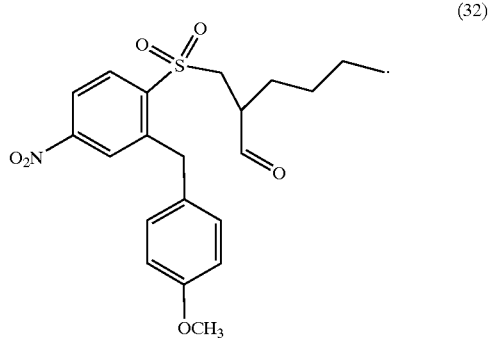

(32)

10. A compound having the structure of Formula (11)

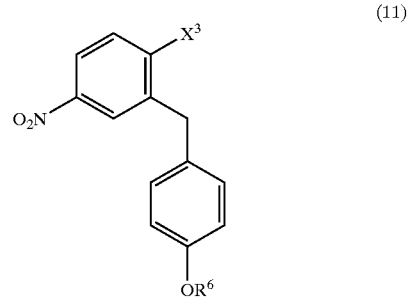

(11)

wherein $R^6$ is a protecting group and $X^3$ is an aromatic substitution leaving group.

11. The compound of claim 10 wherein $X^3$ is a halo group.

12. The compound of claim 11 wherein $X^3$ is chloro.

13. The compound of claim 10 wherein $R^6$ is $C_1$ to about $C_{20}$ alkyl.

14. The compound of claim 13 wherein $R^6$ is $C_1$ to about $C_{10}$ alkyl.

15. The compound of claim 14 wherein $R^6$ is $C_1$ to about $C_5$ alkyl.

16. The compound of claim 15 wherein $R^6$ is methyl.

17. A compound having the structure of Formula (13)

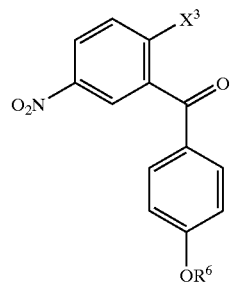
(13)

wherein $R^6$ is a protecting group and $X^3$ is an aromatic substitution leaving group.

18. The compound of claim 17 wherein $X^3$ is a halo group.

19. The compound of claim 18 wherein $X^3$ is chloro.

20. The compound of claim 17 wherein $R^6$ is $C_1$ to about $C_{20}$ alkyl.

21. The compound of claim 20 wherein $R^6$ is $C_1$ to about $C_{10}$ alkyl.

22. The compound of claim 21 wherein $R^6$ is $C_1$ to about $C_5$ alkyl.

23. The compound of claim 22 wherein $R^6$ is methyl.

24. A method for the preparation of a substituted propionaldehyde compound having the structure of Formula 12

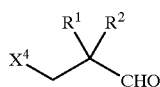
12 wherein the method comprises oxidizing a substituted propanol compound having the structure of Formula 35

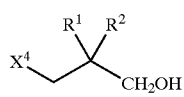
35 wherein $R^1$ and $R^2$ independently are $C_1$ to about $C_{20}$ hydrocarbyl and $X^4$ is a nucleophilic substitution leaving group.

25. The method of claim 24 wherein one of $R^1$ and $R^2$ is ethyl and the other of $R^1$ and $R^2$ is butyl.

26. The method of claim 25 wherein the substituted propionaldehyde compound has an R absolute configuration.

27. The method of claim 25 wherein the substituted propionaldehyde compound has an S absolute configuration.

28. The method of claim 24 wherein $R^1$ and $R^2$ are both butyl.

29. The method of claim 24 further comprising a step in which an acid ester having the structure of Formula 36

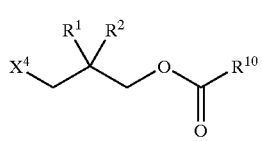
36 is solvolyzed to form the substituted propanol compound, wherein $R^{10}$ is a $C_1$ to about $C_{20}$ alkyl group.

30. The method of claim 24 wherein $X^4$ is halo.

31. The method of claim 30 wherein $X^4$ is bromo.

32. The method of claim 30 further comprising a step in which a diol compound having the structure of Formula 37

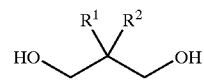
37 is reacted in the presence of carbonyl compound having the structure of Formula 38

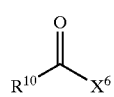
38 and a source of halide to form the acid ester, wherein $X^6$ is selected from the group consisting of hydroxy, halogen, and —OC(O)$R^{18}$, wherein $R^{18}$ is $C_1$ to about $C_{20}$ hydrocarbyl.

33. The method of claim 32 wherein the source of halide is selected from the group consisting of a source of HBr and a source of HI.

34. The method of claim 33 wherein the source of halide is a source of HBr.

35. A method for the preparation of a substituted propionaldehyde compound having the structure of Formula 12

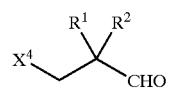
12 wherein the method comprises the steps of:

(a) reacting a diol compound having the structure of Formula 37

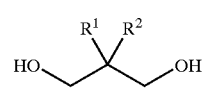
37 in the presence of a carbonyl compound having the structure of Formula 38

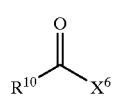
38 and a source of halide to form an acid ester having the structure of Formula 36

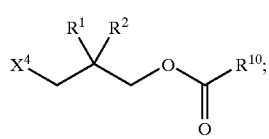
36

(b) solvolyzing the acid ester to form a substituted propanol compound having the structure of Formula 35

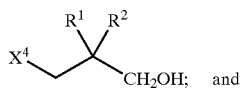

35

(c) oxidizing the substituted propanol compound to form the substituted propionaldehyde compound;

wherein:

$R^1$, $R^2$, $R^{10}$, and $R^{18}$ independently are $C_1$ to about $C_{20}$ hydrocarbyl;

$X^4$ is a nucleophilic substitution leaving group; and $X^6$ is selected from the group consisting of hydroxy, halo, and —OC(O)$R^{18}$.

36. The method of claim 35 wherein the carboxylic acid equivalent is a carbonyl compound having the structure of Formula 38

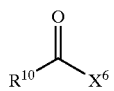

38 wherein $X^6$ is selected from the group consisting of hydroxy, halo, and —OC(O)$R^{18}$.

37. The method of claim 36 wherein $R^1$, $R^2$, $R^{10}$, and $R^{11}$ independently are $C_1$ to about $C_{10}$ hydrocarbyl.

38. The method of claim 37 wherein $R^1$, $R^2$, $R^{10}$, and $R^{18}$ independently are $C_1$ to about $C_5$ hydrocarbyl.

39. The method of claim 38 wherein one of $R^1$ and $R^2$ is ethyl and the other of $R^1$ and $R^2$ is butyl.

40. The method of claim 38 wherein both $R^1$ and $R^2$ are butyl.

41. The method of claim 40 wherein $R^{10}$ is methyl.

42. The method of claim 38 wherein $R^{18}$ is methyl.

43. The method of claim 42 wherein $X^4$ is halo.

44. The method of claim 43 wherein $X^4$ is bromo.

45. The method of claim 44 wherein $X^6$ is hydroxy.

* * * * *